(12) United States Patent
Habib et al.

(10) Patent No.: US 9,216,176 B2
(45) Date of Patent: *Dec. 22, 2015

(54) ABUSE RESISTANT DRUG FORMULATION

(71) Applicant: CIMA LABS INC., Brooklyn Park, MN (US)

(72) Inventors: Walid A. Habib, Riyadh (SA); Ehab Hamed, Concord, MA (US); Manuel A. Vega Zepeda, Minnetonka, MN (US)

(73) Assignee: Cima Labs Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,854

(22) Filed: May 18, 2015

(65) Prior Publication Data

US 2015/0250730 A1  Sep. 10, 2015

Related U.S. Application Data

(63) Continuation of application No. 13/728,801, filed on Dec. 27, 2012, which is a continuation of application No. 12/075,543, filed on Mar. 12, 2008, now Pat. No. 8,445,018, which is a continuation-in-part of application No. 11/900,851, filed on Sep. 13, 2007, now abandoned.

(60) Provisional application No. 60/850,456, filed on Oct. 10, 2006, provisional application No. 60/845,151, filed on Sep. 15, 2006, provisional application No. 60/845,128, filed on Sep. 15, 2006, provisional application No. 60/845,127, filed on Sep. 15, 2006, provisional application No. 60/845,126, filed on Sep. 15, 2006.

(51) Int. Cl.
| | |
|---|---|
| A61K 31/485 | (2006.01) |
| A61K 9/16 | (2006.01) |
| A61K 9/20 | (2006.01) |
| A61K 9/50 | (2006.01) |
| A61K 9/14 | (2006.01) |
| A61K 47/44 | (2006.01) |

(52) U.S. Cl.
CPC ............ *A61K 31/485* (2013.01); *A61K 9/14* (2013.01); *A61K 9/1652* (2013.01); *A61K 9/1694* (2013.01); *A61K 9/2013* (2013.01); *A61K 9/2018* (2013.01); *A61K 9/2054* (2013.01); *A61K 9/2077* (2013.01); *A61K 9/2081* (2013.01); *A61K 9/5042* (2013.01); *A61K 9/5047* (2013.01); *A61K 47/44* (2013.01)

(58) Field of Classification Search
None
See application file for complete search history.

(56) References Cited

U.S. PATENT DOCUMENTS

| | | |
|---|---|---|
| 4,814,176 A | 3/1989 | Makino et al. |
| 4,844,909 A | 7/1989 | Goldie et al. |
| 4,861,598 A | 8/1989 | Oshlack |
| 4,863,456 A | 9/1989 | Stephens et al. |
| 4,873,092 A | 10/1989 | Azuma et al. |
| 4,970,075 A | 11/1990 | Oshlack |
| 4,990,341 A | 2/1991 | Goldie et al. |
| 5,133,974 A | 7/1992 | Paradissis et al. |
| 5,169,645 A | 12/1992 | Shukla et al. |
| 5,178,878 A | 1/1993 | Wehling et al. |
| 5,248,669 A | 9/1993 | Amer |
| 5,266,331 A | 11/1993 | Oshlack et al. |
| 5,273,760 A | 12/1993 | Oshlack et al. |
| 5,286,493 A | 2/1994 | Oshlack et al. |
| 5,321,012 A | 6/1994 | Mayer et al. |
| 5,352,683 A | 10/1994 | Mayer et al. |
| 5,403,593 A | 4/1995 | Royce |
| 5,445,829 A | 8/1995 | Paradissis et al. |
| 5,458,879 A | 10/1995 | Singh et al. |
| 5,460,828 A | 10/1995 | Santus et al. |
| 5,472,712 A | 12/1995 | Oshlack et al. |
| 5,478,577 A | 12/1995 | Sackler et al. |
| 5,500,227 A | 3/1996 | Oshlack et al. |
| 5,503,846 A | 4/1996 | Wehling et al. |
| 5,508,042 A | 4/1996 | Oshlack et al. |
| 5,549,912 A | 8/1996 | Oshlack et al. |
| 5,580,578 A | 12/1996 | Oshlack et al. |
| 5,593,694 A | 1/1997 | Hayashida et al. |
| 5,614,218 A | 3/1997 | Olsson et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |

(Continued)

FOREIGN PATENT DOCUMENTS

| | | |
|---|---|---|
| EP | 0311582 | 4/1989 |
| EP | 1419766 | 5/2004 |
| EP | 1504757 | 2/2005 |
| EP | 1782834 | 5/2007 |
| WO | WO9939698 | 8/1999 |

(Continued)

OTHER PUBLICATIONS

Portenoy et al. "Fentanyl Buccal Tablet (FBT) for Relief of Breakthrough Pain in Opioid-Treated Patients with Chronic Low Back Pain: A Randomized, Placebo-Controlled Study", ASRA 06, Final Abstract, Submitted Aug. 4.

(Continued)

*Primary Examiner* — Jennifer A Berrios

(57) ABSTRACT

A pharmaceutical composition may include a coated particulate which may include at least one active pharmaceutical ingredient, particularly one susceptible to abuse by an individual. The coated particles may include a fat/wax and have improved controlled release and/or crush resistance. Method of making these coated particulate and dosage forms therewith are also described.

14 Claims, 47 Drawing Sheets

(56) References Cited

U.S. PATENT DOCUMENTS

| | | |
|---|---|---|
| 5,731,006 A | 3/1998 | Akiyama et al. |
| 5,744,166 A | 4/1998 | Illum et al. |
| 5,811,126 A | 9/1998 | Krishnamurthy et al. |
| 5,840,754 A | 11/1998 | Guittard et al. |
| 5,849,240 A | 12/1998 | Miller et al. |
| 5,851,555 A | 12/1998 | Sanghvi et al. |
| 5,858,412 A | 1/1999 | Staniforth et al. |
| 5,891,471 A | 4/1999 | Miller et al. |
| 5,904,927 A | 5/1999 | Amiji |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 5,968,661 A | 10/1999 | Saito et al. |
| 6,024,981 A | 2/2000 | Khankari et al. |
| 6,033,686 A | 3/2000 | Seth |
| 6,039,980 A | 3/2000 | Baichwal |
| 6,103,219 A | 8/2000 | Sherwood et al. |
| 6,103,261 A | 8/2000 | Chasin et al. |
| 6,129,933 A | 10/2000 | Oshlack et al. |
| 6,143,322 A | 11/2000 | Sackler et al. |
| 6,143,353 A | 11/2000 | Oshlack et al. |
| 6,155,423 A | 12/2000 | Katzner et al. |
| 6,159,501 A | 12/2000 | Skinhoj et al. |
| 6,162,467 A | 12/2000 | Miller et al. |
| 6,194,005 B1 | 2/2001 | Farah et al. |
| 6,200,604 B1 | 3/2001 | Pather et al. |
| 6,228,398 B1 | 5/2001 | Devane et al. |
| 6,238,704 B1 | 5/2001 | Suzuki et al. |
| 6,245,351 B1 | 6/2001 | Nara et al. |
| 6,245,357 B1 | 6/2001 | Edgren et al. |
| 6,251,430 B1 | 6/2001 | Zhang et al. |
| 6,261,599 B1 | 7/2001 | Oshlack et al. |
| 6,290,990 B1 | 9/2001 | Grabowski et al. |
| 6,294,195 B1 | 9/2001 | Oshlack et al. |
| 6,309,668 B1 | 10/2001 | Bastin et al. |
| 6,316,031 B1 | 11/2001 | Oshlack et al. |
| 6,335,033 B2 | 1/2002 | Oshlack et al. |
| 6,368,625 B1 | 4/2002 | Siebert et al. |
| 6,375,987 B1 | 4/2002 | Farah et al. |
| 6,387,404 B2 | 5/2002 | Oshlack et al. |
| 6,399,096 B1 | 6/2002 | Miller et al. |
| 6,419,954 B1 | 7/2002 | Chu et al. |
| 6,500,459 B1 | 12/2002 | Chhabra et al. |
| 6,512,117 B1 | 1/2003 | Harclerode et al. |
| 6,534,091 B1 | 3/2003 | Garces Garces et al. |
| 6,572,885 B2 | 6/2003 | Oshlack et al. |
| 6,589,960 B2 | 7/2003 | Harclerode et al. |
| 6,602,522 B1 | 8/2003 | Chen et al. |
| 6,680,071 B1 | 1/2004 | Johnson et al. |
| 6,685,964 B1 | 2/2004 | Bartholomaeus et al. |
| 6,699,502 B1 | 3/2004 | Fanara et al. |
| 6,706,281 B2 | 3/2004 | Oshlack et al. |
| 6,730,321 B2 | 5/2004 | Ting et al. |
| 6,730,325 B2 | 5/2004 | Devane et al. |
| 6,733,783 B2 | 5/2004 | Oshlack et al. |
| 6,733,790 B1 | 5/2004 | Garces Garces et al. |
| 6,743,442 B2 | 6/2004 | Oshlack et al. |
| 6,753,014 B1 | 6/2004 | Sjoblom et al. |
| 6,759,059 B1 | 7/2004 | Pettersson et al. |
| 6,780,504 B2 | 8/2004 | Rupprecht et al. |
| 6,793,936 B2 | 9/2004 | Devane et al. |
| 6,863,901 B2 | 3/2005 | Hirsh et al. |
| 6,902,742 B2 | 6/2005 | Devane et al. |
| 6,905,709 B2 | 6/2005 | Oshlack et al. |
| 7,022,313 B2 | 4/2006 | O'Connor et al. |
| 7,090,867 B2 | 8/2006 | Odidi et al. |
| 7,201,920 B2 | 4/2007 | Kumar et al. |
| 7,387,792 B2 | 6/2008 | Hirsh et al. |
| 7,399,488 B2 | 7/2008 | Hirsh et al. |
| 7,510,726 B2 | 3/2009 | Kumar et al. |
| 7,514,100 B2 | 4/2009 | Oshlack et al. |
| 7,625,918 B2 | 12/2009 | Hagen et al. |
| 7,651,770 B2 | 1/2010 | Berkland et al. |
| 7,658,939 B2 | 2/2010 | Oshlack et al. |
| 7,776,314 B2 | 8/2010 | Bartholomäus et al. |
| 8,114,383 B2 | 2/2012 | Bartholomaus et al. |
| 8,187,636 B2 | 5/2012 | Soscia et al. |
| 8,192,722 B2 | 6/2012 | Arkenau-Maric et al. |
| 8,268,352 B2 | 9/2012 | Vaya et al. |
| 8,309,060 B2 | 11/2012 | Bartholomaus et al. |
| 8,349,362 B2 | 1/2013 | Soscia et al. |
| 8,361,499 B2 | 1/2013 | Oshlack et al. |
| 8,383,152 B2 | 2/2013 | Jans et al. |
| 8,409,616 B2 | 4/2013 | Kumar et al. |
| 8,410,129 B2 | 4/2013 | Brooks-Korn |
| 8,460,706 B2 | 6/2013 | Vergnault et al. |
| 8,507,001 B2 | 8/2013 | Shukla et al. |
| 8,551,520 B2 | 10/2013 | Oshlack et al. |
| 8,557,291 B2 | 10/2013 | Rariy et al. |
| 8,586,575 B1 | 11/2013 | King et al. |
| 8,597,681 B2 | 12/2013 | Park et al. |
| 8,623,412 B2 | 1/2014 | Farid et al. |
| 8,637,540 B2 | 1/2014 | Kumar et al. |
| 8,647,667 B2 | 2/2014 | Oshlack et al. |
| 8,647,669 B2 | 2/2014 | Soscia et al. |
| 8,653,106 B2 | 2/2014 | King et al. |
| 8,715,721 B2 | 5/2014 | Oshlack et al. |
| 8,765,178 B2 | 7/2014 | Parikh et al. |
| 8,808,740 B2 | 8/2014 | Huang |
| 8,895,063 B2 | 11/2014 | Guimberteau et al. |
| 8,933,092 B2 | 1/2015 | Holaday |
| 8,975,273 B2 | 3/2015 | Oshlack et al. |
| 8,980,291 B2 | 3/2015 | Oshlack et al. |
| 9,034,376 B2 | 5/2015 | Wright et al. |
| 2002/0006919 A1 | 1/2002 | Thosar et al. |
| 2002/0044966 A1 | 4/2002 | Bartholomaeus et al. |
| 2002/0110595 A1 | 8/2002 | Chang et al. |
| 2002/0110598 A1 | 8/2002 | Chung et al. |
| 2003/0049317 A1* | 3/2003 | Lindsay .................. 424/468 |
| 2003/0077297 A1 | 4/2003 | Chen et al. |
| 2003/0125347 A1 | 7/2003 | Anderson et al. |
| 2003/0180362 A1 | 9/2003 | Park et al. |
| 2003/0190358 A1 | 10/2003 | Oshlack et al. |
| 2004/0009219 A1 | 1/2004 | Odidi et al. |
| 2004/0013747 A1* | 1/2004 | Tucker et al. .................. 424/718 |
| 2004/0028735 A1 | 2/2004 | Kositprapa |
| 2004/0052844 A1 | 3/2004 | Hsiao et al. |
| 2004/0096499 A1 | 5/2004 | Vaya et al. |
| 2004/0096500 A1 | 5/2004 | Oshlack et al. |
| 2004/0105887 A1 | 6/2004 | Oshlack et al. |
| 2004/0121001 A1 | 6/2004 | Oshlack et al. |
| 2004/0131552 A1 | 7/2004 | Boehm |
| 2004/0142035 A1 | 7/2004 | Chang et al. |
| 2004/0151791 A1 | 8/2004 | Mayo-Alvarez et al. |
| 2004/0157784 A1 | 8/2004 | Chopdekar et al. |
| 2004/0170680 A1 | 9/2004 | Oshlack et al. |
| 2004/0185098 A1 | 9/2004 | Oshlack et al. |
| 2004/0208930 A1 | 10/2004 | Yoneda et al. |
| 2004/0208936 A1 | 10/2004 | Chorin et al. |
| 2004/0224017 A1 | 11/2004 | Mulye |
| 2004/0253310 A1 | 12/2004 | Fischer et al. |
| 2005/0020613 A1 | 1/2005 | Boehm et al. |
| 2005/0053656 A1 | 3/2005 | Ping |
| 2005/0074493 A1 | 4/2005 | Mehta et al. |
| 2005/0089568 A1 | 4/2005 | Oshlack et al. |
| 2005/0106249 A1 | 5/2005 | Hwang et al. |
| 2005/0163856 A1 | 7/2005 | Maloney et al. |
| 2005/0165038 A1 | 7/2005 | Gordon |
| 2005/0169989 A1 | 8/2005 | Moe et al. |
| 2005/0169990 A1 | 8/2005 | Kao et al. |
| 2005/0245483 A1 | 11/2005 | Brogmann et al. |
| 2005/0266072 A1 | 12/2005 | Oshlack et al. |
| 2006/0024361 A1 | 2/2006 | Odidi et al. |
| 2006/0104909 A1 | 5/2006 | Vaghefi et al. |
| 2006/0153915 A1 | 7/2006 | Park et al. |
| 2006/0153916 A1 | 7/2006 | Vaya et al. |
| 2006/0204573 A1 | 9/2006 | Mulye |
| 2006/0233879 A1 | 10/2006 | Lerner et al. |
| 2006/0233880 A1 | 10/2006 | Lerner et al. |
| 2006/0251721 A1 | 11/2006 | Cruz et al. |
| 2006/0263429 A1 | 11/2006 | Feng |
| 2006/0269604 A1 | 11/2006 | Sackler et al. |

(56) References Cited

U.S. PATENT DOCUMENTS

| | | |
|---|---|---|
| 2007/0003616 A1 | 1/2007 | Arkenau-Maric et al. |
| 2007/0003617 A1 | 1/2007 | Fischer et al. |
| 2007/0009589 A1 | 1/2007 | Raghupathi et al. |
| 2007/0020335 A1 | 1/2007 | Chen et al. |
| 2007/0104788 A1 | 5/2007 | Mulligan |
| 2007/0190142 A1 | 8/2007 | Breitenbach et al. |
| 2007/0203165 A1 | 8/2007 | Shafer et al. |
| 2007/0212414 A1 | 9/2007 | Baichwal et al. |
| 2007/0231268 A1 | 10/2007 | Emigh et al. |
| 2008/0069891 A1 | 3/2008 | Habib et al. |
| 2008/0311197 A1 | 12/2008 | Arkenau-Maric et al. |
| 2009/0004285 A1 | 1/2009 | Yu et al. |
| 2009/0238868 A1 | 9/2009 | Mehta |
| 2009/0297617 A1 | 12/2009 | Rariy et al. |
| 2009/0304793 A1 | 12/2009 | Boehm |
| 2009/0317355 A1 | 12/2009 | Roth et al. |
| 2010/0015223 A1 | 1/2010 | Cailly-Dufestel et al. |
| 2010/0098771 A1 | 4/2010 | Mehta |
| 2011/0002985 A1 | 1/2011 | Shah et al. |
| 2011/0123613 A1 | 5/2011 | Bhat et al. |
| 2011/0150990 A1 | 6/2011 | Shah et al. |
| 2011/0301129 A1 | 12/2011 | Berner et al. |
| 2012/0135071 A1 | 5/2012 | Bartholomaus et al. |
| 2012/0141583 A1 | 6/2012 | Mannion et al. |
| 2012/0172387 A1 | 7/2012 | Fleischer et al. |
| 2012/0202838 A1 | 8/2012 | Ghosh et al. |
| 2012/0251637 A1 | 10/2012 | Bartholomaus et al. |
| 2012/0308654 A1 | 12/2012 | Bartholomaus et al. |
| 2012/0321674 A1 | 12/2012 | Vachon et al. |
| 2012/0321716 A1 | 12/2012 | Vachon et al. |
| 2013/0028970 A1 | 1/2013 | Schwier et al. |
| 2013/0045960 A1 | 2/2013 | Hirsh et al. |
| 2013/0116327 A1 | 5/2013 | Kinter et al. |
| 2013/0195935 A1 | 8/2013 | Bartholomaus et al. |
| 2013/0217716 A1 | 8/2013 | Wright et al. |
| 2013/0217777 A1 | 8/2013 | Kirkorian |
| 2013/0251759 A1 | 9/2013 | Jans et al. |
| 2013/0261143 A1 | 10/2013 | Wright et al. |
| 2013/0280338 A1 | 10/2013 | Wening et al. |
| 2013/0320592 A1 | 12/2013 | Arkenau-Maric et al. |
| 2014/0011832 A1 | 1/2014 | Huang |
| 2014/0072644 A1 | 3/2014 | Guimberteau et al. |
| 2014/0079780 A1 | 3/2014 | Arkenau Maric et al. |
| 2014/0080858 A1 | 3/2014 | Bartholomaus et al. |
| 2014/0080915 A1 | 3/2014 | Bartholomaus et al. |
| 2014/0093559 A1 | 4/2014 | Bartholomaus et al. |
| 2014/0105830 A1 | 4/2014 | Bartholomaus et al. |
| 2014/0105987 A1 | 4/2014 | Rariy et al. |
| 2014/0112980 A1 | 4/2014 | Vaghefi et al. |
| 2014/0154313 A1 | 6/2014 | Counts et al. |
| 2014/0199394 A1 | 7/2014 | Oshlack et al. |
| 2014/0220127 A1 | 8/2014 | Herry et al. |
| 2014/0271896 A1 | 9/2014 | Abu Shmeis et al. |
| 2014/0271898 A1 | 9/2014 | Shah et al. |
| 2014/0275038 A1 | 9/2014 | Shah et al. |
| 2014/0275039 A1 | 9/2014 | Shah et al. |
| 2014/0275149 A1 | 9/2014 | Shah et al. |
| 2014/0294980 A1 | 10/2014 | Berkland et al. |
| 2014/0322323 A1 | 10/2014 | Jans et al. |
| 2014/0341984 A1 | 11/2014 | Shmeis et al. |
| 2014/0348936 A1 | 11/2014 | Reyes et al. |
| 2014/0356426 A1 | 12/2014 | Barnscheid et al. |
| 2014/0363516 A1 | 12/2014 | Rother et al. |
| 2015/0004244 A1 | 1/2015 | Rariy et al. |
| 2015/0005332 A1 | 1/2015 | Rariy et al. |
| 2015/0005333 A1 | 1/2015 | Wright et al. |
| 2015/0037427 A1 | 2/2015 | Benita et al. |
| 2015/0045383 A1 | 2/2015 | Hartman et al. |

FOREIGN PATENT DOCUMENTS

| | | |
|---|---|---|
| WO | WO0236099 | 5/2002 |
| WO | WO02092059 | 11/2002 |
| WO | WO2004026256 | 4/2004 |
| WO | WO2004026262 | 4/2004 |
| WO | WO2004064807 | 8/2004 |
| WO | WO2004084865 | 10/2004 |
| WO | WO2004093819 | 11/2004 |
| WO | WO2004108117 | 12/2004 |
| WO | WO2005034930 | 4/2005 |
| WO | WO2005099674 | 10/2005 |
| WO | WO2006002884 | 1/2006 |
| WO | WO2007048233 | 5/2007 |
| WO | WO2007103293 | 9/2007 |
| WO | WO2007112574 | 10/2007 |
| WO | WO2008140460 | 11/2008 |
| WO | WO2009036812 | 3/2009 |
| WO | WO2009059701 | 5/2009 |
| WO | WO 2010020856 | 2/2010 |
| WO | WO2010033195 | 3/2010 |
| WO | WO 2012052955 | 4/2012 |
| WO | WO 2012112952 | 8/2012 |
| WO | WO 2013017234 | 2/2013 |
| WO | WO 2013042125 | 3/2013 |
| WO | WO 2013156453 | 10/2013 |
| WO | WO 2014144027 | 9/2014 |
| WO | WO 2014146093 | 9/2014 |

OTHER PUBLICATIONS

Portenoy et al. "Fentanyl Buccal Tablet (FBT) for Relief of Breakthrough Pain in Opioid-Treated Patients with Chronic Low Back Pain", Current Medical Research and Opinion, vol. 23(7), pp. 223-233, 2007.

Physician's Desk Reference 57th ed. 2003 p. 1184 (package insert information for ACTIQ).

Brendenberg "New Concepts in Administration of Drugs in Tablet Form: Formulation and Evaluation of a Sublingual Tablet for Rapid Absorption and Presentation of an Individualized Dose Administration System Acta Universitiatis Upsaliensis." *Comprehensive Summaries of Uppsala Dissertations from the Faculty of Pharmacy* 287 83 pp. Uppsala ISBN 91-554-5600-6 (2003).

Frohof-Hulsmann et al., "Aqueous Ethyl Cellulose Dispersion Containing Plasticizers of Different Water Solubility and Hydroxypropyl Methyl-Cellulose as Coating Material for Diffusion Pellets II: Properties of Sprayed Films", European Journ. of Pharma and Biopharma., Vo. 48, pp. 67-75, 1999.

Hyppola et al.,"Evaluation of Physical Properties of Plasticized Ethyl Cellulose Films Cast From Ethanol Solution Part I", International Journ. of Pharma., vol. 133, pp. 161-170, 1996.

International Search Report for PCT/US2007/020041, dated Feb. 25, 2008.

Vashi et al., "Clinical Pharmacology and Pharmacokinetics of Once-Daily Hydromorphone Hydrochloride Extended-Release Capsules", J. Clin. Pharmacol., vol. 45, pp. 547-554, 2005.

Webster, "PTI-821: Sustained-Release Oxycodone Using Gel-Cap Technology", Expert Opin. Investig. Drugs, vol. 16(3), pp. 1-8, 2007.

Gustafsson et al., "Characterisation of Particle Properties and Compaction Behaviour of Hydroxypropyl Methylcellulose with Different Degrees of Methoxyl/Hydroxypropl Substitution", EP J. of Pharmaceutical Sci. 9, pp. 171-184, 1999.

Siepmann et al., "A New Model Describing the Swelling and Drug Release Kinetics from Hydroxypropyl Methylcellulose Tablets", J. of Pharmaceutical Sci., vol. 88, No. 1, pp. 65-72, Jan. 1999.

Viriden et al., "Investigation of Critical Polymer Properties for Polymer Release and Swelling of HPMC Matrix Tablets", EP J. Pharmaceutical Sci., 36, pp. 297-309, 2009.

Sung et al., "Effect of Formulation Variables on Drug and Polymer Release from HPMC-Based Matrix Tablets", Int'l J. of Pharmaceutics, vol. 142, pp. 53-60, 1996.

\* cited by examiner

ABUSE RESISTANT DRUG FORMULATION

CROSS-REFERENCE TO RELATED APPLICATIONS

This application is a continuation of U.S. patent application Ser. No. 13/728,801, filed Dec. 27, 2012, which is a continuation of U.S. patent application Ser. No. 12/075,543, filed Mar. 12, 2008, now U.S. Pat. No. 8,445,018 (issued May 21, 2013), which is a continuation-in-part of U.S. patent application Ser. No. 11/900,851 filed Sep. 13, 2007, now abandoned, which claims benefit of U.S. provisional patent application Nos. 60/845,128 filed Sep. 15, 2006, 60/845,127 filed Sep. 15, 2006, 60/845,126 filed Sep. 15, 2006, 60/845,151 filed Sep. 15, 2006, and 60/850,456 filed Oct. 10, 2006, the disclosures of which are hereby incorporated herein by reference.

BACKGROUND OF THE INVENTION

Certain drugs (referred to herein as Active Pharmaceutical Ingredients or "API") such as, for example, the opioid oxycodone, are administered to patients to reduce pain. Successful pain management in many of these patients requires maintenance of certain blood levels of the opioid throughout the day. One way of obtaining acceptable blood levels, used commonly in the pharmaceutical industry, is providing a dose which contains far more drug than is necessary to obtain the desired blood level. Blood levels shortly after the tablet is ingested reach a maximum or $C_{max}$ in a relatively short time, often within hours of ingestion ($T_{max}$) and thereafter, as the body uses, processes and excretes drug from the blood system, the blood level drops. If the $C_{max}$ attained is sufficiently high, and the body's clearance of the drug is sufficiently slow, the blood levels may not fall to subtherapeutic levels for 4-12 hours or even longer. However, with drugs like oxycodone and indeed for many other drugs, this is an impractical and inefficient dosing system. In addition, there is a risk to the patient in that such high initial API levels can cause significant side effects.

Another method of administering drugs involves the use of an extended release mechanism. An extended release can be achieved in many different ways and there are many different release profiles that can be attained. For exemplification only, a granulate material can be produced with a material that when exposed to the digestive tract, swells with available fluids and either slowly erodes or slows the wetting and diffusion of API drug materials contained within the granulate, thus providing a much lower $C_{max}$ and often a much longer $T_{max}$. Ideally, a zero order release is obtained whereby a constant release rate and a constant blood level is attained throughout an extended period of time often six hours or more, more preferably twelve hours or more, and most preferably over about 24 hours. Not only could this strategy reduce the number of doses that need to be taken in a day, it also may prevent one from being exposed to the side effects which can come from unnecessarily high initial blood levels.

Those who seek to abuse these types of products to "get high" can be frustrated by such extended and indeed other controlled release strategies. These strategies actively prevent one from obtaining high blood levels of the drug which can cause the euphoria or other physiologic effects which they are actually seeking, but which normal patients would consider an undesirable or even dangerous side effect. Such prescription drug abusers have learned to circumvent controlled release mechanisms by various administrative abuse means including simply chewing extended release tablets or crushing them using a mortar and a pestle for injection or the like. This can cause the rupture or otherwise compromise the API particle and/or controlled release coating, exposing more of the API to digestion and absorption more quickly, allowing the abuser to achieve much higher blood levels.

Such abuse can have rather far ranging consequences. First, it facilitates drug abuse by individuals which can lead to significant health consequences and even death for the abuser. The consequences of such abuse reach far beyond the abuser and his or her immediate family. Indeed, they can be societal as well. Useful drugs necessary for cancer patients, patients with post-operative or pre-operative pain, chronic pains from arthritis or back injuries need to have available products to allow them to cope. However, the potential for abuse is a constant concern to regulators and law enforcement as these often prescription drugs may be more freely obtainable than truly illegal illicit substances. There are also the societal problems relating to drug use, which includes the cost of their health care, the cost of their rehabilitation, the increase in crime which may come from supporting their drug habit and the like.

Ways of making a dosage form more crush resistant/abuse resistant include those disclosed in U.S. Patent App. Pub. No. 2006/0104909 and 2006/0193914. Coating pharmaceuticals or particles with various materials, which may include a fat/wax, to achieve other objectives, such as taste-masking, extended release, easier swallowing, etc. are also known. See, for example, U.S. Pat. Nos. 5,178,878; 5,607,697; 6,024,981; 6,280,770; 6,368,625; 6,692,771; 6,740,341; 2003/0180362; 2005/0163839; and 2007/0003617. See also U.S. Pat. No. 6,740,341, which discloses, inter alia, granulates coated with a dual layer coating one of which can include ethyl cellulose and HPMC.

Another way to circumvent controlled release coatings is to attempt to dissolve the dosage form in a solvent such as water or ethanol. The latter can be particularly dangerous as many prescription drugs should not be taken with alcohol. Depending upon the coating material used, the ethanol or water may act as a solvent, dissolving or eroding the coating and circumventing the intended controlled release. The resulting material can then be administered generally, orally, or in a syringe by a drug abuser.

There are several techniques which have been developed to deter this type of solvent abuse. One abuse deterrent system for oral opioid compounds is described in U.S. Published Application No. 2006/0177380. This disclosure describes a composition containing a gel forming polymer forming an obstacle to syringe uptake, and nasal/mucosal irritant that causes discomfort when excessive amounts of the active compound are inhaled. Such abuse-deterring systems often are designed for the nasal or parenteral abuse routes. See also U.S. Patent Application Publication Nos. 2006/0193914, 2006/0188447, 2006/0193782, 2006/0204573, 2002/0110595, WO 2006/079550, WO 2007/087452A2, U.S. Pat. Nos. 6,607,751 and 7,090,867. Uses of fax/waxes more generally are also described in US 2004/0116352. U.S. Pat. No. 5,500,227 discloses, the use of, inter alia, waxes and fatty alcohols in a coating to provide sustained release.

SUMMARY OF THE INVENTION

In one embodiment, the present invention comprises a particle which is coated and which provides advantages in terms of a controlled release of any active pharmaceutical ingredient ("API") contained therein or abuse resistance and, in particular, resistance to crushing. This is accomplished, at least in part, by the addition of a fat/wax to the particle, to the coating, or both.

In another embodiment, a particle of the invention containing a fat/wax in the core, in the coating, or both, is blended with and in other aspects, formulated into a dosage form with, other particles of fat/wax which may be the same or different. Not only can these pharmaceutical compositions and dosage forms produced therefrom provide benefits in terms of controlled release and/or crush resistance, they also may provide, in certain instances, solvent resistance thereby providing an abuse resistant, controlled release dosage form with reduced exposure to abuse by exposure to solvents and/or physical forces such as crushing.

In another embodiment, the present invention includes coated particles comprising: controlled release API-containing particles comprising an API in an amount of at least about 0.1%, and a fat/wax in an amount of between about 5 and about 40% based on the weight of the particles, and a crush resistant coating containing between about 5 and about 30% of a fat/wax based on the weight of the coated particles. In some aspects of this embodiment, the coating is present in an amount of between about 20 and about 75% by weight based on the weight of the coated particles. The coated particles of this embodiment exhibit at least one of greater crush resistance or longer API release when compared to identical coated particles that do not include a fat/wax in both the particle and the coating.

In other aspects of this embodiment, the coated particles are wet granulates comprising an API in an amount of between about 0.1 to about 90 percent by weight of the granulate. In some aspects of this embodiment, the API is granulated with a first material that is at most slightly soluble in water but is at least slightly soluble in alcohol and is present in an amount between about 1 to about 90 percent by weight of the granulate. In addition to or instead of the first material just described, the API can be granulated with a second material that is at most slightly soluble in alcohol but at least slightly soluble in water and is present in an amount between about 1 and about 90 percent by weight of the granulate. When the particle is a wet granulate, it is preferably granulated in the presence of water and alcohol. In one aspect, the first material is ethylcellulose and the second material is HPMC.

The coating on the particles further comprises a material selected from the group consisting of cellulose polymers, methacrylate ester copolymers, methacrylic acid copolymers and shellac, said coating material deposited on the particles using an alcohol based solvent. In one embodiment, this coating material is ethylcellulose and the coating is deposited on the particle using substantially anhydrous ethanol. In some embodiments, at least one of the particles and coated particles is cured. Preferred APIs are opiates with fentanyl, oxycodone and hydromorphone, and salts thereof being particularly preferred.

In another embodiment, the present invention contemplates a pharmaceutical composition comprising: a matrix including particles of a fat/wax in an amount of between about 5 and about 40% by weight of the composition and any of the API-containing particles described above. In some instances, the use of these fat/waxes in the matrix may provide solvent resistance, and may also affect release rate and/or crushing.

These compositions may include a pharmaceutical dosage forms comprising: a matrix including particles of a fat/wax selected from the group consisting of waxes, fatty acids and fatty acid esters present in an amount of between about 5 and about 30% by weight of the dosage form and an amount of API-containing particles sufficient to provide an effective amount of the API. The API-containing particles, in some aspects, comprise an API and a fat/wax. In some aspects of this embodiment, the fat/wax is selected from the group consisting of waxes, fatty acids and fatty acid esters and is present in an amount of between about 5 and about 40% based on the weight of the API-containing particles. In some aspects of this embodiment, the present invention includes a crush resistant coating containing between about 5 and about 40% of a fat/wax. In some further aspects, the fat/wax is selected from the group consisting of waxes, fatty acids and fatty acid esters, based on the weight of the coated particles, and the coating is present in an amount of between about 20 and about 75% by weight of the coated particles. One or more excipients or additional ingredients may also be present in the dosage form.

In some aspects of this embodiment, the dosage form further comprises a first material that is at most slightly soluble in water but is at least slightly soluble in alcohol and is present in an amount between about 1 to about 90 percent by weight of the particle. In still other aspects, it comprises a second material that is at most slightly soluble in alcohol but at least slightly soluble in water present in an amount between about 1 and about 90 percent by weight of the particle. When the particle is a wet granulate comprising the API, the first and the second material, it is often granulated with a solvent system of water and alcohol. In some aspects of this embodiment, the coating further comprises a coating material selected from the group consisting of cellulose polymers, methacrylate ester copolymers, methacrylic acid copolymers and shellac, said coating material deposited on the granulate using an alcohol based solvent. Again, in some aspects, the coated particles are present in the dosage form in an amount sufficient to provide of between about 10 micrograms and about 2000 milligrams of API per dosage form, more preferably 10 micrograms to 1000 milligrams.

In one aspect, the first material is ethylcellulose and the second material is HPMC. In another, the coating material is ethylcellulose and the coating is deposited on the particle using substantially anhydrous ethanol. The particles and/or the coated particles may be cured.

Another embodiment of the invention is a method of producing a dosage form providing longer release and enhanced crush resistance release dosage form comprising: granulating, in the presence of water and alcohol, an API with a first material that is at most slightly soluble in water but is at least slightly soluble in alcohol. In some aspects, this first material is present in an amount between about 1 to about 90 percent by weight of the granulate. Granulation may instead, or in addition, include a second material that is at most slightly soluble in alcohol but at least slightly soluble in water. In some aspects, this second material is present in an amount between about 1 and about 90 percent by weight of the granulate. The granulate may, in some embodiments, also includes a fat/wax present in an amount of about 5 and about 40% based on the weight of the granulate. After granulation and optional drying and/or curing, the granulate is coated with a coating comprising a material selected from the group consisting of cellulose polymers, methacrylate ester copolymers, methacrylic acid copolymers and shellac, said coating material deposited on said granulate using an alcohol based solvent and, in some embodiments, further comprising a fat/wax in an amount of between about 5 and about 40% based on the weight of the coated granulate. The coating is provided in an amount of between about 20% and about 75% by weight base on the weight of the coated particle. This coated granulate may optionally be dried and/or cured. The coated granulate is next mixed with at least one excipient to form a blend; and individual dosage forms are formed from the blend. This can include packets of the coated particles, capsules filled with particles, or tablets compressed using the coated granulate particles. In some embodiments, the fat/wax is added to said granulate and/or in a solid, non-molten form.

Another embodiment of the invention is a method wherein the blend includes particles of fat/wax. In some embodiments, these additional fat/wax particles are provided in an amount which is sufficient to provide at least one of additional crush resistance, longer release of the API or additional solvent resistance. The fat/wax is often selected from the group consisting of waxes, fatty acids and fatty acid esters.

DETAILED DESCRIPTION

Figure 1:
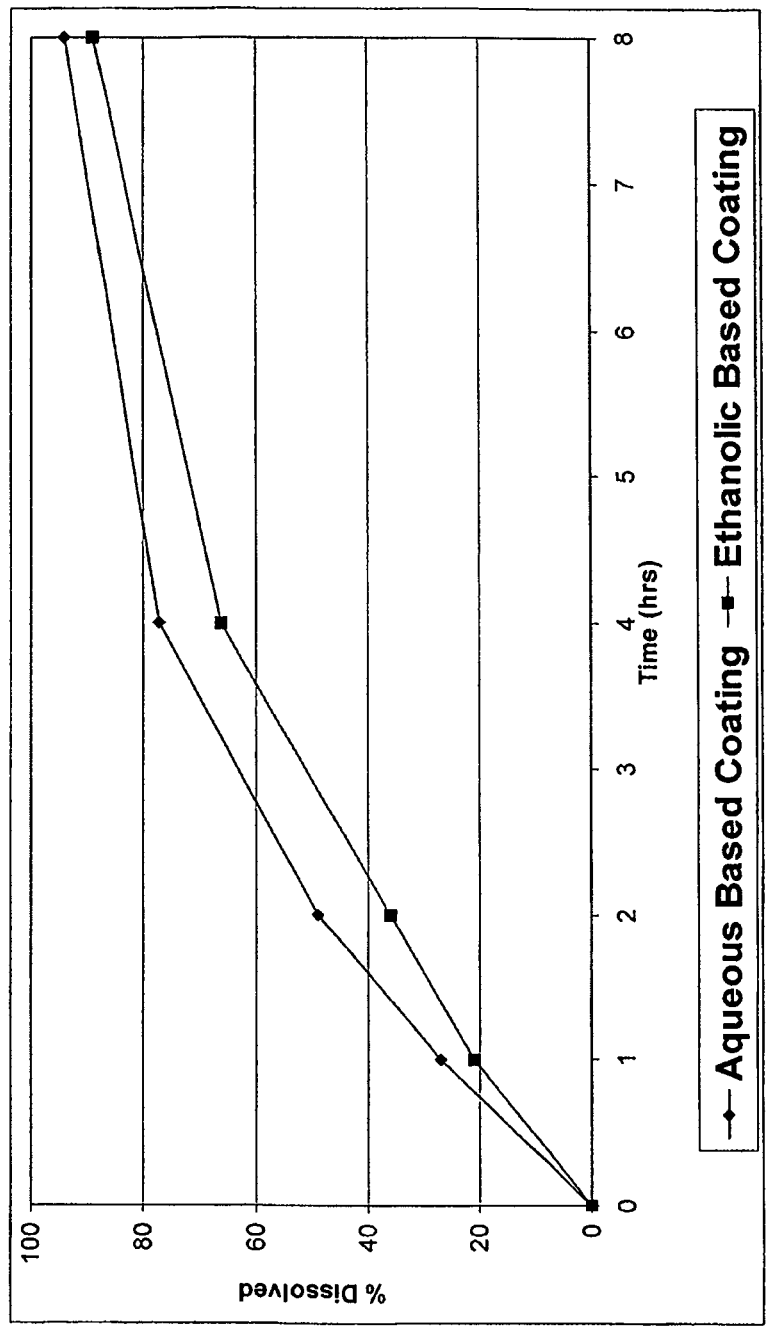
FIG. 1 illustrates comparative dissolution results for granules coated with and without a crush resistant coating in accordance with Examples 1 and 2 of the present invention.

While the specification concludes with the claims particularly pointing and distinctly claiming the invention, it is believed that the present invention will be better understood from the following description. All percentages and ratios used herein are by weight of the total dosage form, or coated particle, as the context requires, unless otherwise designated. All measurements made are at 25° C. and normal pressure unless otherwise designated. All temperatures are in Degrees Celsius unless specified otherwise. The present invention can comprise or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Note that while the specification and claims may refer to a tablet or other dosage form of the invention as, for example, containing particles having a certain particle size or distribution, or a certain type of, for example, nondirect compression sugar, it may be difficult to tell from the final dosage form that the recitation is satisfied. However, such a recitation may be satisfied if the materials used prior to final blending and tablet formulation, for example, meet that recitation. In another example, while it might be difficult to know the weight gain of a coated active pharmaceutical ingredient ("API")-containing granule as it actually exists in a finished tablet, if it is determined that the coated API-containing granule used to make the tablet, prior to a final blending and compression step, did exhibit the desired coating level, that is sufficient. Indeed, as to any property of a dosage form which cannot be ascertained from the dosage form directly, it is sufficient if that property resides in the formulation just prior to producing a dosage form therefrom.

In one embodiment, the present invention embraces coated particles wherein one of the particles or the coating comprises a fat/wax. It has been discovered that the presence of the fat/wax within the coating or the particles provide enhanced pharmaceutical delivery properties and, in particular, extending the release time an API and/or providing additional crush resistance. This is compared to an otherwise identically constructed coated particle not containing the fat/wax as described herein.

In another embodiment, coated particles in accordance with the present invention may include a fat/wax in both the particle and the coating. In this embodiment, the coated particles will exhibit at least one of enhanced crush resistance or longer API release when compared to an identical coated particle that does not include a fat/wax in both the particle and the coating. In another embodiment, the present invention may be a particle which is a granulate, comprising at least one API, particularly one susceptible to abuse by an individual, in an amount between about 0.1 to about 90 percent by weight of the granulate. This API is granulated with at least one material, the API and the at least one material being granulated in the presence of a water and alcohol mixed solvent system. In still another embodiment, the particle is granulated of API and two discrete materials with different solubility behavior in water and alcohol. These granulates may also include a fat/wax.

The term "particle" is meant to be interpreted broadly so as to include, without limitation, powders, crystals, amorphous solid, cores, granules, microcrystals, microganuals, microparticles, minitablets, and the like.

The term "coating" is meant to encompass a material which substantially surrounds the particles and provides some additional function, such as, without limitation, taste masking, storage stability, reduced reactivity, controlled release, and/or abuse resistance. The term "controlled release" encompasses both an extended release which extends/or patterns the release of an API over time, as well as a delayed release such as enteric release. Controlled release, or "CR" coated particles, in one embodiment, extends the release of the API over a period of release from a normal immediate release dosage form to about 6 hours or more, more preferably 12 to about 24 hours or more. Preferred delayed release coated particles include preventing the release until the dosage form or coated particles enter the intestines.

"Abuse resistance" in the context of the invention generally refers to reducing the amount of API which would be released prematurely after application of either physical forces (crushing, for example) or solvent.

Particles can be composed of the API alone, the API coated onto a sphere or nonpareil, a mixture of nondrug/API particles, or a wet or dry granulate. These particles may include a fat/wax as described herein. In a preferred embodiment, the API-containing particle is a wet granulate that aids in providing crush resistance, controlled release or both. A wet granulate is an agglomerate formed by wet granulation, which is a process by which particles, often smaller particles, are bound together in a granulator.

When the API is used as the particle per se then it comprises 100% by weight of the particles. When the particle is a mixture, is coated onto a core, or is a granulate, the API generally constitutes about between about 0.1% and about 90% by weight of the particles. This weight is based on the dried weight of the particles. For a specific example, the API can be between about 0.1 and about 90% by weight of the granulate with the balance being binders, other particles, granulating excipients, and the like. In another embodiment, the API is present in an amount of between about 1 and about 80, more preferably between about 20 and about 60% by weight of the particles. This is based on the uncoated granules formulation, not the coated particles.

When the particles are wet granulated, they can be formed using any solvent and/or binder which can be added separately or together. However, it has been discovered that crush resistance can be obtained or augmented by using certain binders applied and/or granulated with a solvent system of water and alcohol. In one embodiment, the amount of water in the solvent mixture ranges from about 5 to about 50 percent by weight, more preferably from about 10 to about 40 percent by weight, and most preferably between about 20 to about 30 percent by weight of the solvent. Any alcohol as defined herein may be used, but $C_1$-$C_6$ linear alcohols are preferred and most preferred is ethanol.

Alcohol or alcohol based solvents in accordance with the present invention generally means that the material includes at least about 90% of a $C_1$-$C_7$ alcohol more preferably $C_2$-$C_6$ alcohol and at most about 10% water by volume. More preferably, the alcohol is ethanol which is at least about 95% alcohol by volume with the balance being water. Absolute ethanol may also be used which contains greater than about 99% ethanol by volume.

In one embodiment, the granulate includes at least one other material, sometimes referred to as the "first material." In one embodiment, this first material is a polymer, which is at least slightly soluble, preferably, soluble in alcohol and at most slightly soluble in water. Generally this first material is selected from natural and synthetic starches, natural and synthetic celluloses, acrylics, vinylics and resins. More preferably, the first material is selected from ethylcellulose, Eudragit RS, RL, E, NE, L, S, and shellac. Most preferably, the first material is ethylcellulose This first material could be added as a solid, could be dissolved in the solvent, or could be added to the granulation process in both forms.

The granulate can also include a "second material" which is at least slightly soluble, preferably, soluble in water and at most slightly soluble in alcohol. This second material, like the first material, could be added as a solid, could be dissolved in the solvent, or could be added to the granulation process in both forms. One such second material is HPMC.

Other second materials may be selected from the same general categories as the first material; namely, natural and synthetic starches, natural and synthetic celluloses, acrylates, and polyalkylene oxides. Natural and synthetic celluloses are preferred for both the first and second slightly soluble materials. In a particularly preferred embodiment, the second material, which can also be called a second gelable material, is a modified celluloses such as hydroxypropymethylcellulose (HPMC), hydroxypropylcellulose (HPC) hydroxymethylcellulose (HMC), methylcellulose (MC), hydroxyethylcellulose (HEC), carboxymethylcellulose (CMC). However, the second material and are generally water soluble and generally insoluble in alcohols $C_1$-$C_6$ alcohols as discussed above.

As noted above, in some embodiments, the particle includes a first material that is at most "slightly soluble" in water but is at least slightly soluble in alcohol, and a second material that is at most "slightly soluble" in alcohol but is at least sparingly slightly in water, and an API. By "slightly soluble" it is meant that the material is generally soluble in one of the solvents requiring between about 100 and 1000 parts of solvent to solubilize a single part of the material in question. The material may be dissolvable or dispersible in larger volumes. Sparingly soluble means it requires 30-100 parts of solvent to dissolve one part of the solute. In another embodiment, however, the gap in solubility of the first and second materials between water and alcohol is greater. Thus, in one embodiment, the first material is only slightly soluble in water but it is at least sparingly soluble (more soluble than just slightly soluble) in alcohols. The reverse is true for the second material which remains only slightly soluble, at most, in alcohol, but is at least sparingly soluble in water.

In a particularly preferred embodiment, the first material is ethylcellulose. Ethylcellulose is an inert, hydrophobic polymer and is essentially tasteless, odorless, colorless, non-caloric, and physiologically inert. There are many types of ethylcellulose which can be used, as long as they meet the other requirements, such as alcohol solubility, discussed herein. The ethylcellulose used can have different ethoxy content such as 48.0-49.5% described as N-type; 49.6-51.5% described as T-type; 50.5-52.5% described as X-type; all available from Aqualon, Hercules Research center, Wilmington, Del.

The ethylcellulose used can have different molecular weights such as including EC polymers of the N-type that form 5% w/w solution in toluene:ethanol (80:20) that have viscosity ranges of 5.6-8.0 centipoise (cps) described as N7; 8.0-11 cps described as N10; 12-16 cps described as N14; 18-24 cps described as N22; 40-52 cps described as N50; 80-105 cps described as N100.

Finally, the ethylcellulose can include different degrees of substitution of ethoxy groups per anhydroglucose unit, such as 2.65-2.81 for the X-type. N-type has values of 2.46-2.58.

When HPMC is used in the granulate as the second material, the HPMC used can have different methyl to hydroxypropyl substitution percent ratios ranging from 30:0 in the A-type, 29:8.5 for the E-type, 28:5 in the F-type, 22:8 for the K-type all available from DOW Chemical Company, Midland, Mich. or any other HPMC polymers available from other suppliers such as Aqualon.

The HPMC used can have different molecular weights such as including HPMC polymers that form 2% w/w aqueous solution at 20° C. that have viscosity ranges of 15-4000 mPa·s for the A-type, 3-10,000 for the E-type, 50-4000 for the F-type and 3-100,000 for the K-type.

Before coating, the API containing particles preferably have an average particle size of about 100 to about 600 microns, and more preferably about 150 to about 500 microns, and most preferably about 200 to about 400 microns when tested by a sieve-shaking method. In another preferred embodiment, the pre-coated API containing particles preferably have a particle size distribution wherein no more than about 10% are less than 50 microns, and no more than 10% are larger than 700 microns. Of course, overs and unders could be discarded. These particle sizes are determined by a sieve shaking method based on weight.

Some of the particles in accordance with the present invention can provide abuse resistance in terms of crush resistance, solvent resistance, or both. One particularly preferred type of particle that accomplishes those goals is the API-containing granulate with ethylcellulose and HPMC granulated from a solvent system of water and ethanol as previously described.

Readily available solvents which can be utilized to dissolve dosage forms safely are few. Water is certainly one. Ethanol, while dangerous, is second. Other solvents may be available, but they are often inconvenient to obtain and/or can have debilitating, permanent side effects, which even an addict cannot ignore. For example, methanol or wood alcohol, is easy to find. However, it can cause blindness. This embodiment of the present invention utilizes two materials which, when exposed to a limited volume of alcohol, water, or a mixture thereof, forms a noninjectable mass ranging from an insoluble mass, to a gel, to a viscous slurry. It might also retard dissolution in these solvents.

By "limited volume" it will be appreciated that a small amount of a material that is, for example, at most slightly soluble in water (but at least slightly soluble in, for example, ethanol, such as ethylcellulose), could nonetheless be dissolved, dispersed or at least diluted sufficiently that it could not form a noninjectable mass, given enough solvent. Thus, for example, while a tablet in accordance with the present invention could, once dissolved, form insoluble mass, a gel, or otherwise raise the viscosity of 20 mL of water sufficiently to retard injection, it would do little to change the properties of, for example, one liter of water or more. Of course, it would be difficult in such circumstances to inject that liter into the body to obtain the desired "high."

The second material found within the granulate is a second slightly soluble material. This material is at most slightly soluble in alcohol but is at often soluble in the same volume of water. Like the first slightly soluble material, any material that is safe for ingestion or injection and can form a noninjectable mass under the specified condition is contemplated. The amount of the second slightly soluble material present in the granulate will depend on the same criteria as previously described in connection with the first gelable material.

Generally, a limited volume in accordance with the present invention is defined as 50 milliliters or less, more preferably 20 milliliters or less and even more preferably 10 milliliters or less and most preferably 5 milliliters or less (volumes which could be injected). Thus, the first slightly soluble material used in the dosage form must be of a type and available in an amount which is sufficient to allow it to form a noninjectable mass and the second slightly soluble material must be capable of doing the same when the dosage form containing both is dissolved (which includes partially dissolved or where an attempt is made to make it dissolve) in a limited volume of water, alcohol or both.

Generally, both the first material and the second material are provided within the granulate in an amount of between about 1% to about 90% by weight of the granulate, each, depending upon the desired properties, the API used, and the like. However, generally, the amount of first material in the granulate will range from between about 1 to about 90% by weight of the uncoated granulate. In another embodiment, the first material is present in an amount of from between about 5 to about 75% by weight of the granulate, and in yet another embodiment about 10 to about 40%. For the second material, in one embodiment it ranges from between about 10 to about 75% by weight of the granulate, and in another embodiment between about 15 to about 50% by weight of the granulate. In terms of all excipients (everything other than the API, the total amount in the uncoated particles can range from about 10 to about 99.9% by weight of the coated granulate. If stated as a percentage of the coated granulate, the amount generally ranges from between about 60% to about 90% by weight.

There are no specific particle size limitations with regard to the first or second slightly soluble materials in accordance with the present invention. However, the materials should be sufficiently small so as to enhance their ability to rapidly form a noninjectable mass.

As described above, the granulate comprises a first slightly soluble material and a second slightly soluble material. However, the granulate may include more than one material that is at most slightly soluble in water and is at least slightly soluble in alcohol and/or more than one second material that is at most slightly soluble in alcohol but is at least slightly soluble in water. In addition, a third or more slightly soluble material(s) may be added to provide a similar level of solvent abuse resistance as needed. Other conventional granulation excipients may also be present.

In addition to an API, the coated particles include a fat/wax which may, in some embodiments, be part of the particle instead of, or in addition to the coating. The fat/wax could be granulated with the API, with or without other additional ingredients. However, preferably, it is granulated with a first material and even more preferably a first and second material as described already herein. Of course, these materials could be merely mixed together and/or dry granulated together, or the particles and API could be embedded within or on discrete particles of fat/wax.

When present within the API-containing particles, the fat/wax generally makes up between about 5% to about 40% by weight of the particle, more preferably between about 5% to about 30% by weight of the uncoated particle. Those percentages may, however, vary depending upon the number of additional materials contained within the particle. Thus, for example, the fat/wax may make up a larger percentage by weight of the a granulate that uses only a first material and one which includes both, for example, ethylcellulose and HPMC.

The fat/wax preferably used in the particles (also referred to as cores) and coatings of the present invention, and indeed in the matrix or excipients in compositions and dosage forms, are hydrophobic and solid at room temperature (25° C.). Fats are fatty acid based compounds generally having a hydrophilic/lipophilic balance (HLB) of about 6 or less, more preferably 4 or less, and most preferably 2 or less, and also have a melting point which is preferably 30° C. or more, more preferably 40° C. and even more preferably 50° C. In one embodiment, the fat has an HLB of about 6 or less and a melting point of about 30° C. or more. In another embodiment, it has an HLB of about 4 or less and a melting point of about 40° C. or more. In another embodiment, the fat has an HLB of about 2 or less and a melting point of about 50° C. or more. Fats, including fatty acids and fatty esters in accordance with the present invention may be substituted or unsubstituted, saturated or unsaturated. However, generally they have a chain length of at least about 14. The esters in question may include fatty acid groups bound to alcohols, glycols, and in particularly preferred embodiment, glycerol. With regard to glyercols, for example, mono-, di-, and tri-fatty substituted glycerols are contemplated as are mixtures thereof. Thixotropic fats/waxes can also be used.

Suitable fat ingredients include, without limitation, glycerol fatty esters, fatty glyceride derivatives, waxes and fatty alcohols such as, for example, glycerol behenate (COMPRITOL®), glycerol palmitostearate (PRECIROL®), stearoyl macroglycerides (GELUCIRE®50/13). A particularly preferred material useful in accordance with the present invention is glycerol behenate.

Waxes are very complex and difficult to classify. See Kirk-Othmer, Encyclopedia of Chemical Technology (4th ed. 1998) Vol. 25 pp. 614-26, the text of which is incorporated by reference. They often meet the criteria described previously for fats (e.g., HLB of about 6 or less and melting point of 30° C. or more, HLB of about 4 or less and melting point of about 40° C. or more, HLB of about 2 or less and melting point of about 50° C. or more), but waxes that do not meet these criteria may also be used. Waxes include, without limitation, insect and animal waxes, vegetable waxes, mineral waxes, petroleum waxes, and synthetic waxes. Particularly preferred are beeswax, carnauba wax, condelilla wax, montan wax, ouricury wax, rice-bran wax, jojoba wax, microcrystalline wax, cetyl ester wax, anionic emulsifying wax, nonionic emulsifying wax and paraffin wax. In one embodiment, the fat/wax is a fatty acid ester of glycerol. In another, the fatty acid ester of glycerol is glycerol behenate.

Figure 46:
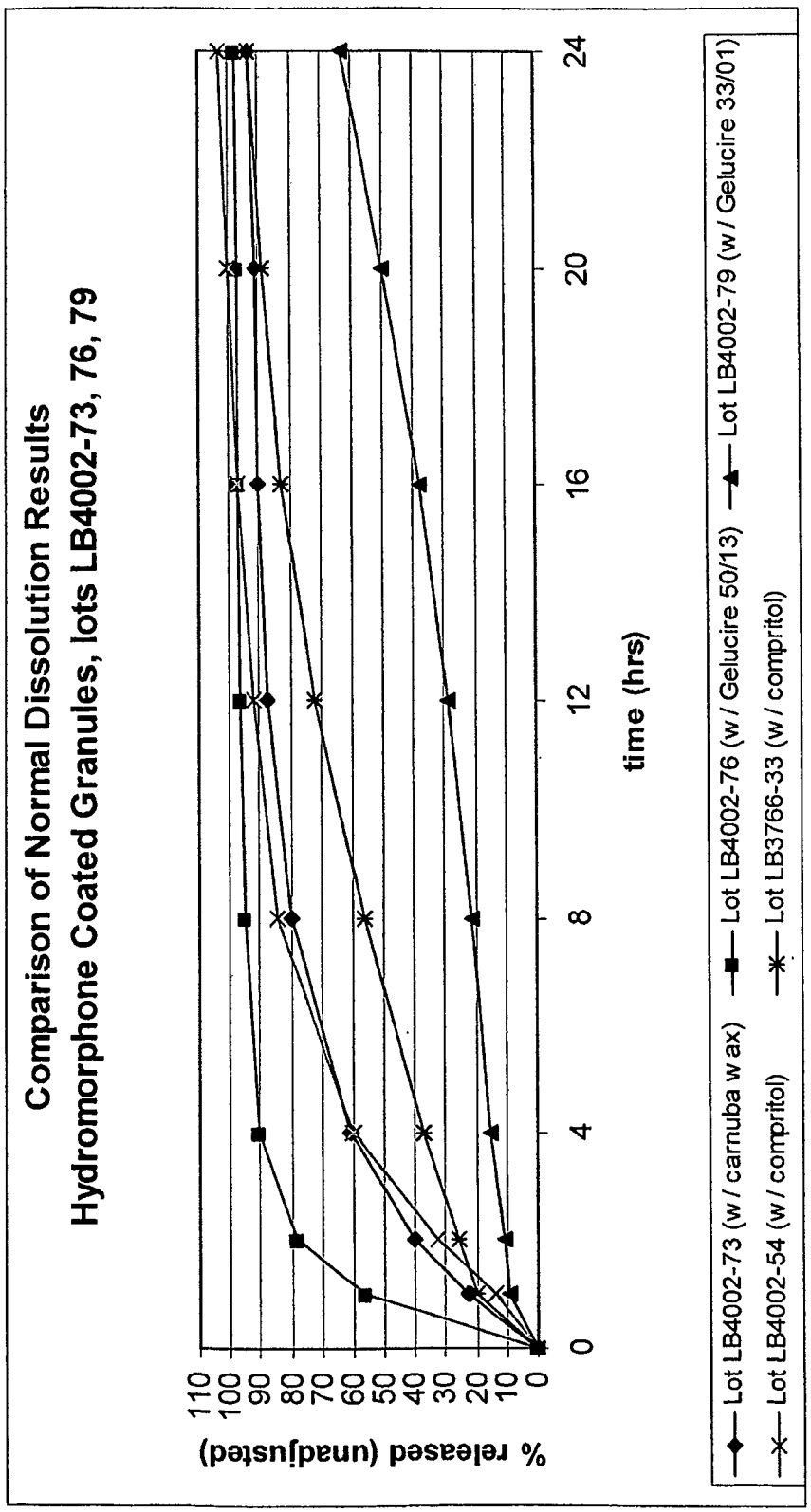
FIG. 46 illustrates the comparison of normal dissolution results on hydromorphone coated granules, lots LB4002-73, 76, 79 where the shaded diamonds represent lot LB4002-73 (with carnuba wax in core and coat, not cured), the x's represent lot LB4002-54 (with Compritol in core and coat, not cured), the shaded squares represent lot LB4002-76 (with gelucire 50/13 in core and coat, not cured), the *'s represent lot LB3766-33 (with Compritol in core not in coat, not cured) and the shaded triangles represent lot LB4002-79 (with gelucire 33/01 in core not in coat, not cured).
Figure 47:
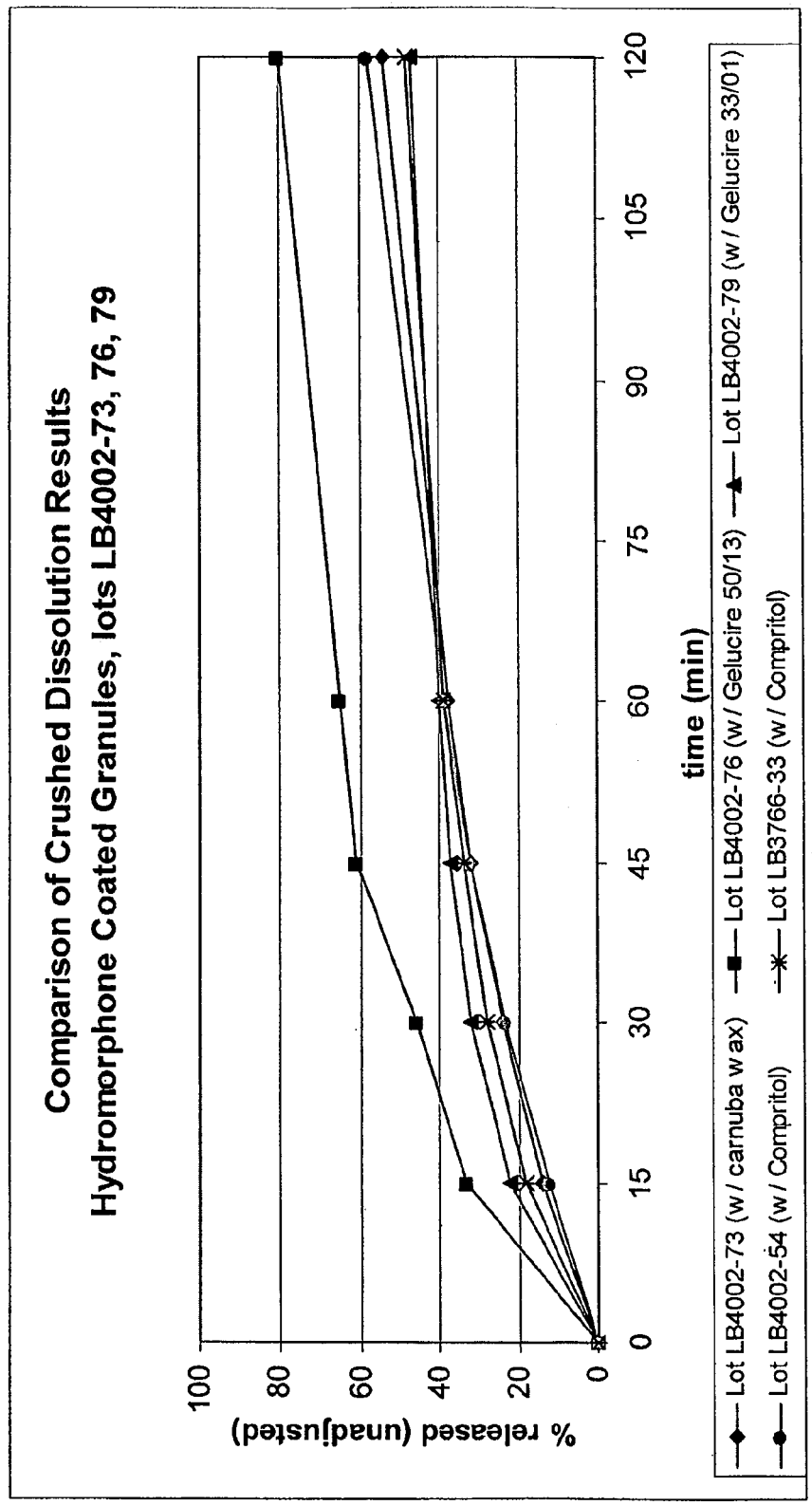
FIG. 47 illustrates the comparison of crushed dissolution results on hydromorphone coated granules, lots LB4002-73, 76, 79 where the shaded black diamonds represent lot LB4002-73 (with carnuba wax in core and coat, not cured), the x's represent lot LB4002-54 (with Compritol in core and coat, not cured), the shaded squares represent lot LB4002-76 (with gelucire 50/13 in core and coat, not cured), the *'s represent lot LB3766-33 (with Compritol in core not in coat, not cured) and the shaded triangles represent lot LB4002-79 (with gelucire 33/01 in core not in coat, not cured).

As illustrated in FIGS. 46 and 47, coated granules were prepared using different fat/waxes including carnuba wax (Strath and Pitsch, West Babylon, N.Y., lot#21293/07), Gelucire 50-13 and Gelucire 33-01 (both from Gattefosse, Paramus, N.J., Lot #s 106058 and 102590 respectively). Gelucire 50-13 has a melting range of around 50° C. and an HLB of 13. Gelucire 33-01 has a melting range of about 33° C. and an HLB of 1. The formulations tested were prepared in accordance with examples 8, 44, and 45. Note that Gelucire 50-13 was used in both the core and the coating whereas the Gelucire 33-01 particles used the fat/wax only in the core and not in the coating.

Reviewing the figures, it is clear that carnuba wax and Gelucire 33-01 performed well. Carnuba wax is a wax and Gelucire 33/01 is fatty acid esters of glycerol—a substituted fatty ester. Gelucire 50-13 provided inferior results. While it is a fatty ester derivative and has a desirable melting point of 50° C. or more, its HLB of 13 which makes it far too hydrophilic. As noted previously, not all fat materials which would structurally fall within the scope of the materials described will perform adequately. It has been found that only those with both a melting point of about 30° C. or more and an HLB of less than 6 will perform adequately. More preferably, the fat will have a melting point of about 40° C. or above, and an HLB of about 4 and below, and most preferably will have a melting point of about 50° C. or above and an HLB of about 2 and below. Compritol ATO 888 (generally used in the examples), for example, has a melting point of about 65° C. or above and an HLB of 2.

Gelucire 33-01, despite being very difficult to work with and being located only in the core, and carnuba wax, performed very well. Its generally lower melting point may make it more difficult to work with on a commercial scale. However, Gelucire 33-01 demonstrates that even materials with a melting point approaching the endpoints discussed herein may in fact provide successful particles and formulations.

More preferably, these materials are also listed in one or more compendia, meaning they have been recognized for use in oral pharmaceutical products.

Fat/waxes used in accordance with the present invention may be used in a molten form. However, it has been discovered that even when used as a generally solid, non-molten form such as relatively small particles at room temperature, they can provide some, if not all of the advantages as molten materials. Any usable particle size which allows for proper formation of the particles, coating or in the matrix and which provides the desired properties of the invention may be used. However, in one embodiment, for the compritol materials used in the examples, the average particle size ranged from between about 30 to about 60 microns with less than 10% larger than about 100 microns, all measured by volume using laser diffraction. However, a broader range is certainly contemplated thus particles having an average particle size between about 10 and about 100 microns are contemplated for the fat/wax as measured by laser diffraction. Carnuba wax used in the examples had a particle size of at least 65% passing through sieves with holes of 75 micron and at least 40% passing through sieves with holes of 44 micron. This would also meet the particle size range measured by laser diffraction.

In general, the binder used in granulation may be formed in situ (adding a solvent to a dry material that, when wetted, serves as a binder) or may be sprayed on or mixed with a solvent. In some instances, the solvent itself may serve as a binder. Moreover, one or more of the ingredients to be contained within the granulate can be introduced as part of the binder and/or as part of a solvent system. Thus, for example, the API could be dissolved, dispersed, suspended, or mixed with the solvent and/or with the binder and applied to the surface of the particulate of the first and/or second slightly soluble materials or some other component of the granulate. This is also true for the excipients described previously. The fat/wax, when present, is added as a dry particulate into the granulation. In the coating, it is dispersed in the coating solution.

Excipients which may be used in accordance with the present invention to form granulates include those which are traditionally used in oral dosage forms. In a preferred embodiment, the granulate may include any excipients as desired, which are then measured into a granulator.

It has been discovered that producing granulates in accordance with the present invention can provide advantages in terms of enhanced crush resistance and also provide adequate controlled release. However, in particular, by including a fat/wax in the particle/granulate as described herein it was unexpectedly found that one can attain further enhancements. For example, one may attain a further enhancement in the length of API release when compared to a similar particle produced without the fat/wax. As discussed in more detail herein, and as shown in Table 13, in one instance, otherwise identical formulations with and without compritol 888 (glyceryl behenate) in a tableted coated granulate were compared.

TABLE 13

Tablet Data
The table has been modified to reflect the exact data

| Tablet Lot # | Time of ≥90% release | Sim'd Oral Tampering (30 min) |
|---|---|---|
| LB3766-57 | 16 hr (90%) | 36% |
| LB3766-69 | 8 hr (96%) | NA |
| LB3766-70 | 20 hr (91%) | NA |
| LB3766-72 | 20 hr (93%) | 28% |
| LB3766-73 | 16 hrs (94%) | 64% |
| LB3766-87 | 16 (90%) | 38% |
| LB3766-88 55N | 16 hr (93%) | 52 |
| LB3766-88 74N | 16 hr (90%) | 50% |
| LB3766-89 | 8 hr (99%) | 51% |

The time necessary to obtain a release of greater than 90% was 8 hours (96%) in for the granulate without fat/wax. It was 16 hours (90%) for a compritol-containing granulate.

Therefore, in accordance with one aspect of the present invention, the fat/wax is selected of a type and used in an amount, in the particle, the core or both, such that the dosage form or coated particles provide at least a 10% increase in the length of time needed to achieve greater than 90% release of API contained within the particles when compared to an otherwise identical particulate without the fat/wax. If a granulate without a fat/wax released >90% after 14 hours, the granulate of the invention would release >90% after at least 15.4 hours. In another embodiment, the minimum increase is 25% and in yet still another embodiment, a 40% increase is realized.

Also, as illustrated in Table 13, the presence of a fat/wax in the core may provide advantages in terms of abuse resistance, in this instance due to the application of physical forces such as crushing force. Identical granules were produced with compritol and without compritol in the granulate, coated with a non-fat/wax-containing coating, and tableted. The granules prepared with compritol achieved a greater than 90% release in 20 hours (93%), whereas the granules without compritol only required 16 hours to reach a greater than 90% release (94%).

Tampering was simulated using a mortar and pestle as described herein and the release from those particles was measured, and was based on percent release of the API at 30 minutes. The granulate containing compritol ATO 888 released only 28% at 30 minutes, while the granulates without compritol ATO 888 released 63%. Thus, the use of a fat/wax in a coated particle, and in this case particles where the fat/wax was disposed only in the core, provided both better performance in terms of extended release properties and crush resistance.

During production of the particles, where solvent is used, it is not necessary that the material be actively dried in, for example, an oven, tray or other device. It may be left to air dry. The granulate can be coated after drying. When a coating is applied in a fluidized bed, the processes can go on nearly simultaneously. The coated particles are then mixed with at least one excipient as described herein and preferably compressed into tablets filled into capsules or measured into other dose based forms or packages.

The crush-resistance of these particles, coatings, coated particles and compositions of the invention can be measured by crushing a defined amount of coated API-containing particles (or a dosage form) with a mortar and pestle, placing the crushed materials in a solution, such as water, and assaying the resultant solution to determine the amount of API released, compared to that of an identical amount of API-containing particles coated with the same amount of the same coating, or dosage form, without the fat/wax. Crush resistant as described herein is defined as the resistance of drug (API) release from the coated particles (or dosage form) to enhancement under the influence of mechanical stresses. Drug release from the coated particle is determined in accordance with the methods and apparatus used to measure dissolution and drug release as described in the latest version of United Sates Pharmacopoeia (Chapter <711> 2008), with or without modifications. To assess crushing resistance, drug release from the coated particles is initially measured by placing the particles (or dosage form) in a suitable dissolution media in the USP apparatus and measuring how much drug is released over a certain period of time. After subjecting the coated particles (or dosage form) to mechanical stresses the drug release from the stressed or tampered protected particles is then measured as described above. The enhancement of release is calculated as the difference in drug release from the coated particles at certain time points before and after applying the mechanical stress. The lower the enhancement the better the crushing resistance. Examples of mechanical stress include, but not limited to, applying compression and/or shear forces onto the particles by using mortar and pestles or any other suitable configuration (ex. pistons and cylinders, ball mills). The severity of stress can be controlled by controlling the force applied, the time period when the particles are exposed to stress (number of hits inflicted by the pestle/piston, duration of running in the mill) and the materials of construction of the mortar and pestle (or any other equipment). For one aspect of this invention, the coated particles were subjected to mechanical stress by using 130 mm OD Porcelain mortar and 1-pound pestle. In summary, the particles are placed in a ceramic mortar (13 cm outer diameter) then by using a pestle and applying force vertically downward, the coated granules or tablets are crushed by 360° C. circular motion. Each full circle motion constitutes 1 stroke. Each sample is crushed by applying 12 strokes as described above. The crushed samples are then analyzed using USP apparatus number 2 and the dissoluation data at 30 minutes was considered.

The coating in accordance with the present invention comprises any polymeric material which would be acceptable for use in the pharmaceutical industry and whose solubility can be characterized as the following: the successful polymeric material will be at least slightly, preferably sparingly soluble in alcohol. In contrast, the successful material will generally be no more than slightly soluble in water. Often it is virtually insoluble in water. A sparingly soluble polymer is a polymer that requires 30 to 100 parts of a solvent to dissolve one part of the polymer. A slightly soluble polymer requires from about 100 to about 1000 parts of the solvent to dissolve one part of the polymer. Note, however, that these are general requirements. If the manufacturer's literature of a particular material indicates that it is, for example, at least slightly/sparingly soluble in alcohol based solutions, then it can be a candidate for use in a coating, even if when measured by certain tests, its solubility would not fall into the ranges discussed above. Particularly preferred materials include those previously identified as the first material for use in a granulate. Most preferred is ethylcellulose.

These materials when dissolved or dispersed in an alcohol-based solvent as described herein may impart surprising properties, including added crush resistance in comparison to an identical coating applied with water alone, or a high water content solvent with less than about 90% alcohol by volume. They may instead, or also, provide a favorably enhanced (lengthened) release time. Generally, the polymer to solvent ratio in a coating before it is applied is about 1:100 to 1:10, and most preferably about 1:15 to 1:7. Some amount of solvent may be detected in the resulting dosage form once the coating is dried. However it is preferred that the dosage form contains little if any residual solvent.

It has been discovered that including a fat/wax in the coating can also have additional advantages over the use of a coating without a fat/wax. Moreover, the combination of the use of a fat/wax in a coating along with a fat/wax in the core or particle can, in some instances, provide even greater advantages than would be realized from their use in only one or the other.

In particular, as shown in Table 14, formulations including a fat/wax performed better in terms of, for example, abuse resistant when compared to coatings without the fat/wax.

TABLE 14

Granules Data
Hydromorphone Granulations

| Process Description | Time of >90% release | Sim'd Oral Tampering (30 min) |
|---|---|---|
| 50% coat (06B) | 8 hr (95%) | 44% |
| 50% coat, compritol in coating solution, not cured (27A) | * | 21% |

TABLE 14-continued

Granules Data
Hydromorphone Granulations

| Process Description | Time of >90% release | Sim'd Oral Tampering (30 min) |
|---|---|---|
| 50% coat, compritol in coating solution, cured (27B) | 20 hr (90%) | 15% |
| 50% coat, compritol in granulation, not cured (−33) | * | 28% |
| 50% coat, compritol in granulation, cured (−38) | 24 hr (90%) | 29% |

*did not release 100% after 24 hours

Figure 11:
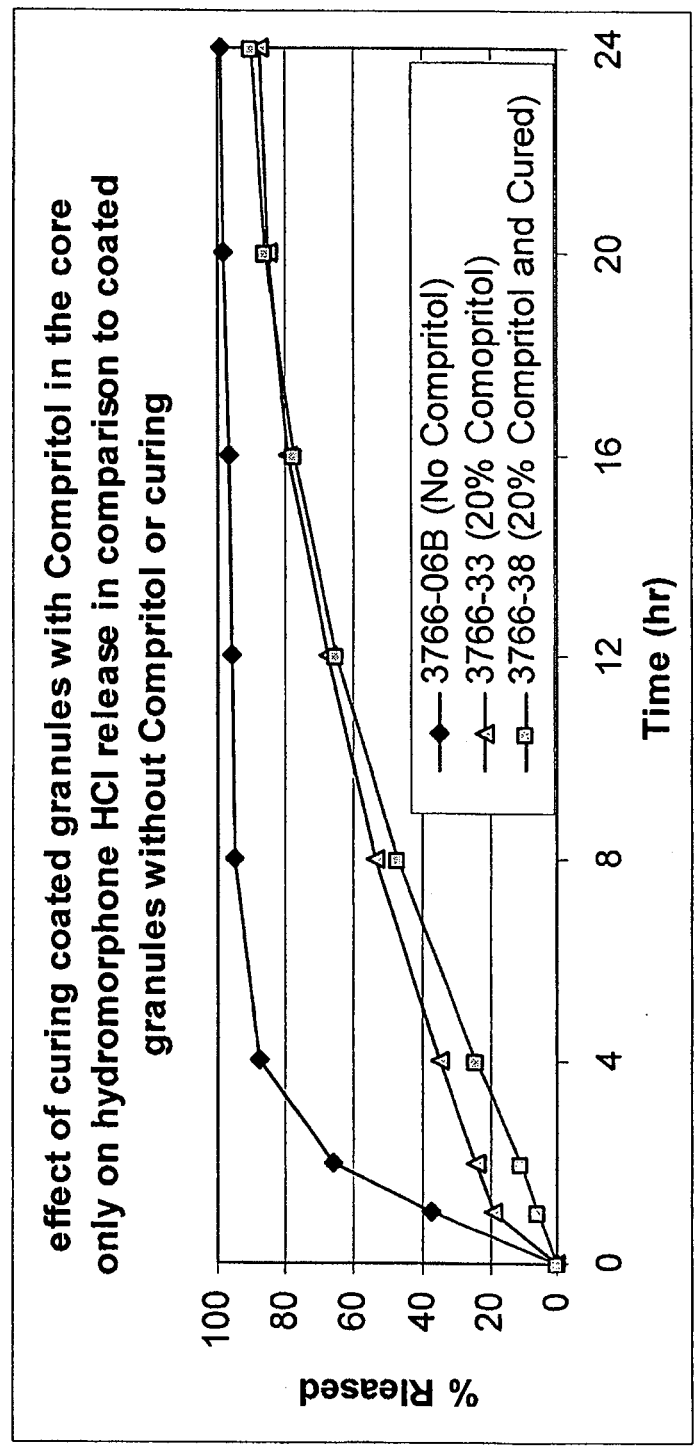
FIG. 11 illustrates the effect of curing coated granules with Compritol in the core only on hydromorphone HCl release in comparison to coated granules without Compritol or curing.
Figure 12:
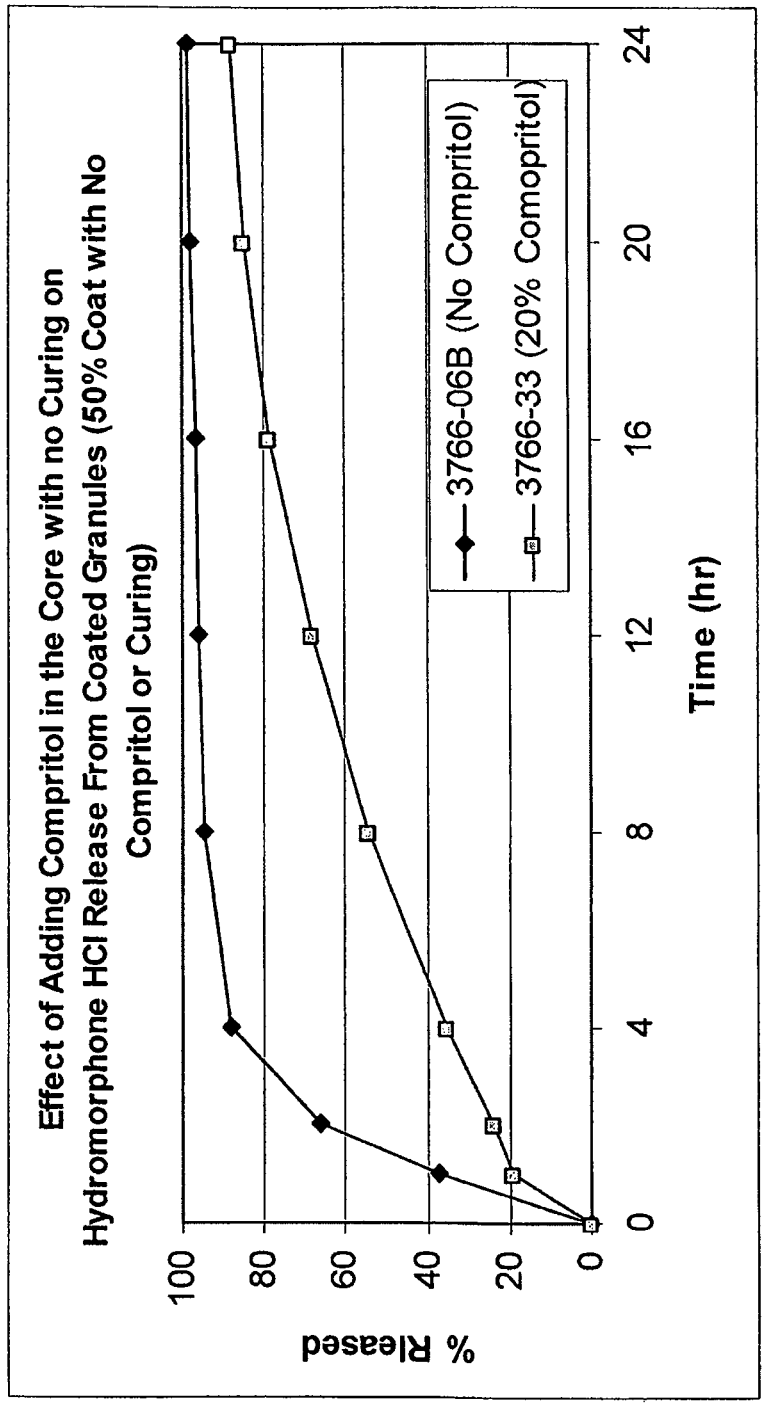
FIG. 12 illustrates the effect of adding compritol in the core with no curing on hydromorphone HCl release from coated granules (50% coat with no compritol or curing) where the shaded diamonds represent lot 3766-06B (no compritol) and the open squares represent lot 3766-33 (20% compritol).
Figure 13:
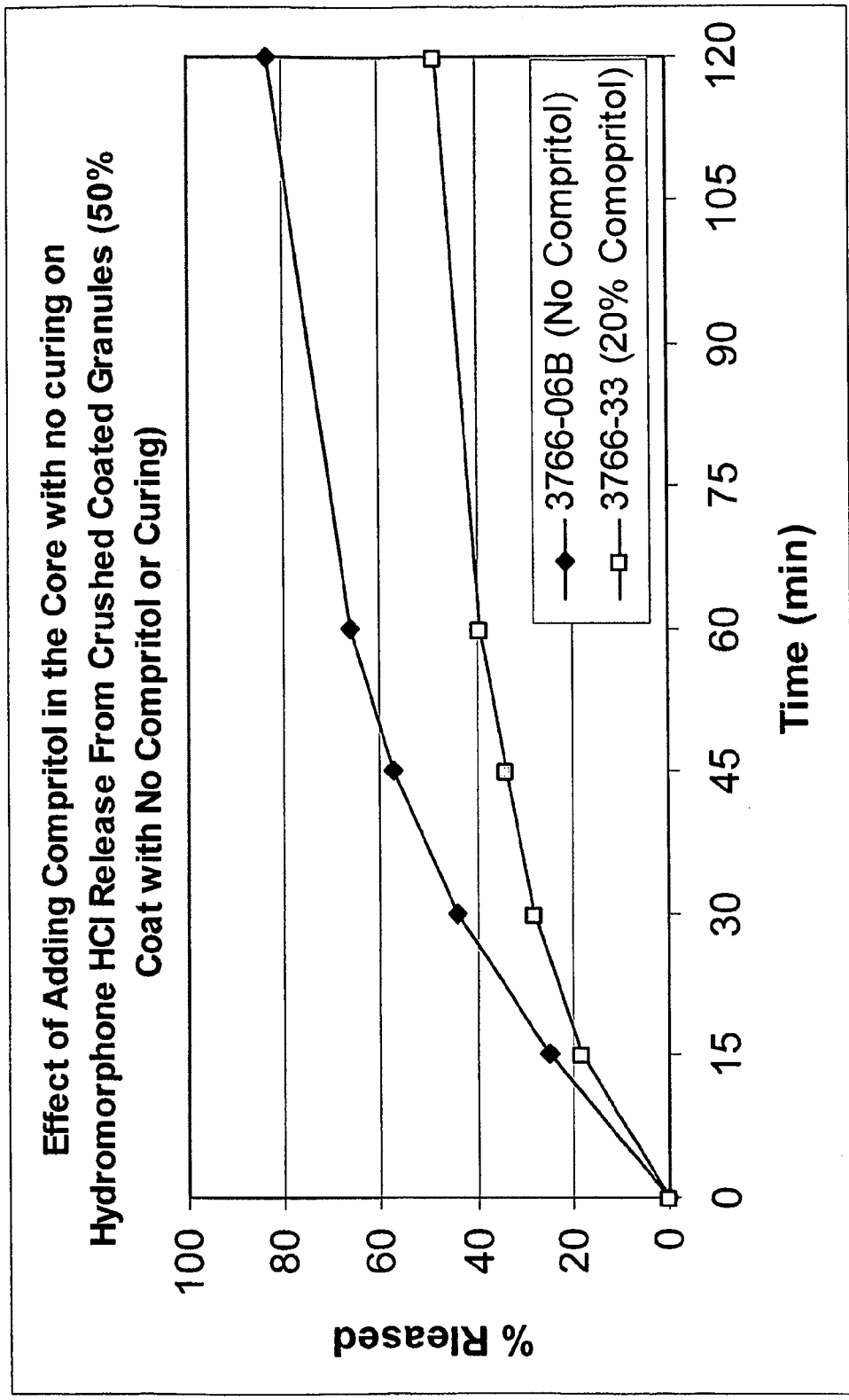
FIG. 13 illustrates the effect of adding compritol in the core with no curing on hydromorphone HCl release from crushed coated granules (50% coat with no compritol or curing) where the shaded diamonds represent lot 3766-06B (no compritol) and the open squares represent lot 3766-33 (20% compritol).
Figure 14:
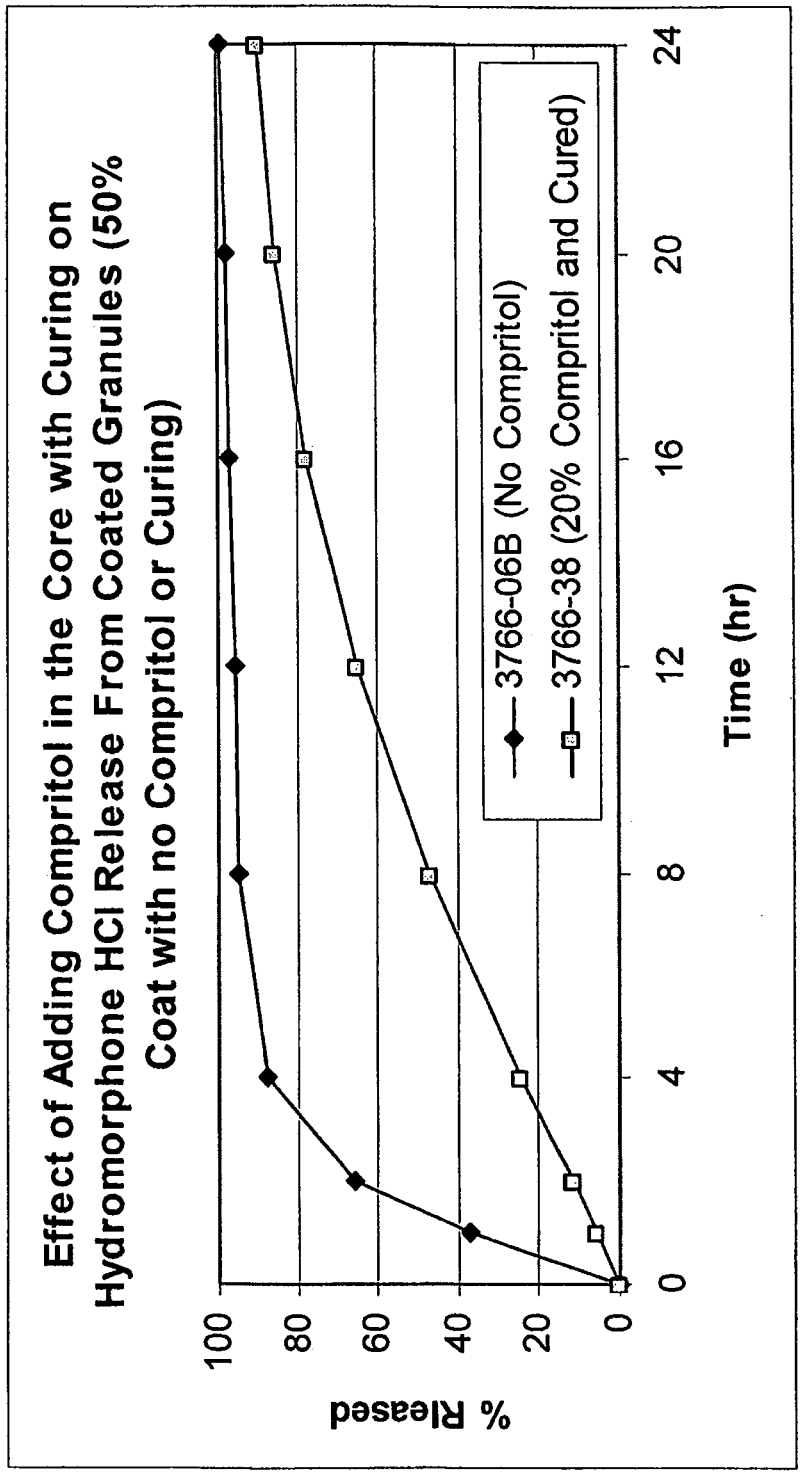
FIG. 14 illustrates the effect of adding compritol in the core with curing on hydromorphone HCl release from coated granules (50% coat with no compritol or curing) where the shaded diamonds represent lot 3766-06B (no compritol) and the open squares represent lot 3766-38 (20% compritol and cured).
Figure 15:
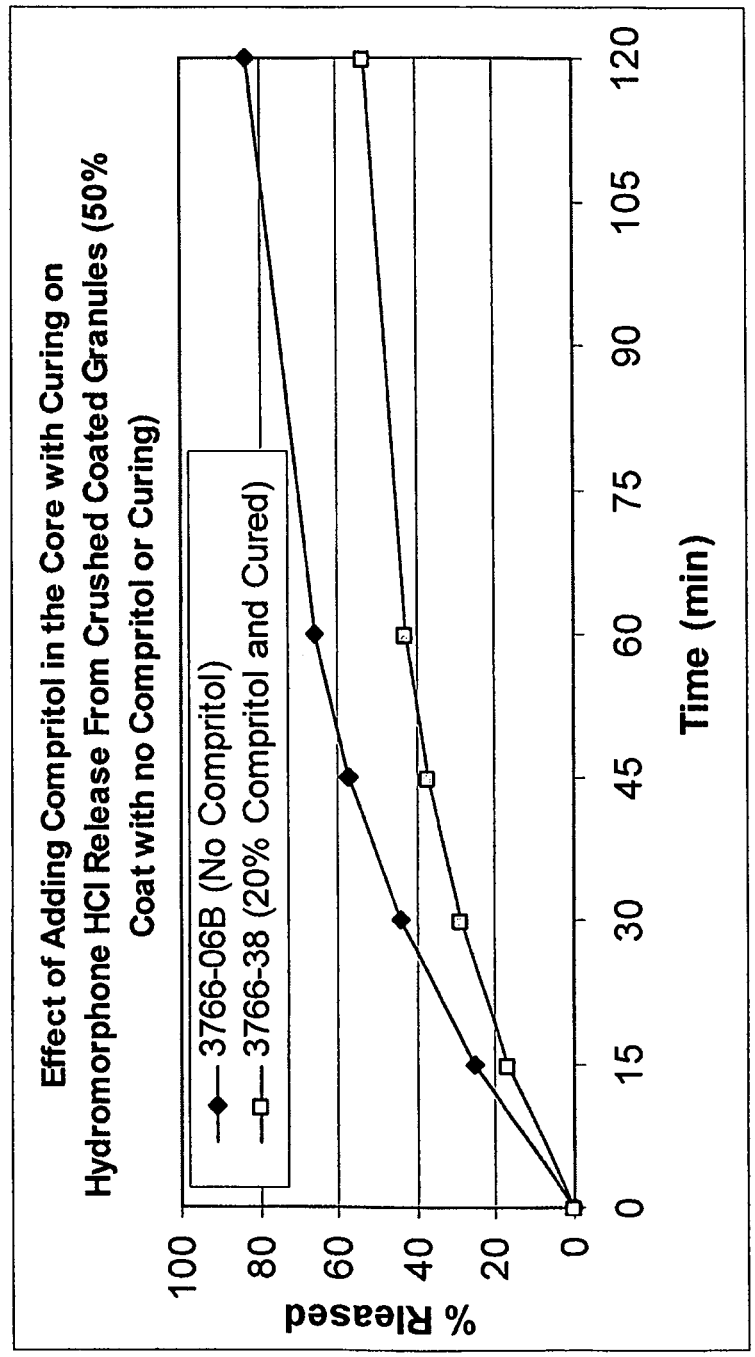
FIG. 15 illustrates the effect of adding compritol in the core with curing on hydromorphone HCl release from crushed coated granules (50% coat with no compritol or curing) where the shaded diamonds represent lot 3766-06B (no compritol) and the open squares represent lot 3766-38 (20% compritol and cured).
Figure 16:
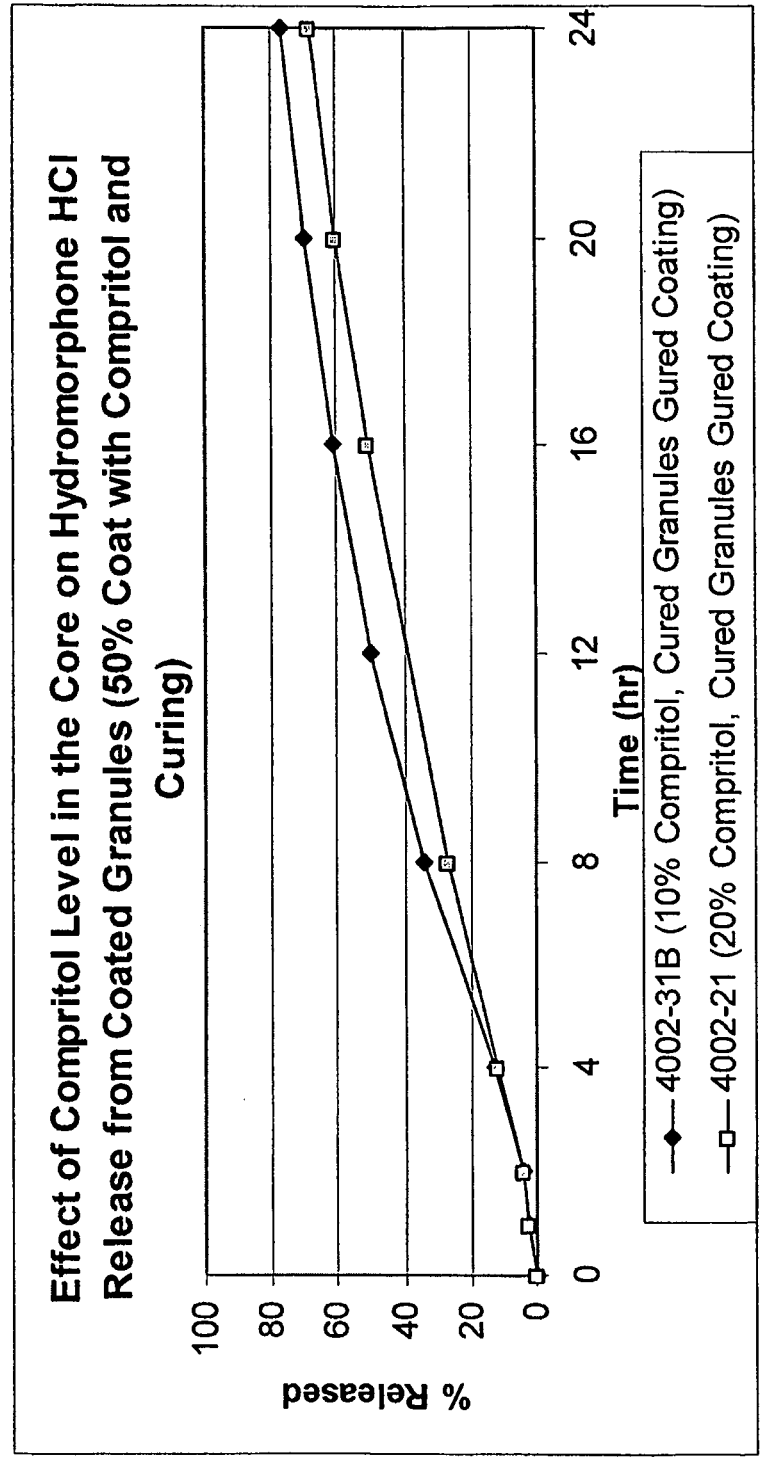
FIG. 16 illustrates the effect of compritol level in the core on hydromorphone HCl release from coated granules (50% coat with compritol and curing) where the shaded diamonds represent lot 4002-31B (10% compritol, cured granules cured coating) and the open squares represent lot 4002-21 (20% compritol, cured granules cured coating).
Figure 17:
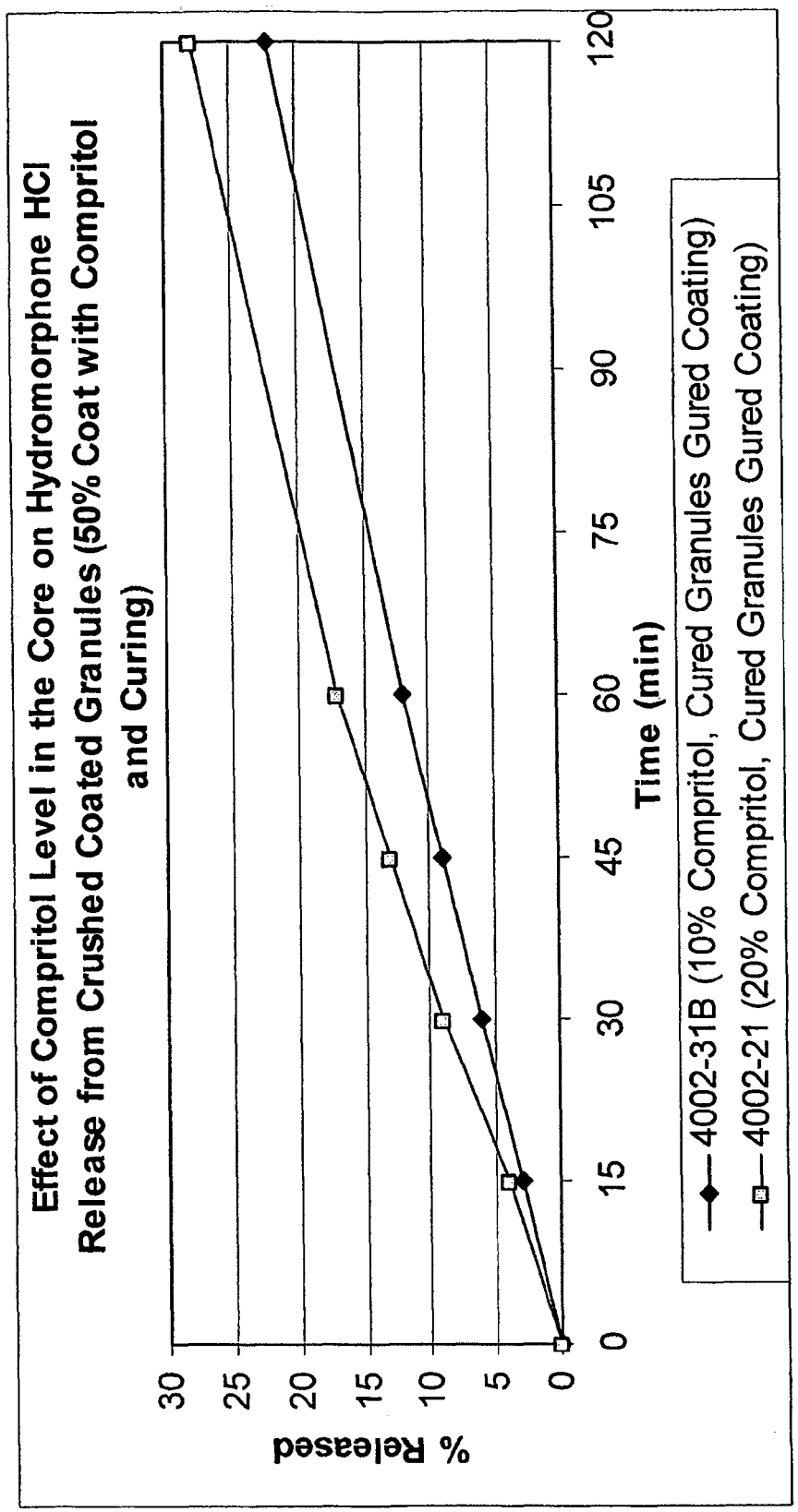
FIG. 17 illustrates the effect of compritol level in the core on hydromorphone HCl release from crushed coated granules (50% coat with compritol and curing) where the shaded diamonds represent lot 4002-31B (10% compritol, cured granules cured coating) and the open squares represent lot 4002-21 (20% compritol, cured granules cured coating).
Figure 18:
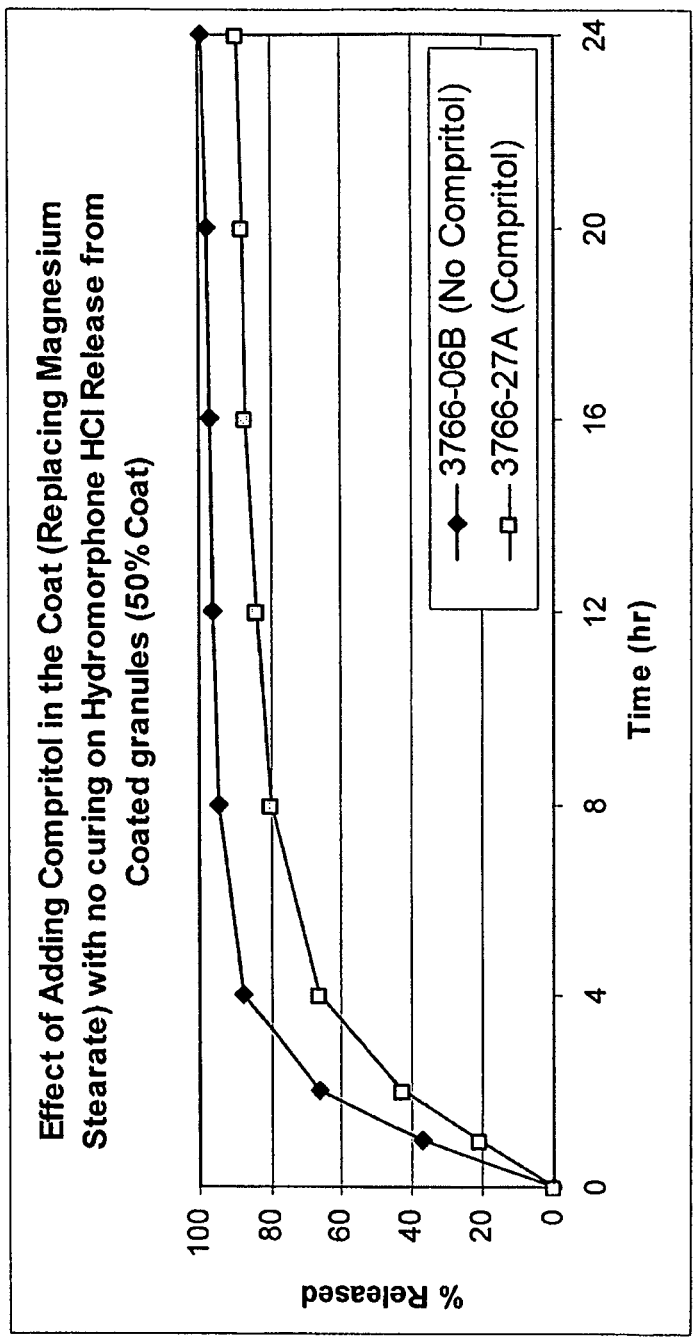
FIG. 18 illustrates the effect of adding compritol in the coat (replacing magnesium stearate) with no curing on hydromorphone HCl release from coated granules (50% coat) where the shaded diamonds represent lot 3766-06B (no compritol) and the open squares represent lot 3766-27A (compritol).
Figure 19:
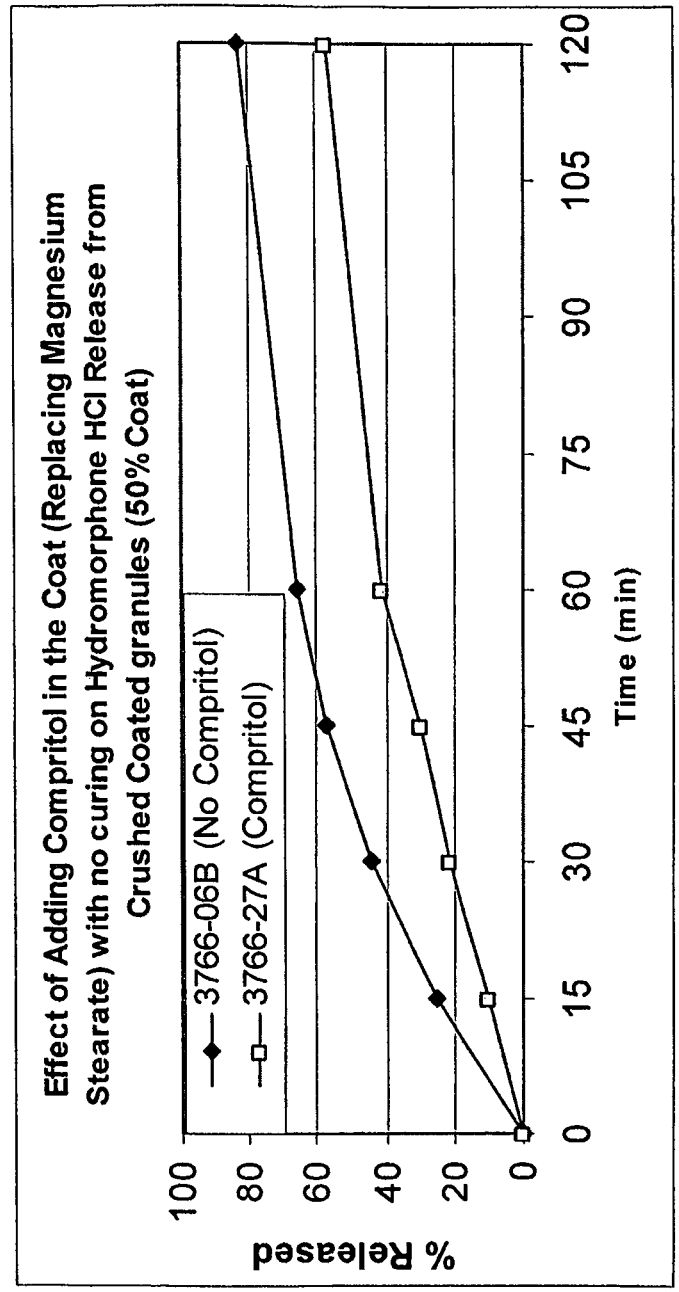
FIG. 19 illustrates the effect of adding compritol in the coat (replacing magnesium stearate) with no curing on hydromorphone HCl release from crushed coated granules (50% coat) where the shaded diamonds represent lot 3766-06B (no compritol) and the open squares represent lot 3766-27A (compritol).
Figure 20:
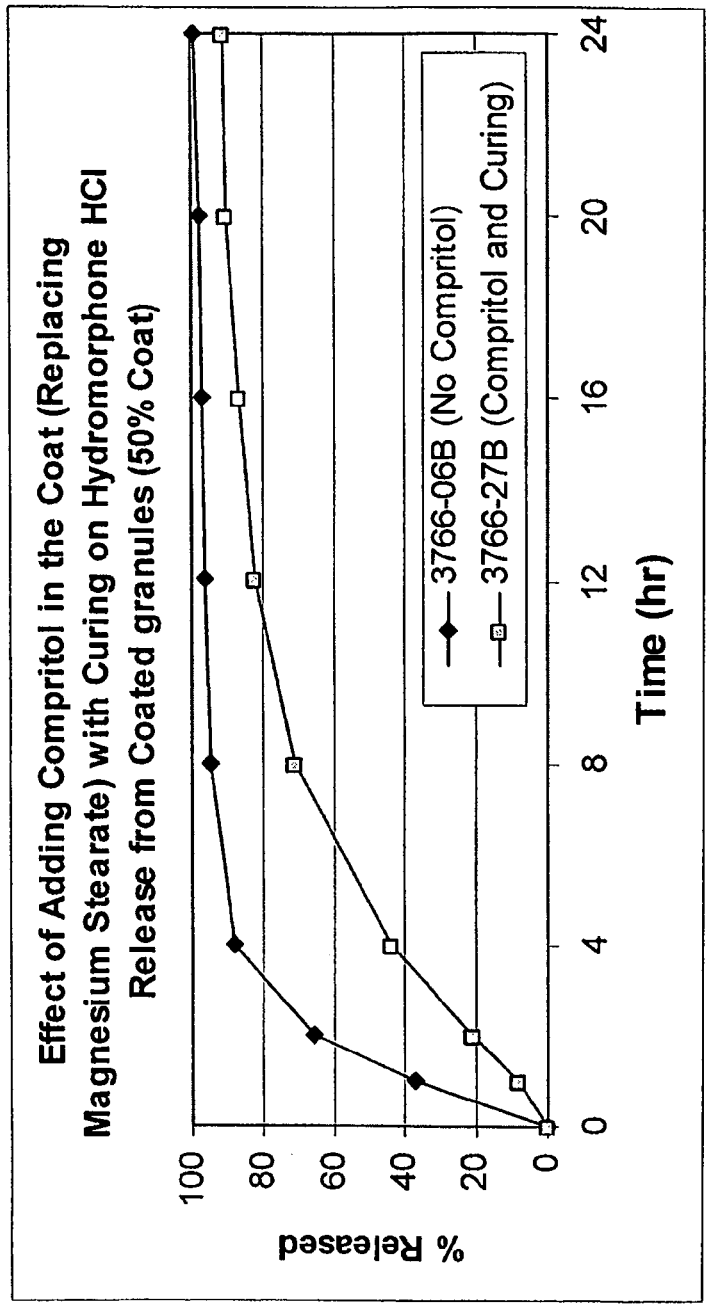
FIG. 20 illustrates the effect of adding compritol in the coat (replacing magnesium stearate) with curing on hydromorphone HCl release from coated granules (50% coat) where the shaded diamonds represent lot 3766-06B (no compritol) and the open squares represent lot 3766-27B (compritol and curing).
Figure 21:
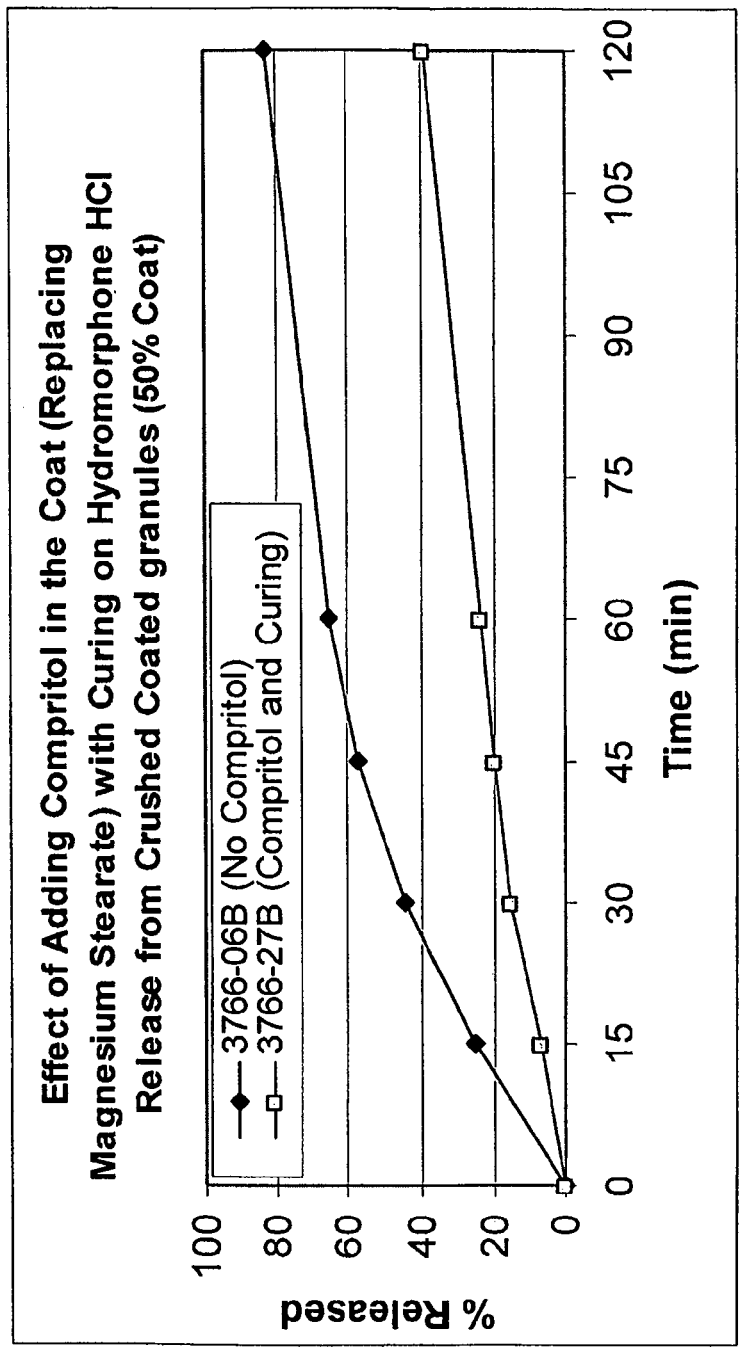
FIG. 21 illustrates the effect of adding compritol in the coat (replacing magnesium stearate) with curing on hydromorphone HCl release from crushed coated granules (50% coat) where the shaded diamonds represent lot 3766-06B (no compritol) and the open squares represent lot 3766-27B (compritol and curing).
Figure 22:
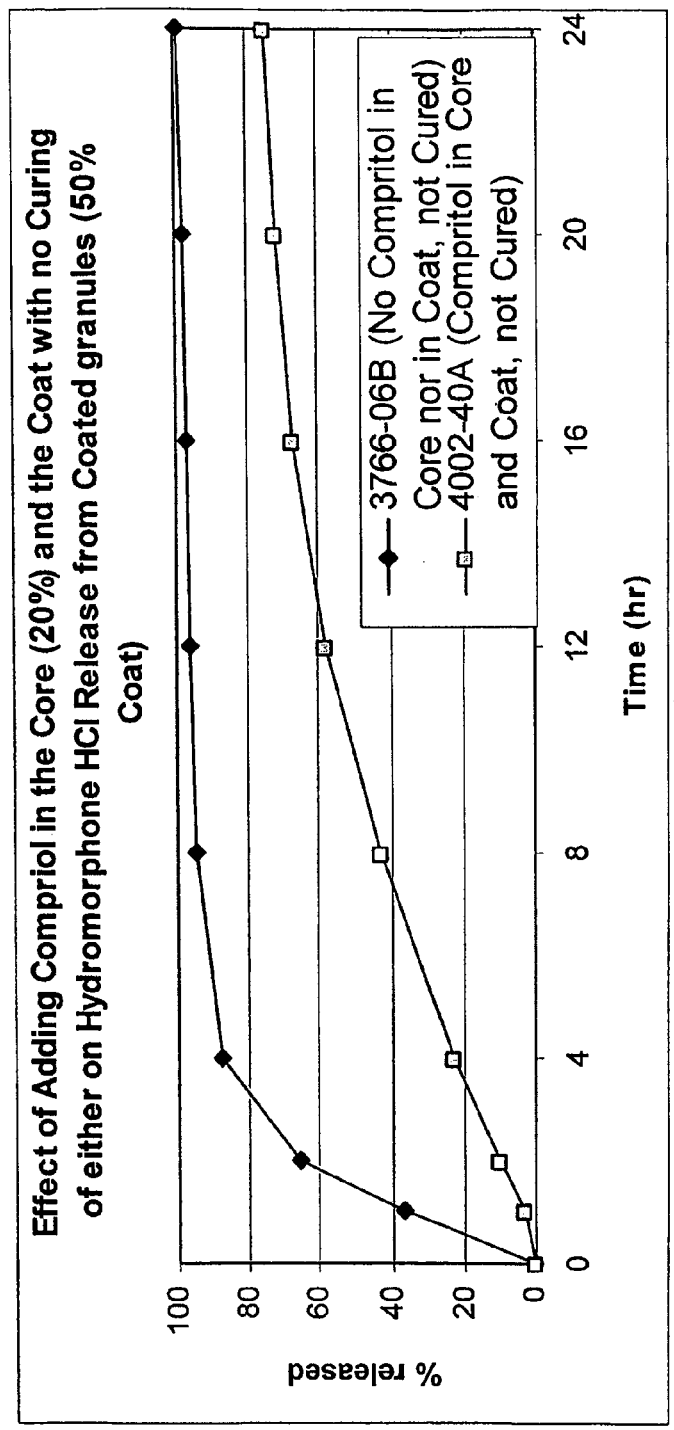
FIG. 22 illustrates the effect of adding compritol in the core (20%) and the coat with no curing of either on hydromorphone HCl release from coated granules (50% coat) where the shaded diamonds represent lot 3766-06B (no compritol in core nor in coat, not cured) and the open squares represent lot 4002-40A (compritol in core and coat, not cured).
Figure 23:
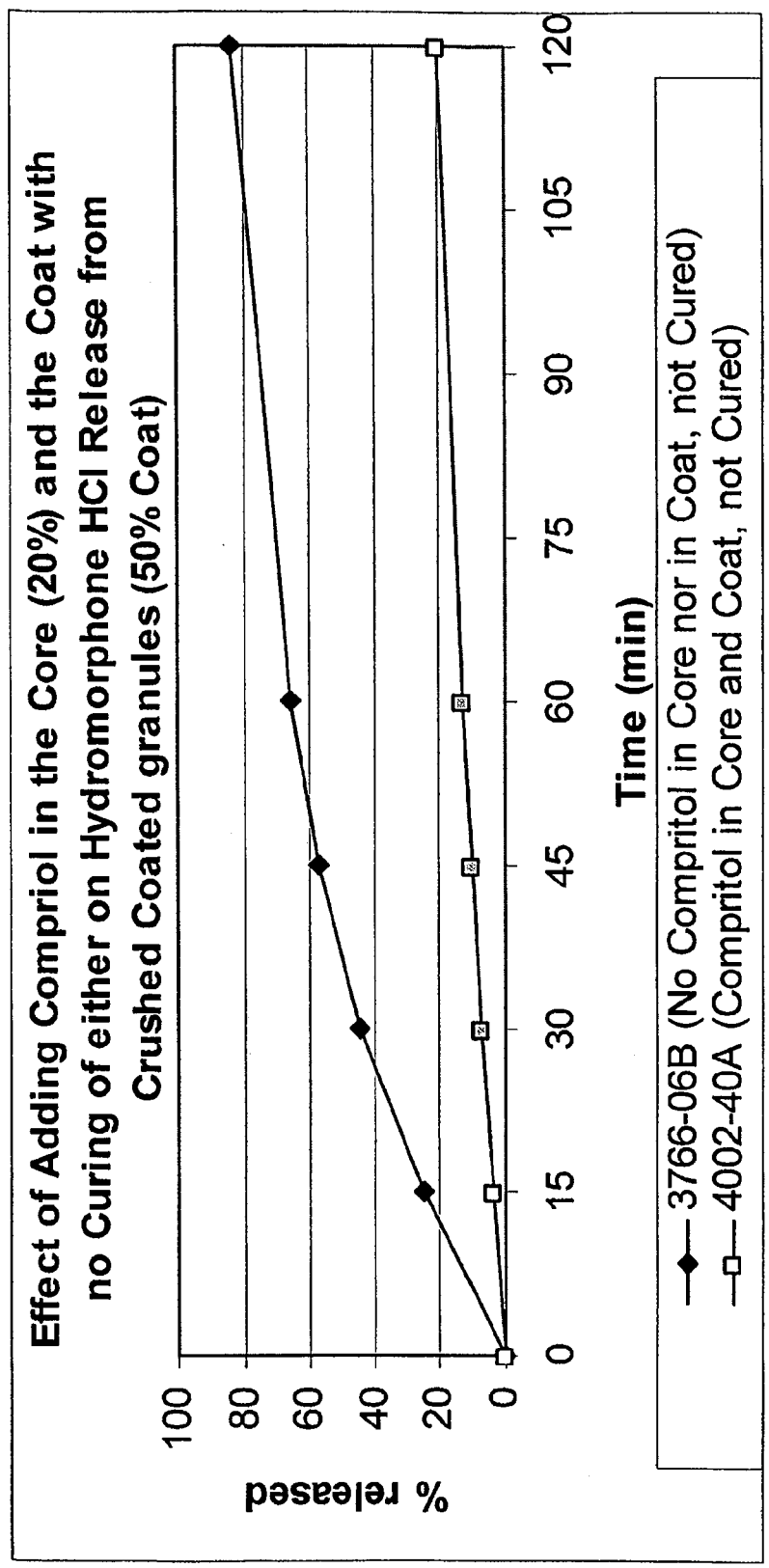
FIG. 23 illustrates the effect of adding compritol in the core (20%) and the coat with no curing of either on hydromorphone HCl release from crushed coated granules (50% coat) where the shaded diamonds represent lot 3766-06B (no compritol in core nor in coat, not cured) and the open squares represent lot 4002-40A (compritol in core and coat, not cured).
Figure 24:
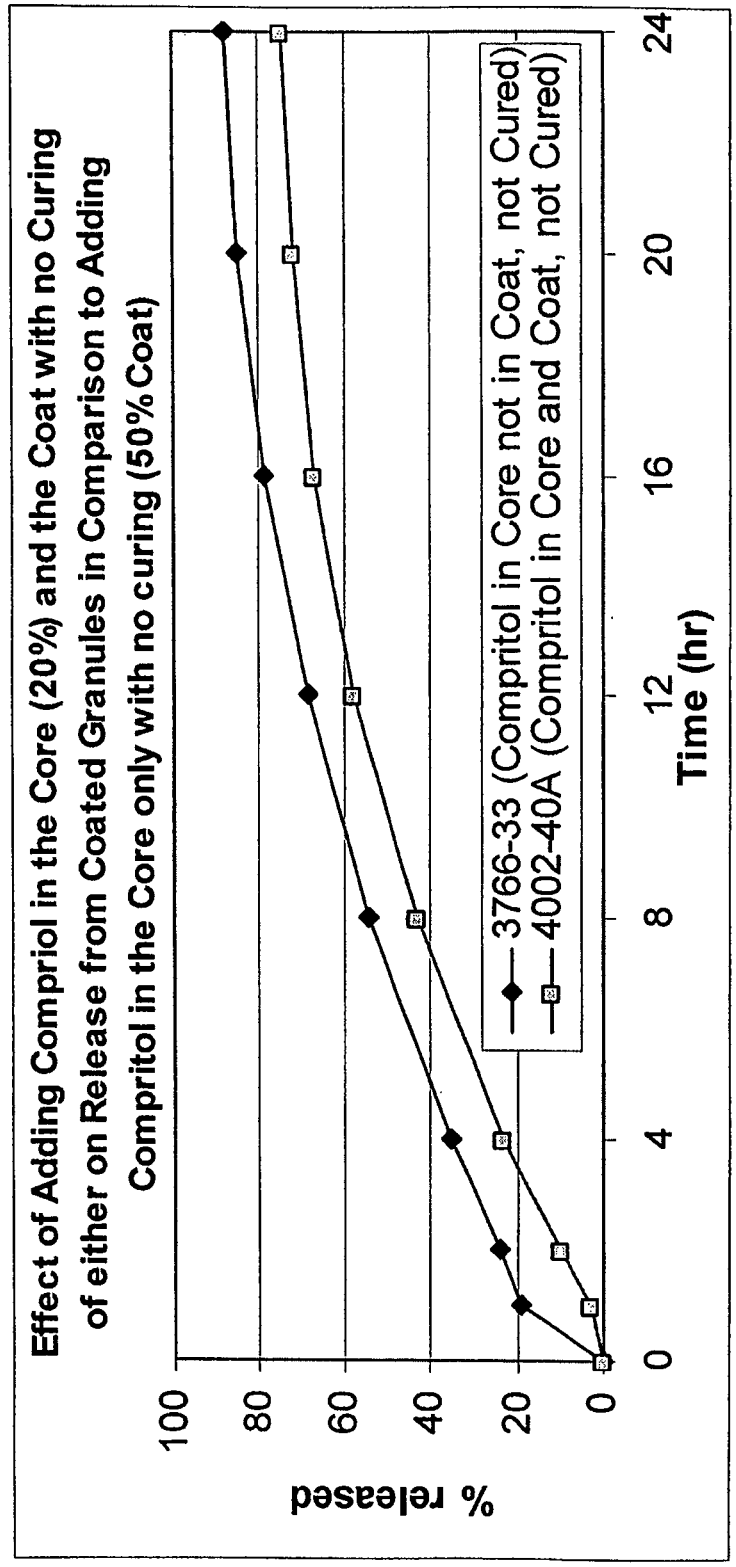
FIG. 24 illustrates the effect of adding compritol in the core (20%) and the coat with no curing of either on release from coated granules in comparison to adding compritol in the core only with no curing (50% coat) where the shaded diamonds represent lot 3766-33 (compritol in core not in coat, not cured) and the open squares represent lot 4002-40A (compritol in core and coat, not cured).
Figure 25:
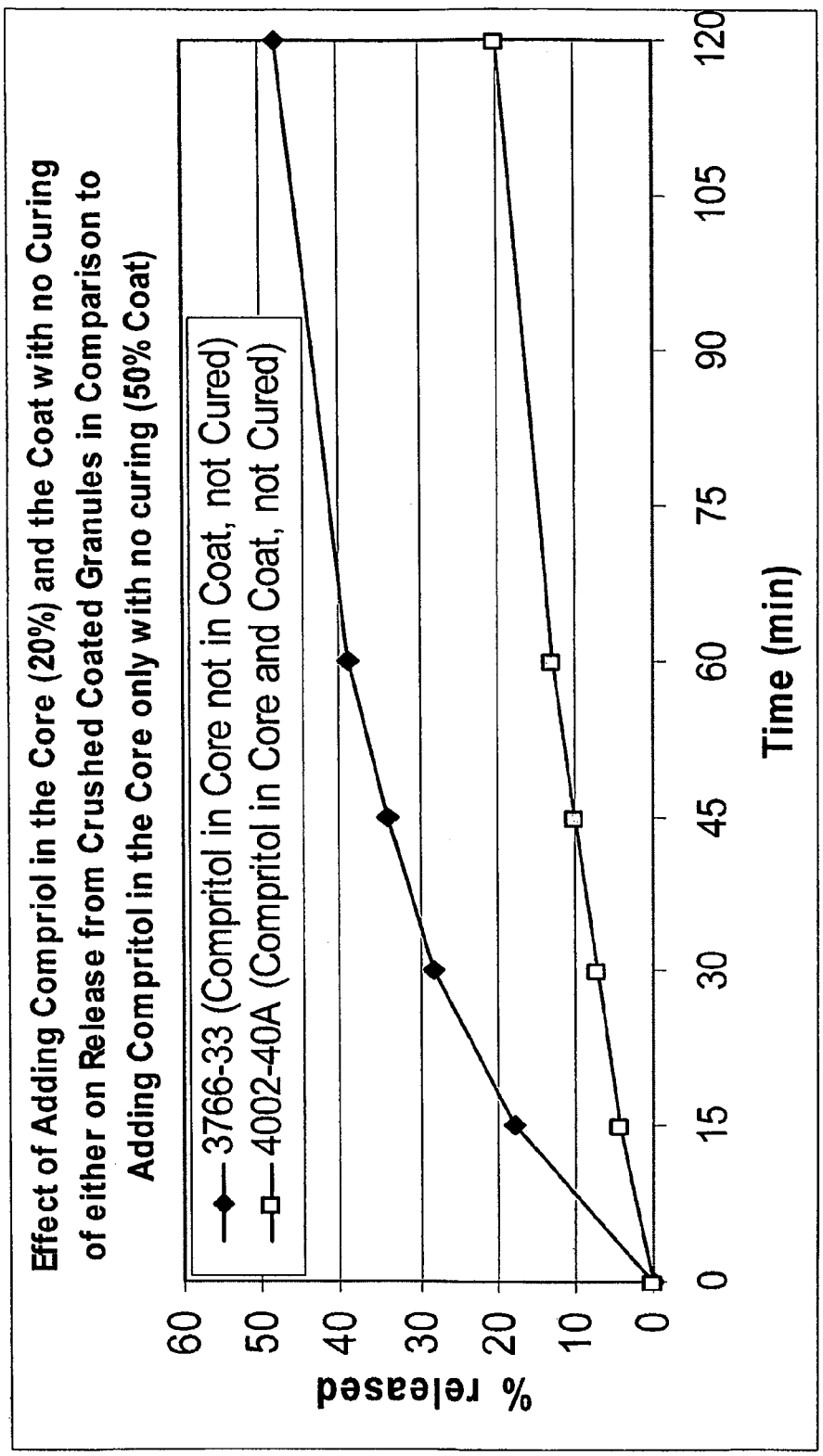
FIG. 25 illustrates the effect of adding compritol in the core (20%) and the coat with no curing of either on release from crushed coated granules in comparison to adding compritol in the core only with no curing (50% coat) where the shaded diamonds represent lot 3766-33 (compritol in core not in coat, not cured) and the open squares represent lot 4002-40A (compritol in core and coat, not cured).
Figure 26:
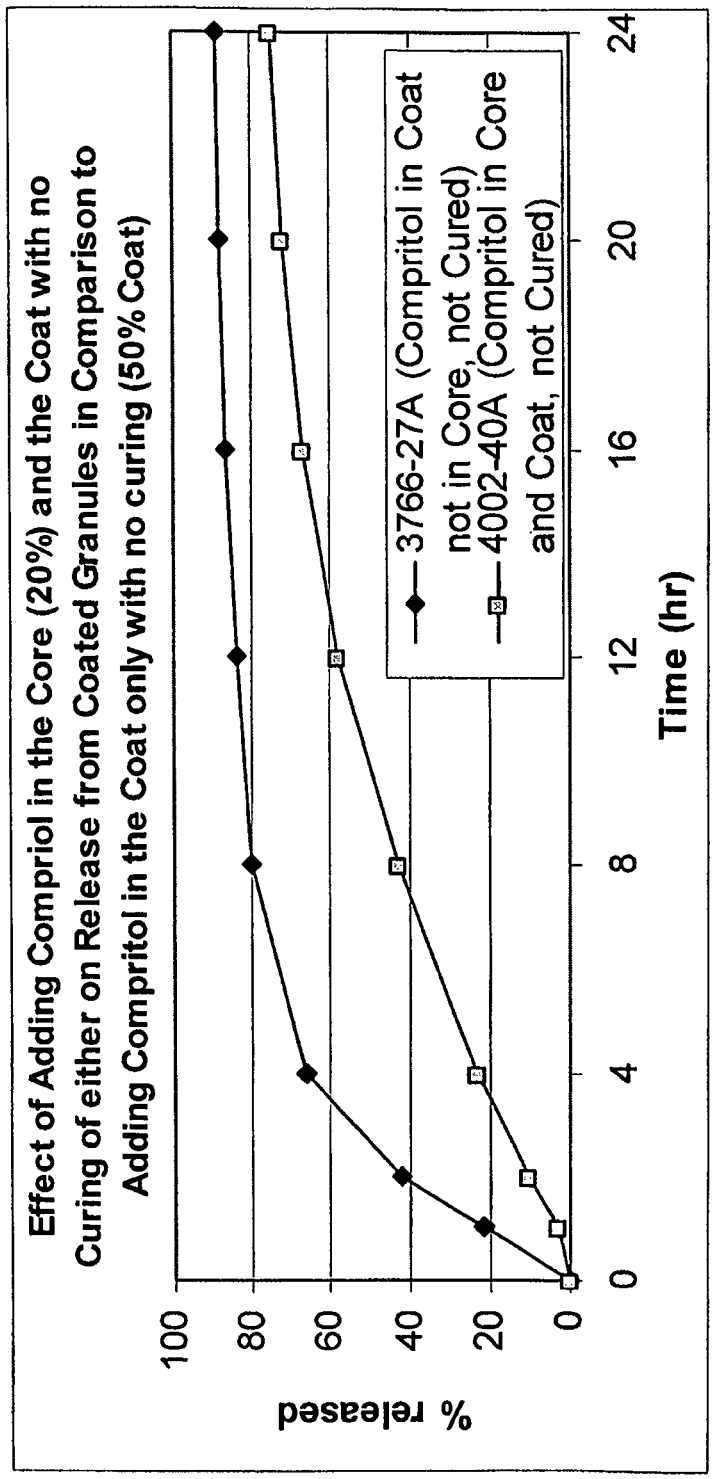
FIG. 26 illustrates the effect of adding compritol in the core (20%) and the coat with no curing of either on release from coated granules in comparison to adding compritol in the coat only with no curing (50% coat) where the shaded diamonds represent lot 3766-27A (compritol in coat not in core, not cured) and the open squares represent lot 4002-40A (compritol in core and coat, not cured).
Figure 27:
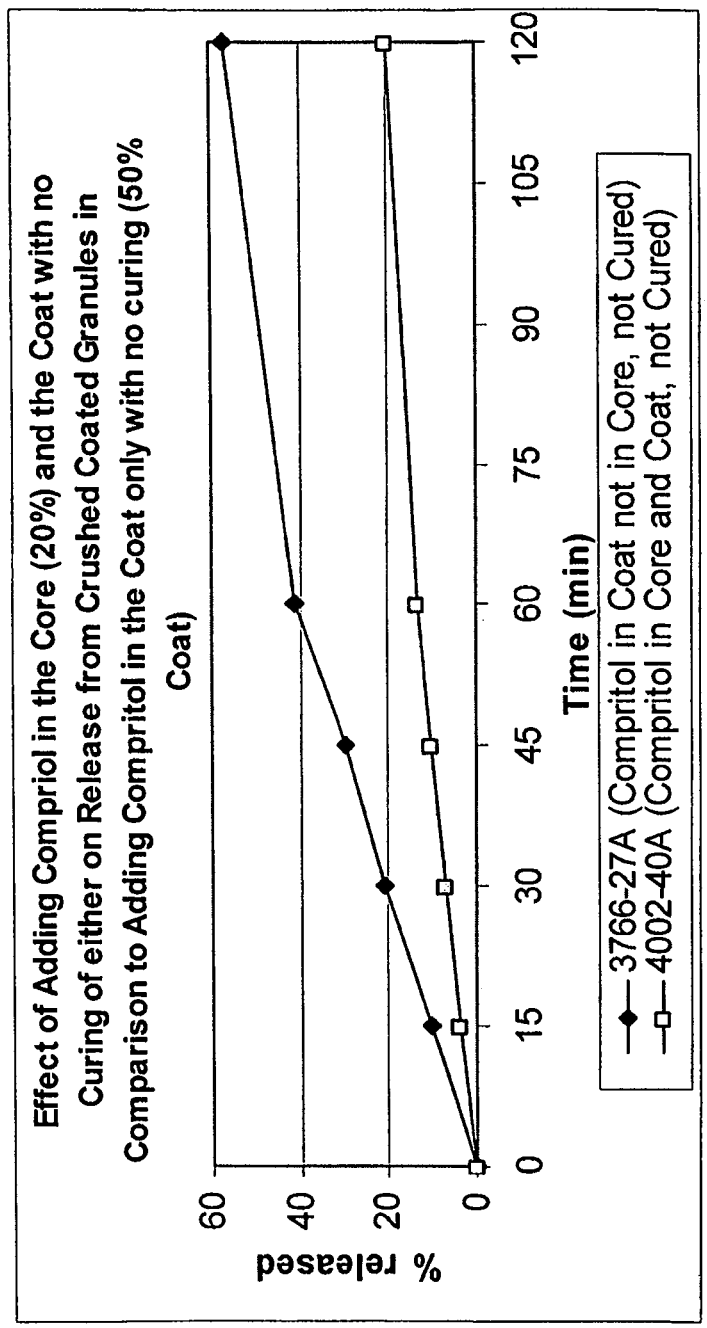
FIG. 27 illustrates the effect of adding compritol in the core (20%) and the coat with no curing of either on release from crushed coated granules in comparison to adding compritol in the coat only with no curing (50% coat) where the shaded diamonds represent lot 3766-27A (compritol in coat not in core, not cured) and the open squares represent lot 4002-40A (compritol in core and coat, not cured).
Figure 28:
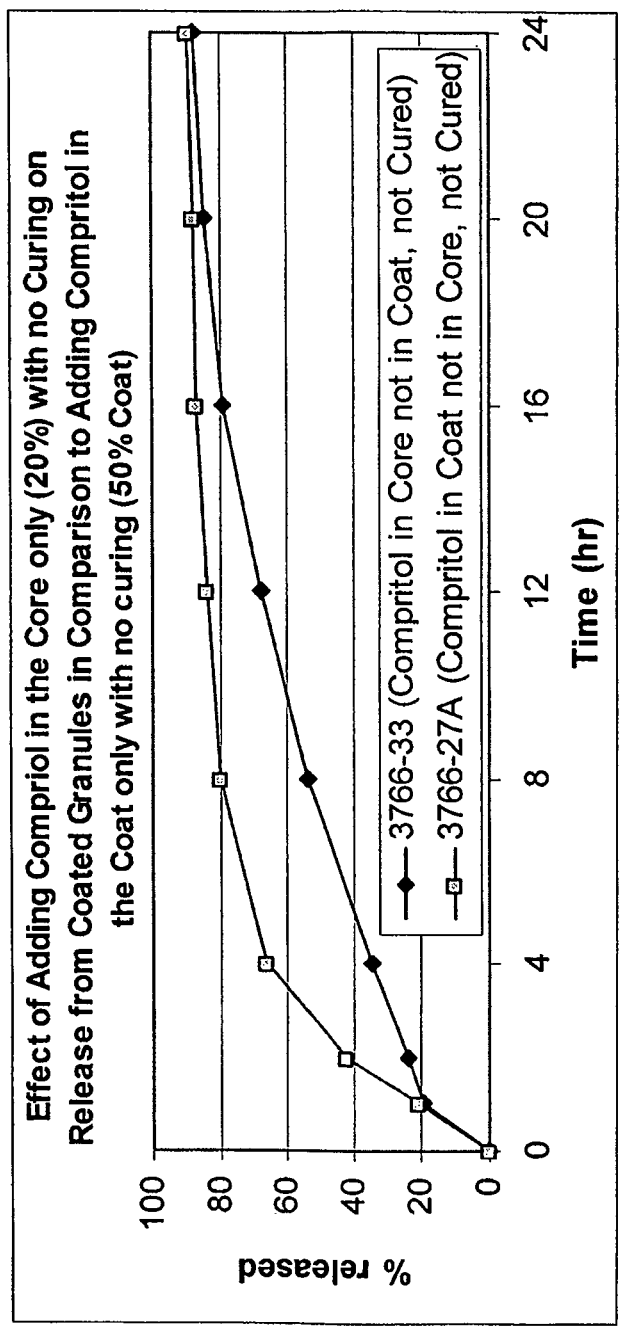
FIG. 28 illustrates the effect of adding compritol in the core only (20%) with no curing on release from coated granules in comparison to adding compritol in the coat only with no curing (50% coat) where the shaded diamonds represent lot 3766-33 (compritol in core not in coat, not cured) and the open squares represent lot 3766-27A (compritol in coat not in core, not cured).
Figure 29:
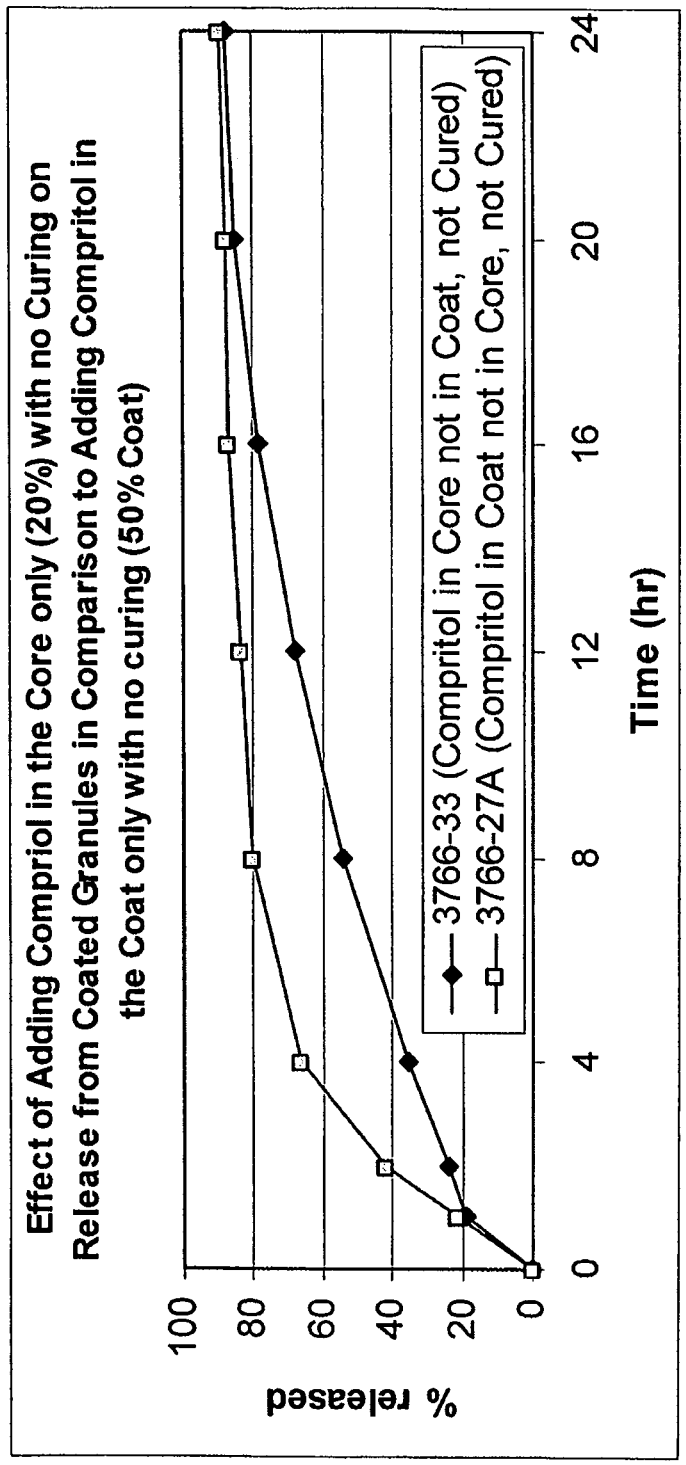
FIG. 29 illustrates the effect of adding compritol in the core only (20%) with no curing on release from crushed coated granules in comparison to adding compritol in the coat only with no curing (50% coat) where the shaded diamonds represent lot 3766-33 (compritol in core not in coat, not cured) and the open squares represent lot 3766-27A (compritol in coat not in core, not cured).
Figure 30:
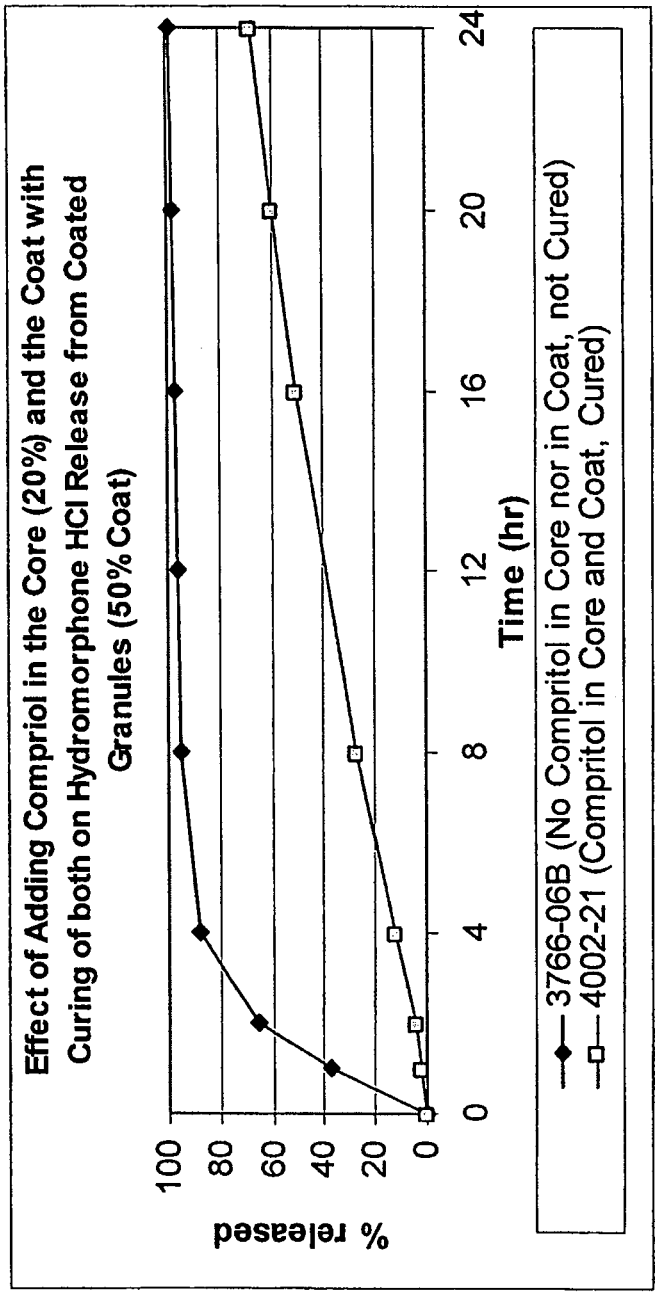
FIG. 30 illustrates the effect of adding compritol in the core (20%) and the coat with curing of both on hydromorphone HCl release from coated granules (50% coat) where the shaded diamonds represent lot 3766-06B (no compritol in core nor in coat, not cured) and the open squares represent lot 4002-21 (compritol in core and coat, cured).
Figure 31:
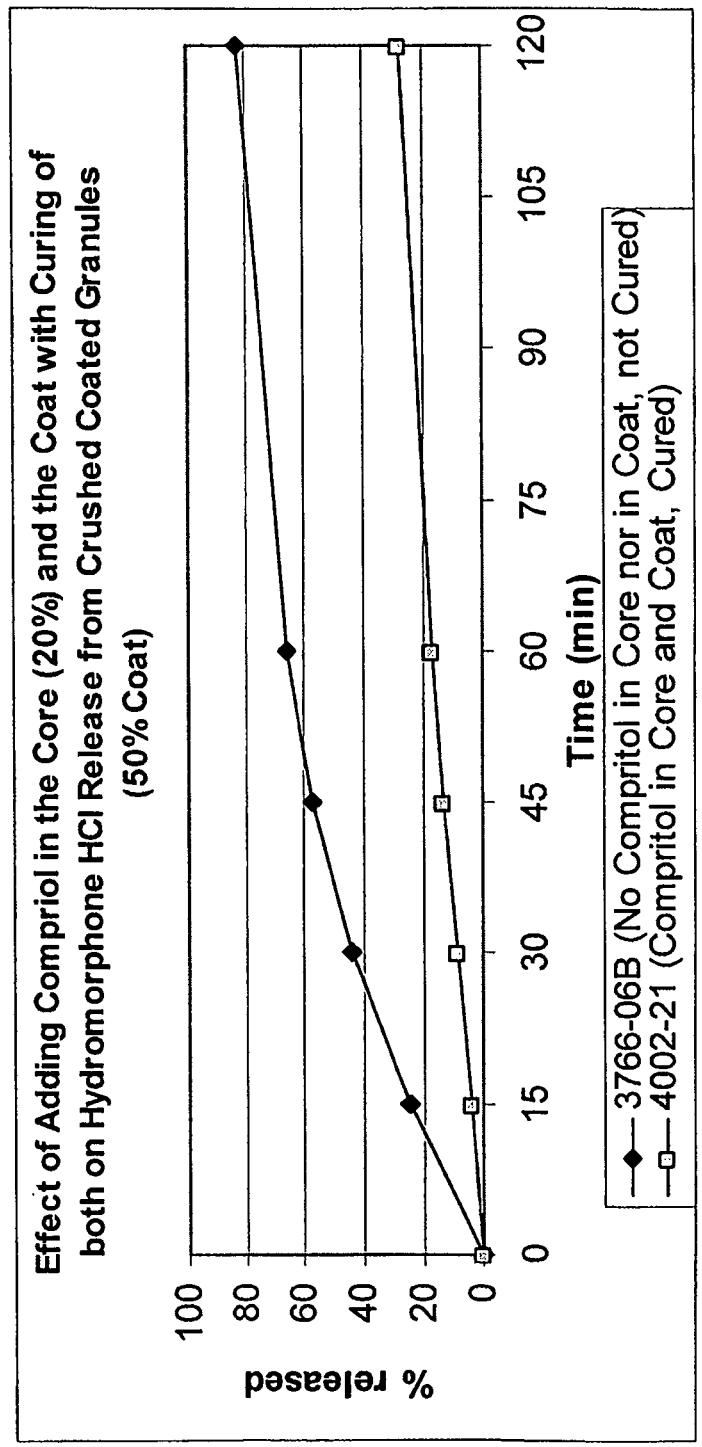
FIG. 31 illustrates the effect of adding compritol in the core (20%) and the coat with curing of both on hydromorphone HCl release from crushed coated granules (50% coat) where the shaded diamonds represent lot 3766-06B (no compritol in core nor in coat, not cured) and the open squares represent lot 4002-21 (compritol in core and coat, cured).
Figure 32:
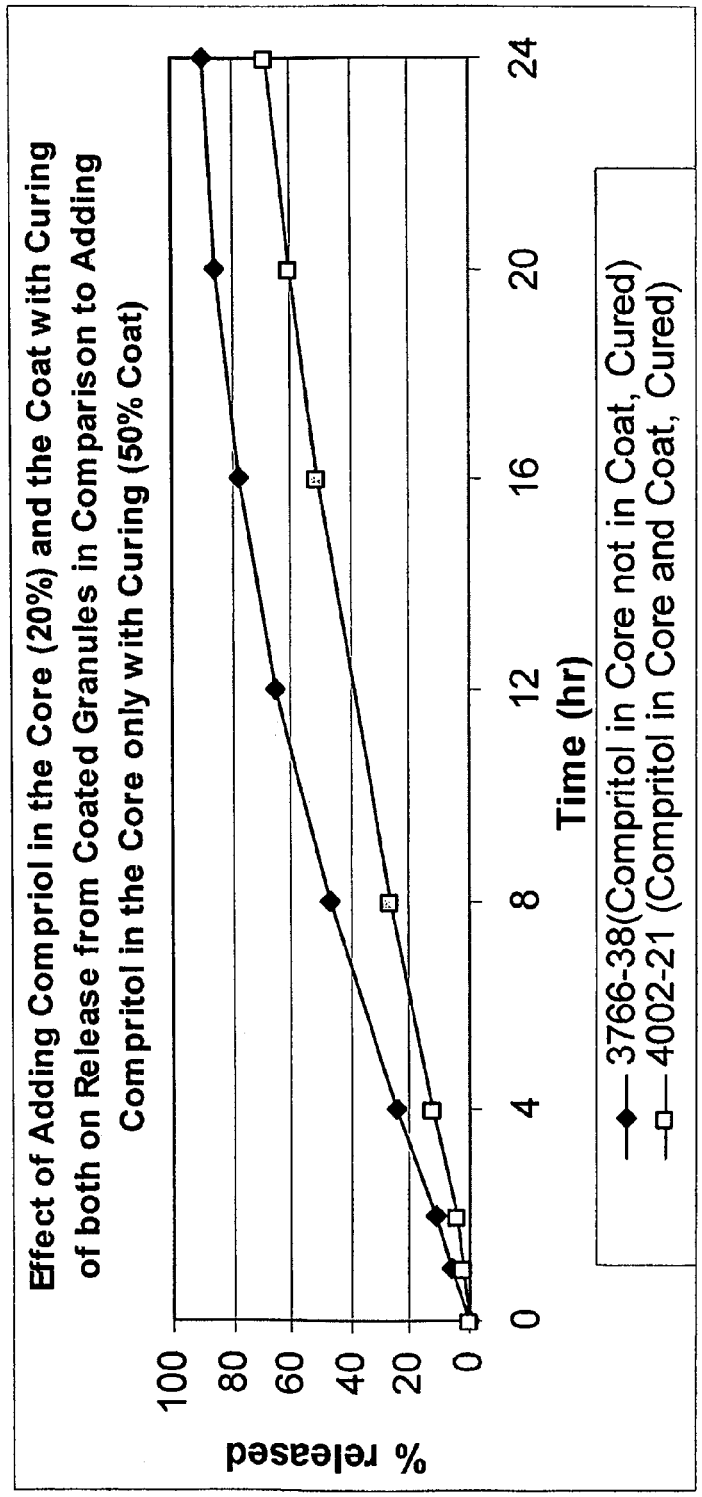
FIG. 32 illustrates the effect of adding compritol in the core (20%) and the coat with curing of both on release from coated granules in comparison to adding compritol in the core only with curing (50% coat) where the shaded diamonds represent lot 3766-38 (compritol in core not in coat, cured) and the open squares represent lot 4002-21 (compritol in core and coat, cured).
Figure 33:
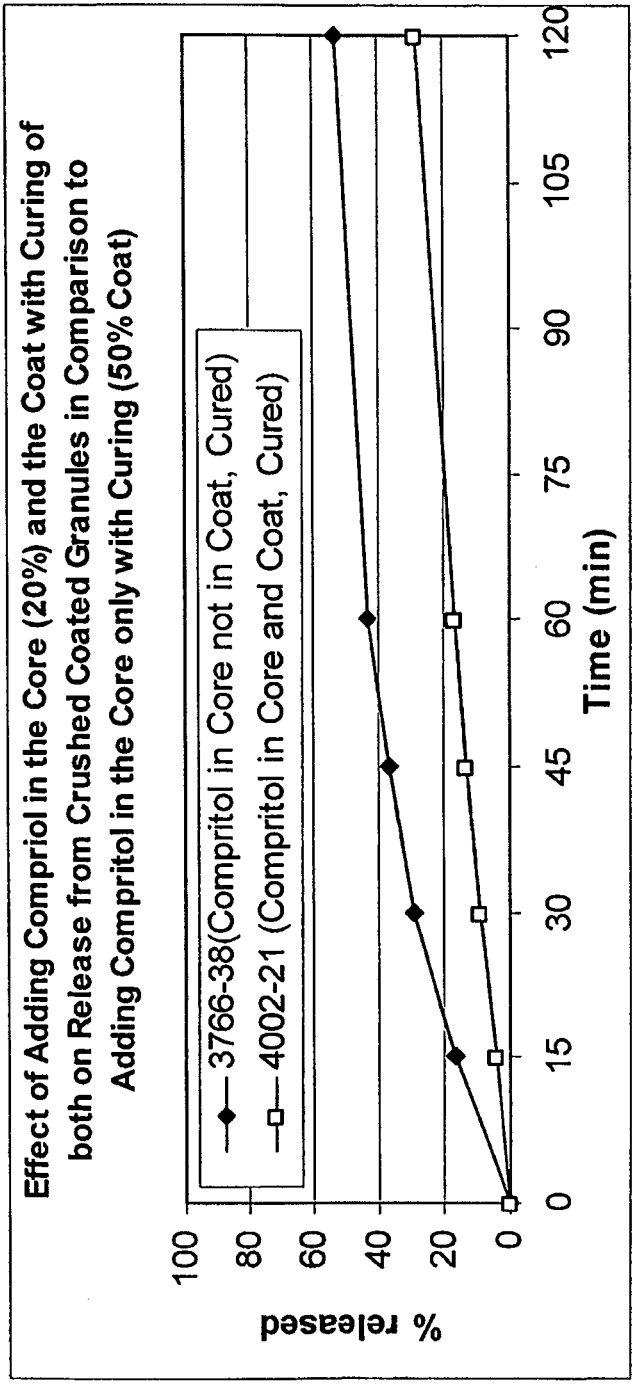
FIG. 33 illustrates the effect of adding compritol in the core (20%) and the coat with curing of both on release from crushed coated granules in comparison to adding compritol in the core only with curing (50% coat) where the shaded diamonds represent lot 3766-38 (compritol in core not in coat, cured) and the open squares represent lot 4002-21 (compritol in core and coat, cured).
Figure 34:
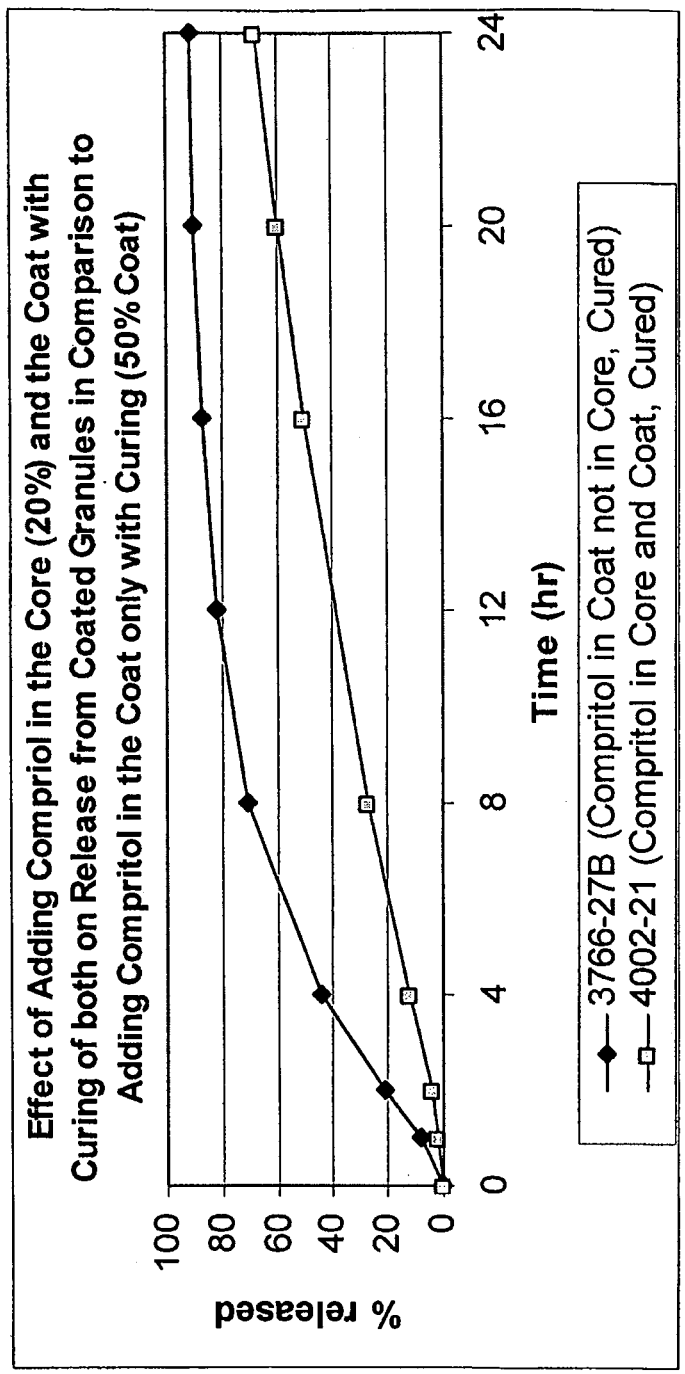
FIG. 34 illustrates the effect of adding compritol in the core (20%) and the coat with curing of both on release from coated granules in comparison to adding compritol in the coat only with curing (50% coat) where the shaded diamonds represent lot 3766-27B (compritol in coat not in core, cured) and the open squares represent lot 4002-21 (compritol in core and coat, cured).
Figure 35:
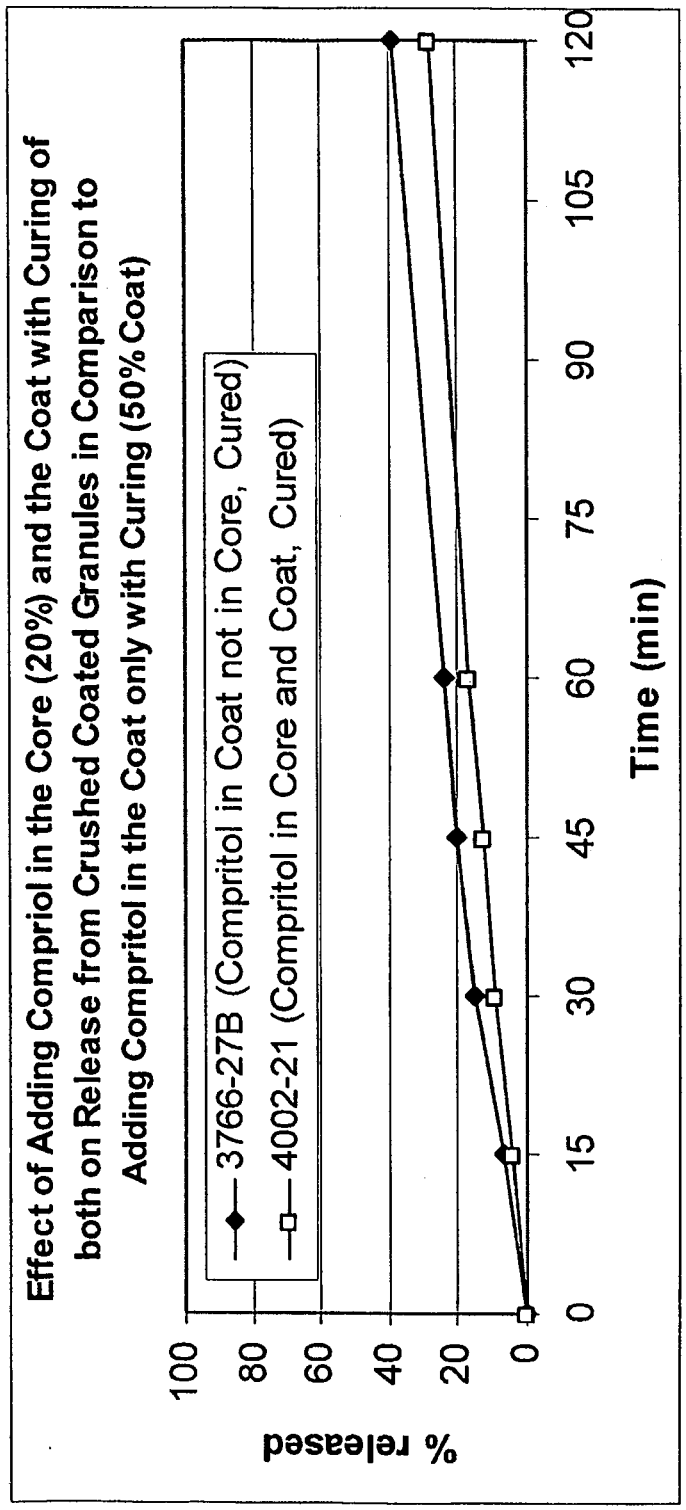
FIG. 35 illustrates the effect of adding compritol in the core (20%) and the coat with curing of both on release from crushed coated granules in comparison to adding compritol in the coat only with curing (50% coat) where the shaded diamonds represent lot 3766-27B (compritol in coat not in core, cured) and the open squares represent lot 4002-21 (compritol in core and coat, cured).
Figure 36:
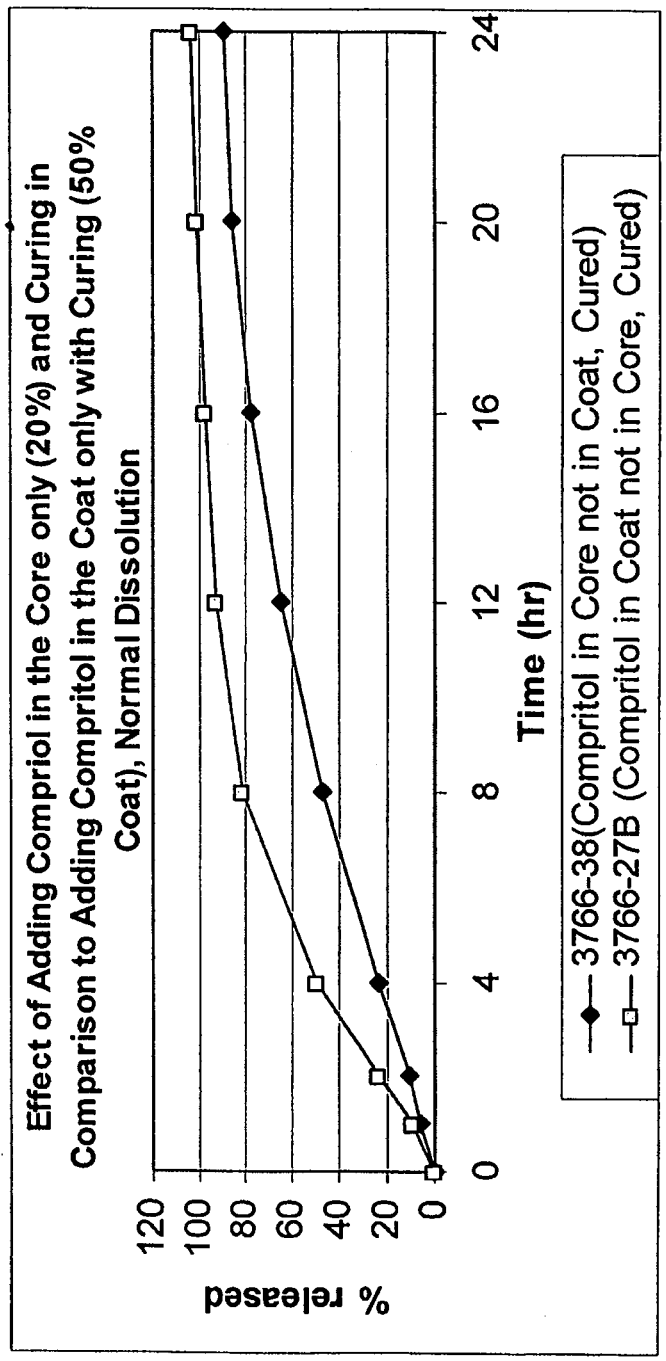
FIG. 36 illustrates the effect of adding compritol in the core only (20%) and curing in comparison to adding compritol in the coat only with curing (50% coat), normal dissolution where the shaded diamonds represent lot 3766-38 (compritol in core not in coat, cured) and the open squares represent lot 3766-27B (compritol in coat not in cure, cured).
Figure 37:
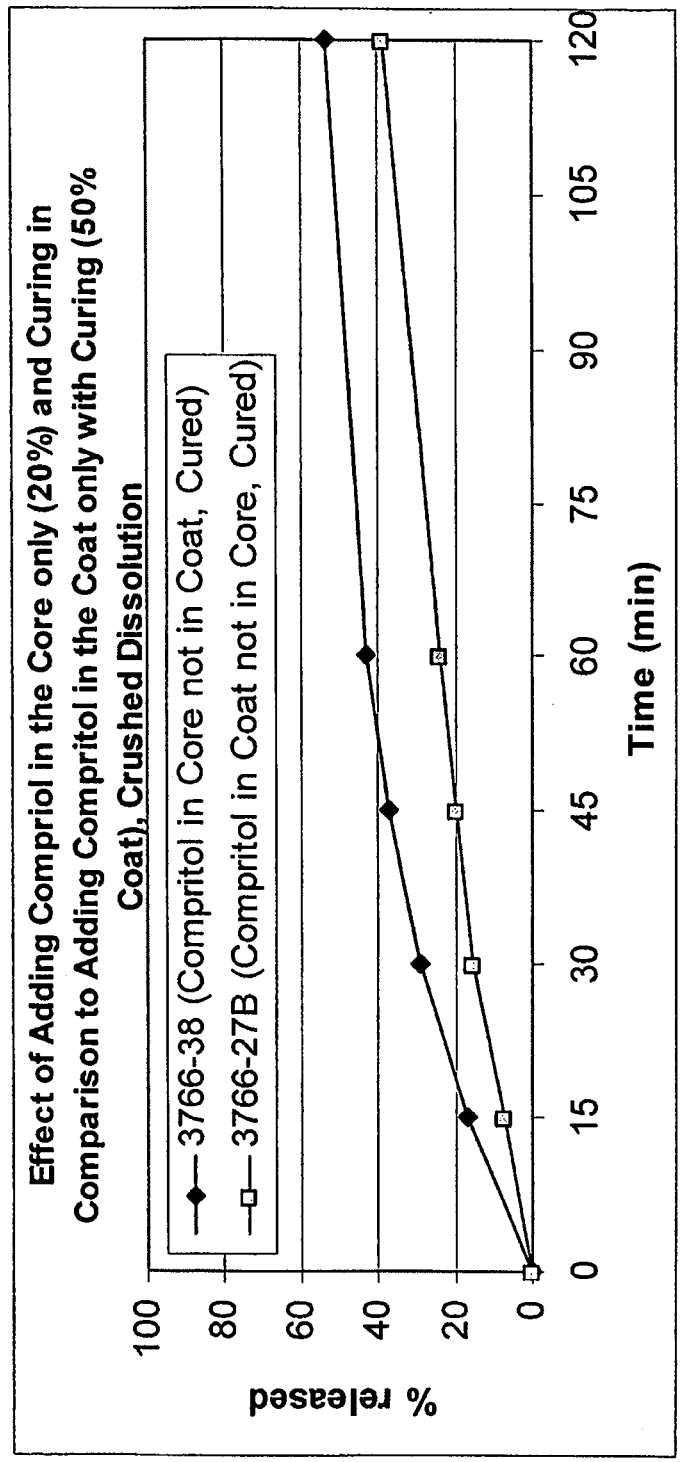
FIG. 37 illustrates the effect of adding compritol in the core only (20%) and curing in comparison to adding compritol in the coat only with curing (50% coat), crushed dissolution where the shaded diamonds represent lot 3766-38 (compritol in core not in coat, cured) and the open squares represent lot 3766-27B (compritol in coat not in cure, cured).
Figure 38:
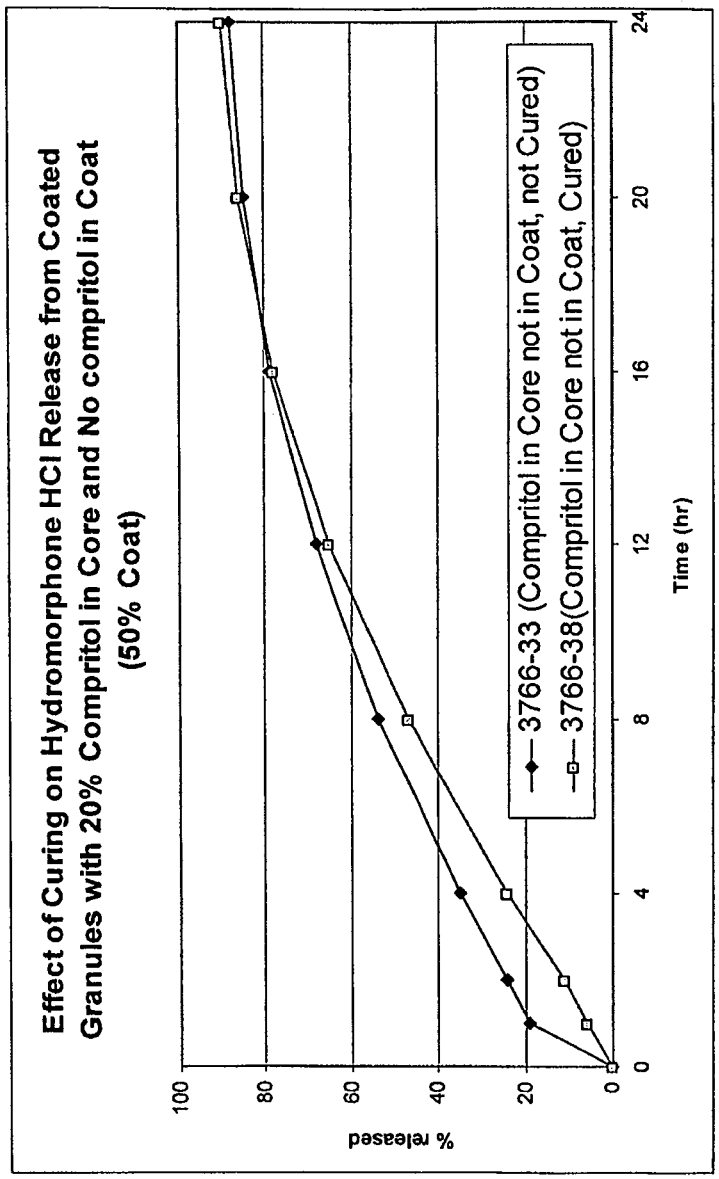
FIG. 38 illustrates the effect of curing on hydromorphone HCl release from coated granules with 20% compritol in core and no compritol in coat (50% coat) where the shaded diamonds represent lot 3766-33 (compritol in core not in coat, not cured) and the open squares represent lot 3766-38 (compritol in core not in coat, cured).
Figure 39:
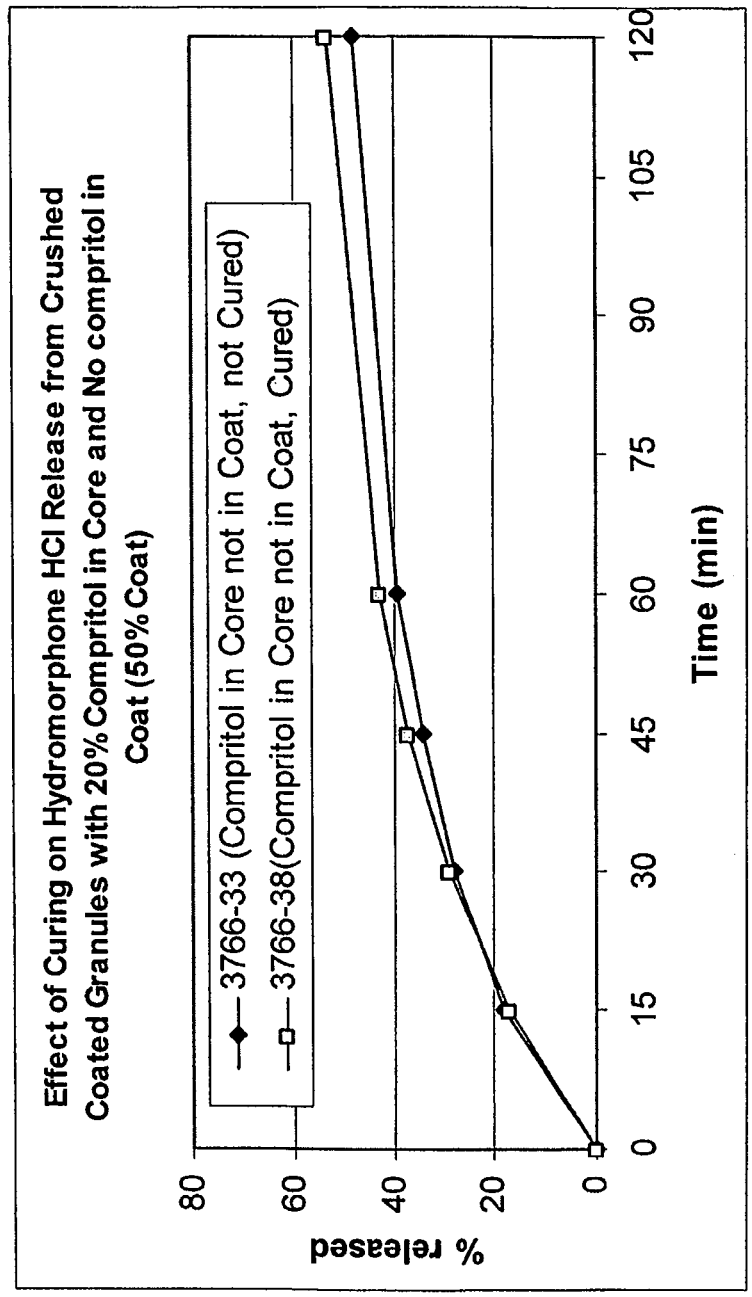
FIG. 39 illustrates the effect of curing on hydromorphone HCl release from crushed coated granules with 20% compritol in core and no compritol in coat (50% coat) where the shaded diamonds represent lot 3766-33 (compritol in core not in coat, not cured) and the open squares represent lot 3766-38 (compritol in core not in coat, cured).
Figure 40:
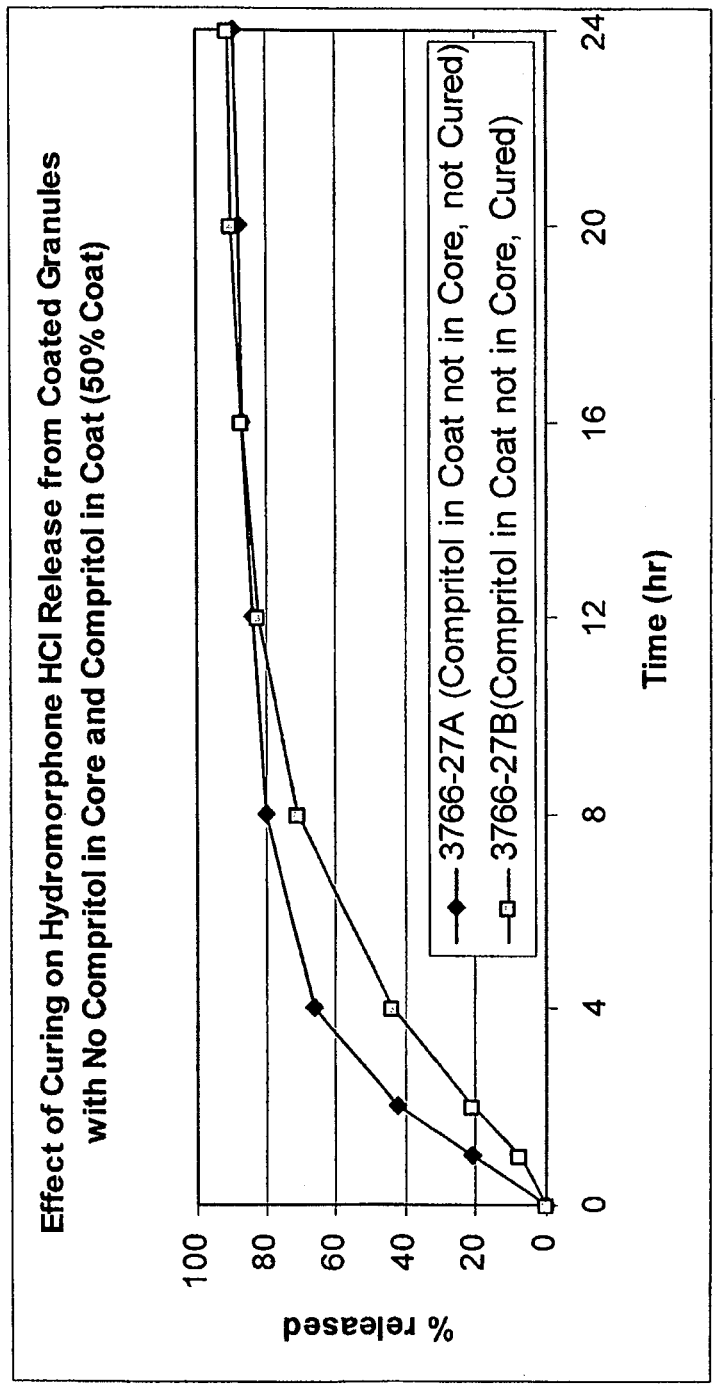
FIG. 40 illustrates the effect of curing on hydromorphone HCl release from coated granules with no compritol in core but compritol in coat (50% coat) where the shaded diamonds represent lot 3766-27A (compritol in coat not in core, not cured) and the open squares represent lot 3766-27B (compritol in coat not in core, cured).
Figure 41:
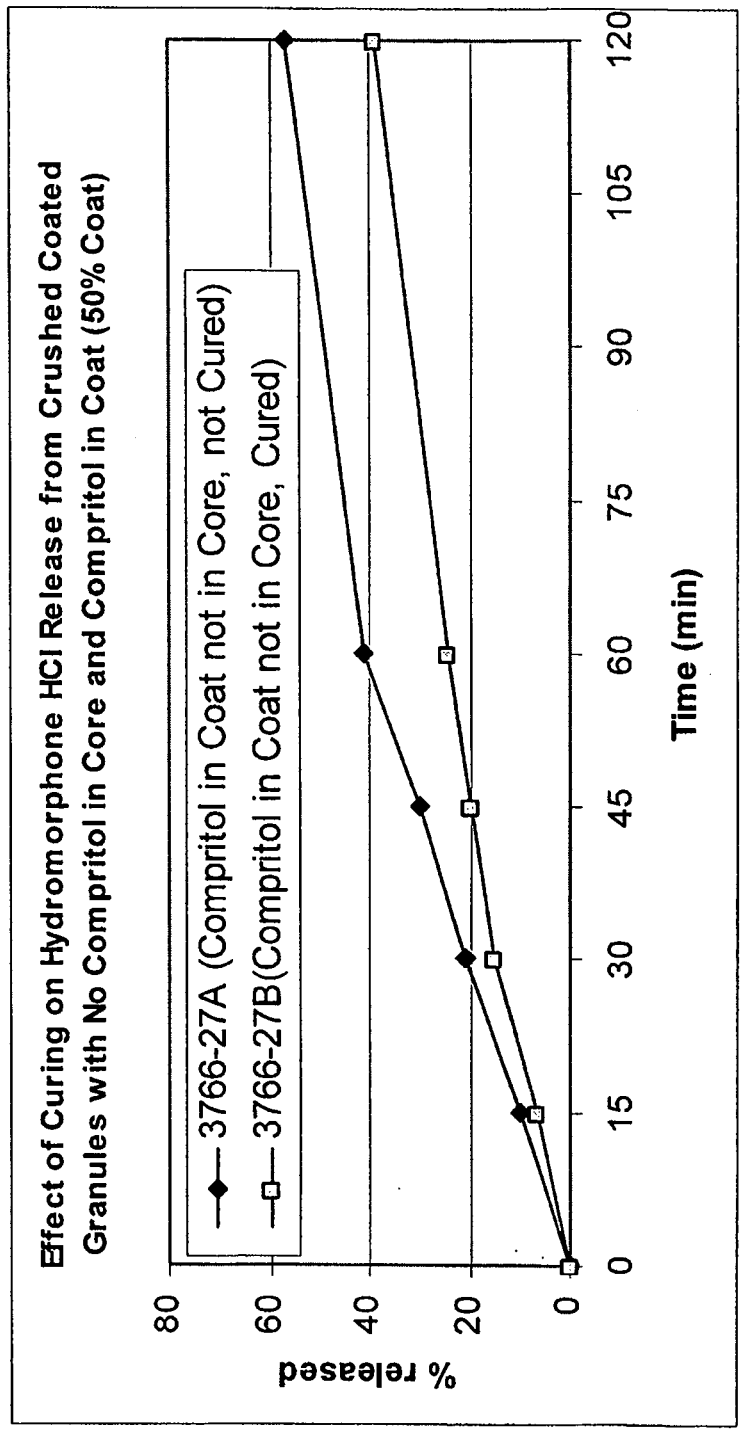
FIG. 41 illustrates the effect of curing on hydromorphone HCl release from crushed coated granules with no compritol in core but compritol in coat (50% coat) where the shaded diamonds represent lot 3766-27A (compritol in coat not in core, not cured) and the open squares represent lot 3766-27B (compritol in coat not in core, cured).
Figure 42:
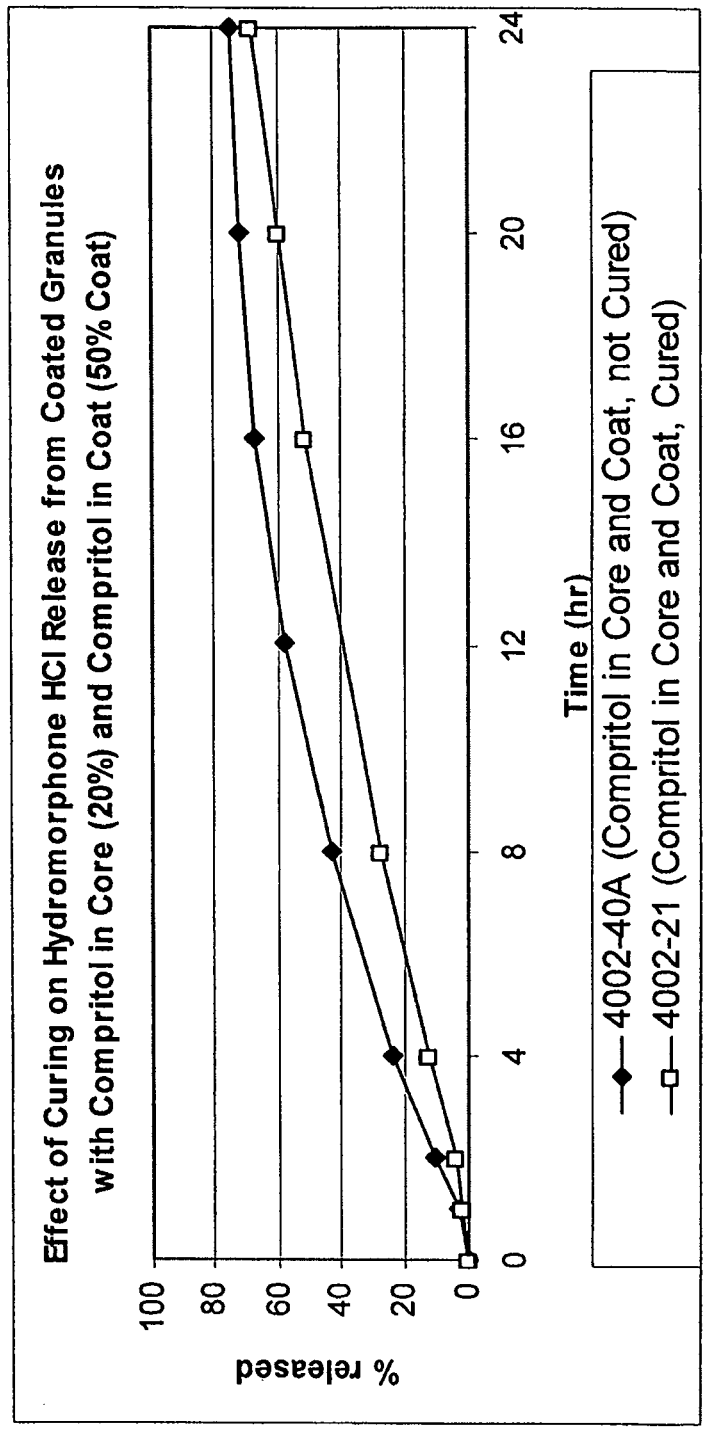
FIG. 42 illustrates the effect of curing on hydromorphone HCl release from coated granules with compritol in core (20%) and compritol in coat (50% coat) where the shaded diamonds represent lot 4002-40A (compritol in core and coat, not cured) and the open squares represent lot 4002-21 (compritol in core and coat, cured).
Figure 43:
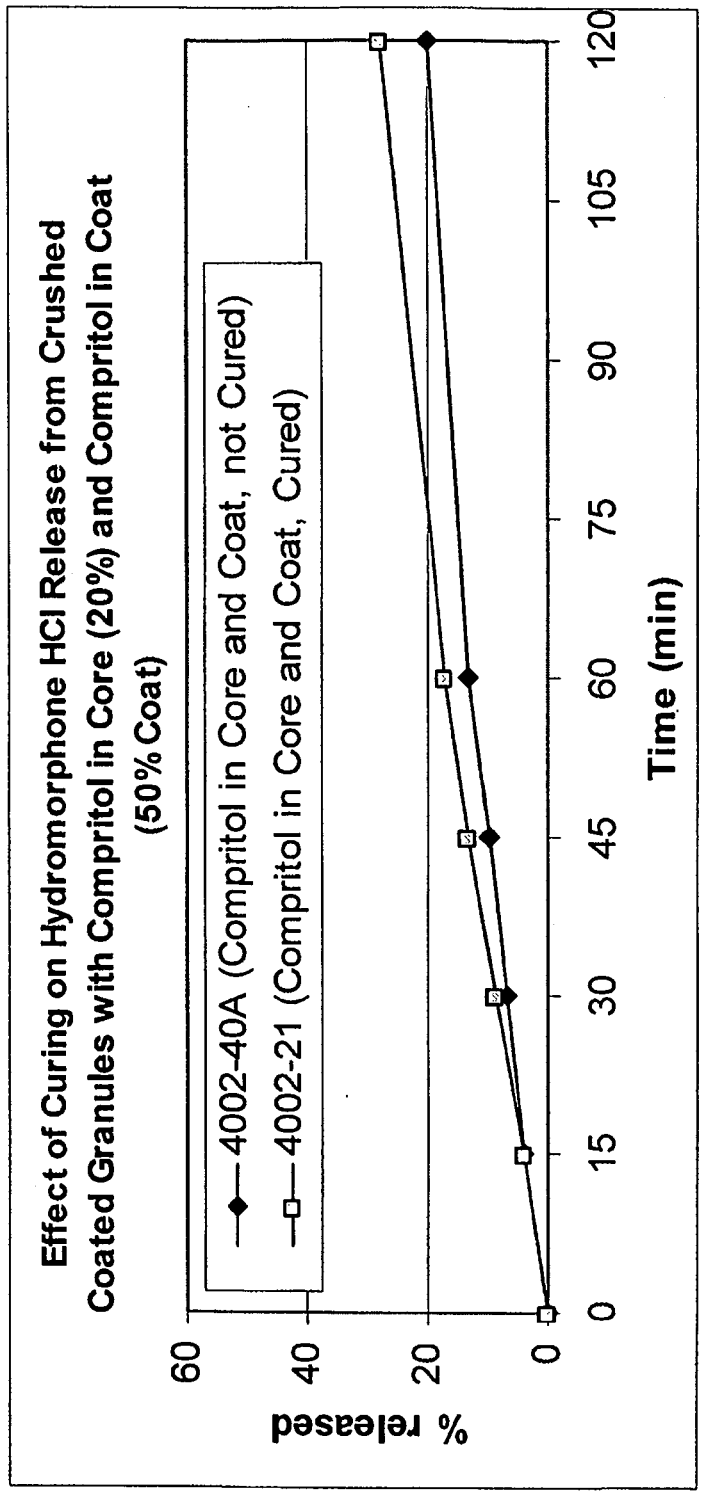
FIG. 43 illustrates the effect of curing on hydromorphone HCl release from crushed coated granules with compritol in core (20%) and compritol in coat (50% coat) where the shaded diamonds represent lot 4002-40A (compritol in core and coat, not cured) and the open squares represent lot 4002-21 (compritol in core and coat, cured).
Figure 44:
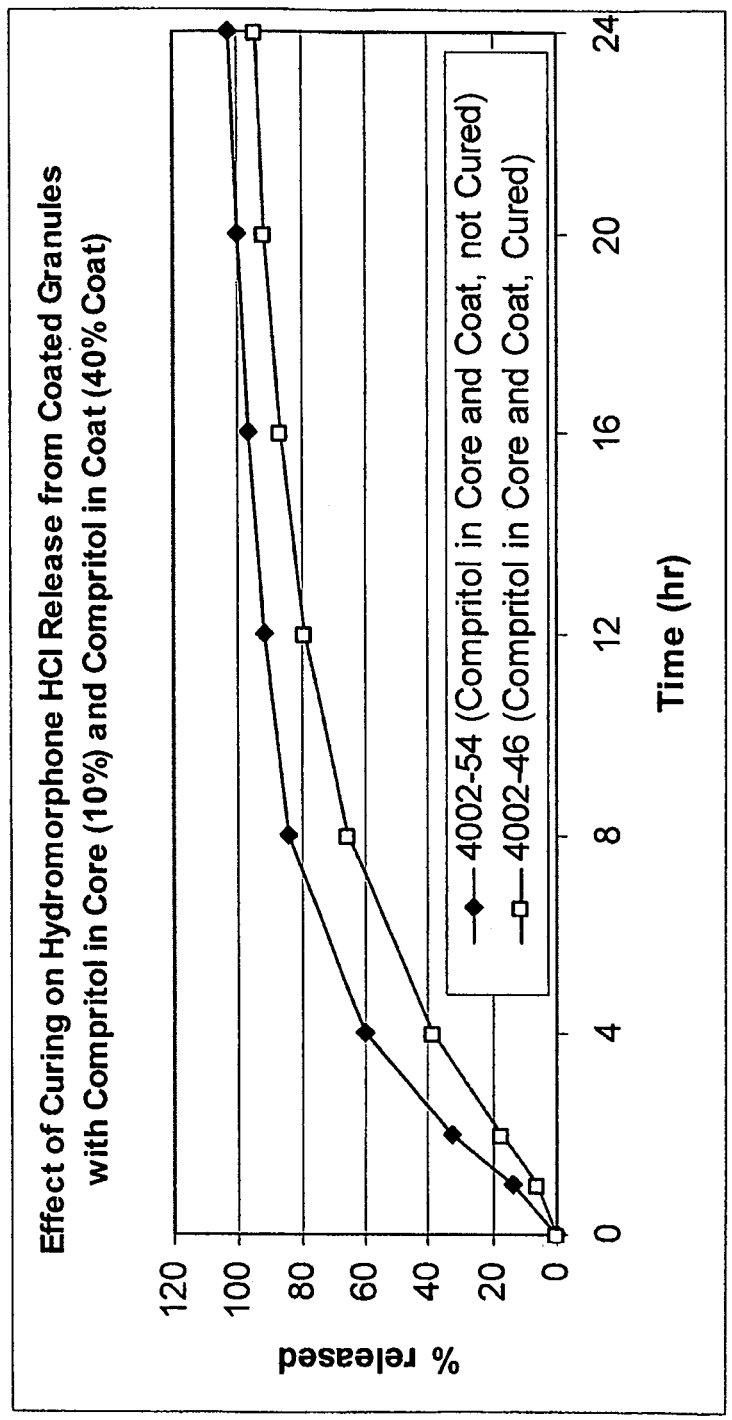
FIG. 44 illustrates the effect of curing on hydromorphone HCl release from coated granules with compritol in core (10%) and compritol in coat (40% coat) where the shaded diamonds represent lot 4002-54 (compritol in core and coat, not cured) and the open squares represent lot 4002-46 (compritol in core and coat, cured).
Figure 45:
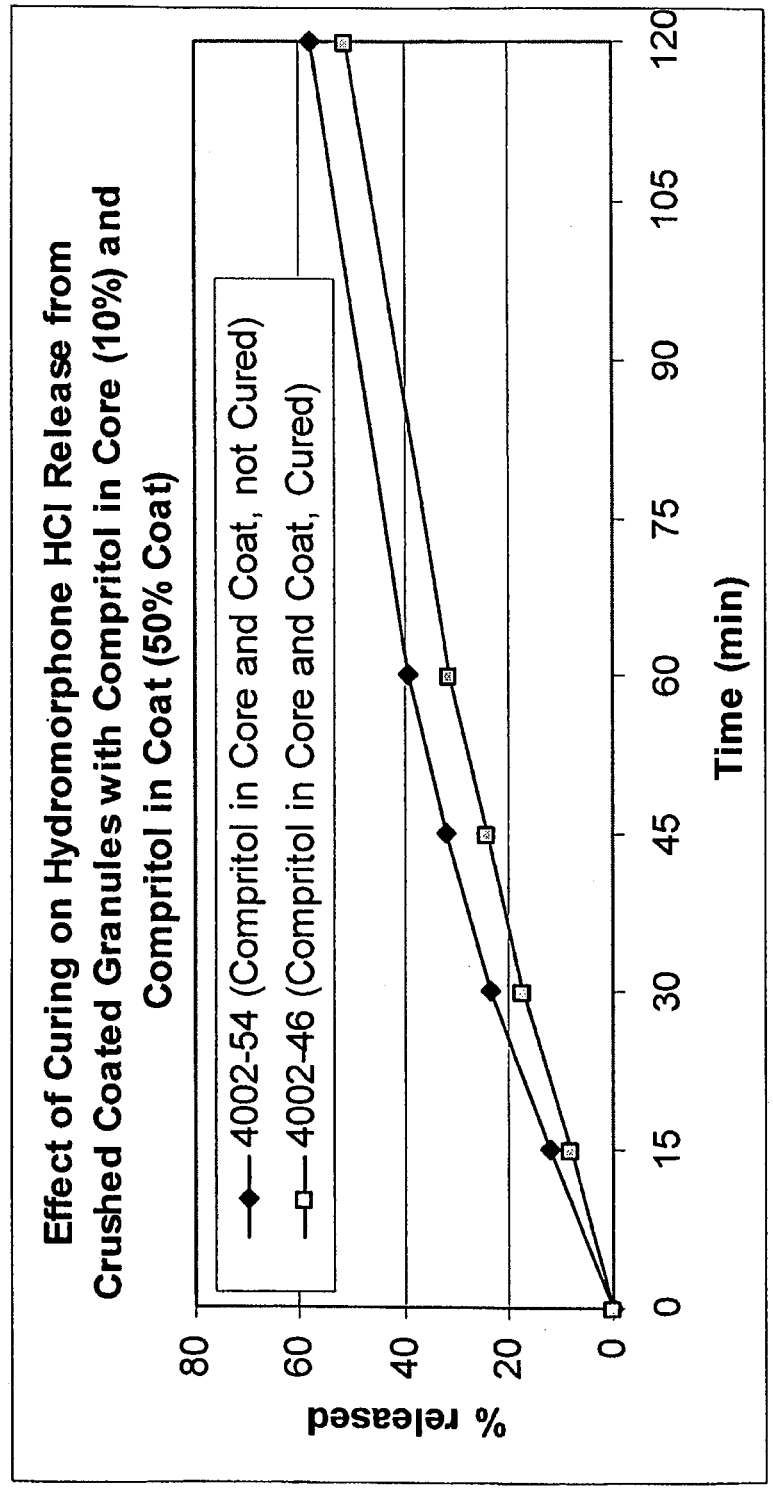
FIG. 45 illustrates the effect of curing on hydromorphone HCl release from crushed coated granules with compritol in core (10%) and compritol in coat (50% coat) where the shaded diamonds represent lot 4002-54 (compritol in core and coat, not cured) and the open squares represent lot 4002-46 (compritol in core and coat, cured).

Again, this was measured by the relative release of API detected after 30 minutes with the lower degree of release generally indicating better crush resistance. In addition, the use of a fat/wax-containing coating may provide some additional benefit in terms of the release of the API contained therein. Note that the first entry above is illustrated in FIG. 11 by the triangle, the fourth entry in Table 14 is illustrated in FIG. 11 as a diamond, and the last entry is illustrated in FIG. 11 with a square.

The fat/waxes used in the coating can be the same or different as those used in a particle. However, they should meet all of the same criteria and thus all of the materials previously identified as possible fat/waxes in connection with the particles may be used as such in the coatings as well. When used in the coating, the amount of fat/wax generally ranges from between about 5 to about 40, more preferably from about 10 to 30% by weight and most preferably 20-30%. This is based on the weight of the coated particle. Alternatively, the amount of fat/wax can be determined by its concentration or content in the coating liquid and the amount of coating liquid applied in the weight gain of the particles. The coating mixture or solution can contain between about 1 and about 10% by weight of a fat/wax. One exemplary formulation used in the examples included 10% ethylcellulose by weight, 5% fat/wax by weight and the balance was ethanol (commercial).

Generally, it is preferred that the controlled release material is ethylcellulose, meaning that it must be used in an amount that is capable of providing controlled release and crush resistance and should be applied from an alcohol based solvent. For controlled release, generally the amount of control release polymer coating material used in a coating is about 10 to 60, and more preferably about 20 to 50, and most preferably about 25 to 40. In addition, the API-containing particle may itself provide some measure of controlled release. For example, a wet granulate can be made from HPMC and ethylcellulose formulated using a water and alcohol solvent system. This material may itself provide some measure of crush resistance and/or controlled release.

In one embodiment, the use of the fat/wax containing coated particle the present invention will provide not more than about a 25% increase in API release measured at 5 minutes in a USP dissolution test as identified herein compared to an unstressed particle or dosage form which is of otherwise similar construction without the fat/wax. Note that this need not be limited to materials which can be applied from an alcohol base solvent or solution as described herein with regard to the crush resistant materials. Thus, for example, a layer of HPMC may be used to coat the API material followed by a coating layer of, for example, ethylcellulose. These may be applied from the same or from different solvent systems and may include the same or different additives.

As previously noted in connection with the particles, fat/waxes in coatings can be used in molten form. However, preferably, the fat/wax can be mixed into the coating material and applied, without applying molten material. When this practice is utilized, the fat/wax is generally added in a form of a solid, non-molten, particulate material having the same particle size ranges as for fat/waxes in the cores, namely particle sizes ranging from about 10 to about 100, more preferably from about 20 to about 80, most preferably about 30 to about 70 microns. This is measured by volume using a laser diffractometer. The fat/wax may be dissolved, suspended and/or dispersed in the coating material. Coatings may be applied by any known process, including but not limited to, spraying, dipping, pouring, spray drying, etc. It is also contemplated that the coating may be a single layer or multiple layers, having varying, or uniform crush-resistance layers.

The coating is ideally applied to the particles so as to substantially completely coat the particles with coating material. Of course, in practice, without checking each particle, one can not know that all particles are coated, that they are all coated to a specific thickness, and/or to a specific degree. Thus the degree of coating is inferred from analysis of the processes or resulting material in bulk.

Generally, however, it is preferred that the coating has a thickness resulting in an average weight gain of a particle of about 30% to about 300%, and more preferably about 50% to about 200%, and most preferably about 65% to about 150%. These numbers reflect any coating additives as part of the coating. These average weight gain values correspond to the coating material being present in an amount of between about 20 and about 75% by weight of coated particle or granulate, and more preferably 30 to 60% by weight of the coated particle or granulate.

Once coated with the coating, it is generally preferred that the coated API containing particles have an average particle size of about 300 to about 1200 microns, and more preferably about 400 to about 1000 microns, and most preferably about 500 to about 800 microns when tested by a sieve-shaking method by weight. In another preferred embodiment, the coated API containing particles preferably have a particle size distribution wherein no more than about 10% are less than 75 microns, and no more than 10% are larger than 1400 microns. Again, overs and unders could be discarded In one aspect of the products and processes of the present invention, the coated particles may be cured. Indeed, the particles themselves may be cured, then coated, and cured again. Alternatively, the particles may be cured, coated and not cured again, or the particles may be uncured, coated, and thereafter the coated particle cured. Preferably, however, two discrete curing steps take place. By "curing" it is understood that merely drying the particles or coated particles is generally insufficient. Curing transcends the application of energy at levels and times merely necessary to substantially remove surface water (generally to an amount less than 10%, more preferably less than about 5% by weight). Instead, curing is defined herein may be accomplished by heating the particles or coated particles in a fluidized bed until the temperature reaches melting point or range of the fat/wax used. Then the temperature is maintained at the fat/wax melting point/range +/−5° C. for at least 15 minutes. In the examples using compritol, 30 minutes at 70° C. was used, unless otherwise specified.

As can be shown from Table 14, for otherwise identical formulations, curing can, in some instances, provide additional benefits in terms of the relative length of API release and/or crush resistance. The first three compositions in Table 14 were granulates coated to a 50% coat with a coating material (this means that 100% weight percent of coating material was added relative to the weight of the uncoated granulate). The particles in the first entry used a coating with no compritol (magnesium stearate instead) and no curing. The second entry was a coated granulate with compritol and no curing. The third entry in Table 14 was the same coated granulate as in entry 2, however, the coated particle was cured. No curing was done on the uncoated only.

All three formulations included identical particles (46.6% hydromorphone HCl, 36.4% HPMC, 17.0% EC) and a 50% coat of 2:1 to ethylcellulose:(magnesium stearate or compritol 888) applied with an ethanol solvent (10% EC, 5% compritol, 85% ethanol (commercial). The coating without compritol or curing resulted in greater than 90% release in 8 hours (95%) while the uncured compritol coated granulate released 84% at 12 hours. The cured version improved release releasing 90% in 20 hours.

In addition, the release at 30 minutes following simulated tampering went from 44% to 21% to a low of 15% respectively. Thus, the cured compritol coated granulate provided the longest release and lowest release upon tampering—better than that resulting from a compritol containing coating without curing and about twice as good as the material without a fat/wax in either structure. In some instances, curing the particle and curing the coating may provide cumulative benefits. In other times, not. Note that when compritol was used in the granulate and not in the coating, there appeared to be no significant difference whether or not the core was cured (both released about 90% at 24 hours). However, the coated granulates both gave even longer release, and improved tamper performance over a core and coating without a fat/wax.

Table 15 provides data from the 11 lots of granulated/coated materials graphed in FIGS. 12-45 whose formulations are described in the examples. The same 11 lots of materials were used in all of the figures, although they were arranged differently for purposes of providing additional perspectives on the effect of the addition of a fat/wax to a core, coating or both, with and without curing. All of the cores were identical except that where indicated, cores included either 10 or 20 percent compritol 888 (Glyceryl behenate from Gattefosse (Paramus, N.J., USA).

TABLE 15

| Lot No. | Description | 4/8/16 hr release | 30 min abuse release |
|---|---|---|---|
| 3766-06B | Core*-No compritol and not cured**-Coating***-No compritol and not cured | 88%/95%/97% | 44% |
| 3766-33 | Core-20% compritol and not cured-Coating-no compritol and not cured | 35%/54%/79% | 28% |
| 3766-38 | Core-20% compritol and cured-Coating-no compritol and not cured | 24%/47%/78% | 29% |

TABLE 15-continued

| Lot No. | Description | 4/8/16 hr release | 30 min abuse release |
|---|---|---|---|
| 4002-40A | Core-20% compritol and not cured-Coating-compritol and not cured | 23%/43%/67% | 7% |
| 3766-27A | Core-No compritol and not cured-Coating-compritol and not cured | 66%/80%/87% | 21% |
| 3766-27B | Core-No compritol and not cured-Coating-compritol and cured | 44%/71%/87% | 15% |
| 4002-31B | Core-10% compritol and cured-Coating (50%)-compritol and cured | 13%/34%/61% | 6% |
| 4002-31A | Core-10% compritol and cured-Coating (40%)-compritol and cured | 41%/70%/91% | 15% |
| 4002-21 | Core-20% compritol and cured Coating compritol and cured | 12%/27%/51% | 9% |
| 4002-54 | Core-10% compritol and not cured-Coating-40% of compritol containing coating and not cured | 60%/84%/97% | 23% |
| 4002-46 | Core-10% compritol and cured-Coating-40% of compritol containing coating and cured | 39%/65%/87% | 17% |

*Cores were all particles of the invention which were wet granulates. Their compositions are in the examples. Percent compritol is reported by weight of the uncoated core.
**See examples.
***Note that all coatings in this table include 10% ethylcellulose, 5% of either compritol (where an entry says "compritol" in the coating), or magnesium stearate (otherwise) and 85% by weight ethanol when applied. All coatings were applied such that they made up about 50% by weight of the final weight of the coated particles (when dried) (about 100% weight gain based on the weight of the uncoated particles), except for 4002-46 and 4002-54 which were applied at a 40% coating level.

As can be seen from the above summarized data, some general trends can be observed. Curing slows the normal release no matter where the fat/wax is distributed. Its effect, however, can vary widely.

When a fat/wax is in the core or the coat only, curing tends to provide significant reductions in the release following simulated tampering by crushing. However, when a fat/wax is in both the core and the coating, curing does not appear to have as dramatic an effect on abuse resistance. Without a fat/wax in the core or the coating, performance of the granules included the highest level of release following simulated abuse testing at 30 minutes and an almost complete release by four hours. See lot 3766-06B. Adding a fat/wax to the core at a level of 20% provided significant improvement, not only in terms of a longer overall release, but in terms of a reduction in the amount of release at 30 minutes following simulated abuse testing. See lot 3766-33, 3766-38 (note that 4002-40A had Compritol in core and coat). Compritol alone in the coating, not in the core (cores coated to a 100% weight gain with a solution/suspension of 10% ethylcellulose, 5% compritol in 85% ethanol by weight) did not provide significant improvement in terms of release. See lots 3766-27A and 3766-27B. However, addition of the compritol to the coating, in this particular instance, generally provided significant improvement in terms of abuse resistance. Comparing lots 4002-40A and 3766-27B, it is clear that having a fat/wax in both the core and the coating is advantageous.

Indeed, even having a lower amount of compritol in the core can be advantageous. Lot 4002-31B included 10% compritol in the granulate which was cured and coated with a compritol containing coating which was also cured. However, as illustrated by lot 4002-21, 20% compritol in the core coupled with a coating with a fat/wax which was cured provided perhaps the best performance in terms of long term release and very similar 30 minute abuse resistance numbers when compared to a lesser amount of compritol in the core. The remaining lots 4002-54 and 4002-46 included a slightly lower amount of coating material and, in addition, lot 4002-46 had a cured granule and a cured coating.

It will be appreciated that in designing a particular dosage form for a particular API, it may not be desirable to maximize the length of release and/or crush or solvent resistance. Each product may need to meet unique criteria. Adding a fat/wax to both the core and coating and curing, while in some instances maximizing release and abuse resistance may be undesirable. However, the discoveries embodied in the present invention give the formulator much greater control and may allow for tailoring of a particular formulation without having to adjust other excipients or add additional structures. If the release is too long, one can remove the curing. If that is not sufficient, one can remove the fat/wax from either the particle or the coat. If thereafter the release performance is okay, but abuse resistance is insufficient, curing of the core could be used. And, fat/wax can also be added to the matrix or excipients blended with the coated particulate to improve characteristics as well. Similarly, the addition of a fat/wax to the matrix may provide solvent resistance. In some instances, however, an increase in one property may come at the expense of another. However, a balance of overall properties may be achieved.

The degree to which any particular change or combination of changes will affect any given formulation will need to be evaluated on a case-by-case basis. However, the present invention allows for relatively simple adjustments which can be quickly and decisively evaluated for any given active inexpensively and using standard equipment so as to arrive at an optimal balance of release and abuse resistance.

The coating may also, optionally, include one or more of the following: 1) channeling agents; 2) plasticizers; 3) antitacking agents); 4) antifoaming agents; 5) colorant; and 6) viscosity modifiers.

Channeling agents, also called pore formers, can be added into the coating by being either dissolved or dispersed in the solvent and preferably are inert and will not chemically alter the polymer used in the coating. They are intended to leach out from the coat upon exposure to aqueous media (stomach content/intestine) creating channels within the coat to facilitate the drug release process. This term and mechanism are well recognized, but may not reflect an accurate description of what is taking place. Nonetheless, these materials are known as channeling agents. When properly used, by whatever name or mechanism, they can alter API release.

Examples of channeling agents include salts like sodium chloride, sodium carbonates, bicarbonate, citrate, calcium phosphates, potassium chlorides etc, sugars like sucrose, glucose, lactose, mannitol, sorbitol, polymers like HPMC, MC, HPC, CMC, polyethylene glycol, poloxamer, PVP, polyacrylic acid, polyvinyl alcohol and graft or block copolymers of such polymers, and preferably poloxamers. These can be included at levels of 0-50% based on of the dry polymer weight of the coating material, more preferred 1-40% and most preferred 5-30%.

Antitacking agents, also called antiadherent or glidants or separating agents, are used to reduce tackiness and agglomeration during the coating process and may be used herein. Examples of these materials include: magnesium stearate, calcium stearate, stearic acid, talc, kaolin, and stearyltrimethyl ammonium chloride. When used, they may be used at levels of 0-100% based on the dry polymer weight of the coating materials, more preferred 20-80%, most preferred 20-50%. Preferred is magnesium stearate.

Plasticizers may also be used in the coating to lower the glass transition temperature of the polymer to improve the film formation process during coating or subsequent heat treatment. They also impart flexibility. They are added to the coating by being either dissolved or dispersed in the solvent. Examples of plasticizers include triethyl citrate, triacetin, polyethylene glycols, propylene glycol, acetyl triethyl citrate, acetyl tributyl citrate, dibutyl phthalate, diethyl phthalate, tributyl citrate, dibutyl sebacate, diethyl sebacate, castor oil, Myvacet 9-40, Glyceryl tributyrate. These may be used at levels of 0-150% based on the dry polymer weight of the coating, more preferred 1-50%, most preferred 5-30%.

Antifoaming agents in the coat may be used to reduce foam formation during coating solution/dispersion preparation process. Examples include silicon based antifoaming agent like Antifoam FG-10 made by Dow Corning. Antifoaming agents may be used at levels of 0-10% based on the polymer dry weight of the coating, 0.1-5% and 0.5-5%.

For product differentiation and aesthetic purposes, colorants may be used. Examples include FD&C and D&C lakes, titanium dioxide, magnesium carbonate, talc, pyrogenic silica, iron oxides, channel black, natural colorants and insoluble dyes. Colorants which may be used in an amount of 0-25% of the polymer dry weight of the coating, 0.5-10, 1-5%.

To reduce the polymer solution/dispersion viscosity while maintaining high polymer content to facilitate the coating process, viscosity modifiers may be used. Their level must be carefully selected to reduce the viscosity without any detrimental phase separation. Examples of these materials include salts with high order in the hofmeister's series including sodium citrate and sodium chloride which may be used at levels of 0-0.1 mol/liter of the coating solution/dispersion, more preferred 0.001-0.05, most preferred 0.005-0.03 mol/L, based on the weight of the coating.

The compositions and dosage forms of the invention may be used therapeutically alone or with additional excipients. These can be taken as a powder, sprinkled on food such as apple sauce, loaded into capsules, or compressed into a tablet dosage form. However, it has been found that the addition of a fat/wax to a dosage form which also includes a fat/wax-containing coated particle of the present invention can provide additional benefits in terms of release and/or abuse resistance. In particular, the use of a fat/wax in the blended with the coated particles of the invention can provide solvent resistance. However, it may in addition or instead provide advantages in crush resistance and/or controlled release.

The fat/wax may be used alone as the matrix or, along with other excipients, may comprise the matrix which makes up the balance of any composition or dosage form (over and above the coated particulate of the invention). In this context, "matrix" broadly means the balance of the composition or dosage form. The fat/wax may be used in any form, but in some instances may be used in the form of a second particulate.

The second particle containing the fat/wax material can be provided in an amount of from about 1% to about 50% per dosage form unit (e.g., tablet). Preferably, the dosage form unit can contain from about 2.5% to about 30% fat/wax-containing particles per unit, most preferably from about 5% to about 25%, per total dosage form unit. These weight percentages are also for the weight percentage in the pre-dosage form composition, which would contain weight percentages equal to the final dosage form. The fat/wax particles in the matrix may be selected from the same materials identified for the fat/wax found in the coated particles and may have the same particle sizes.

It may be possible to modify the active-to-fat/wax ratio to provide the optimal effect with regard to the potential chemical solvent resistance properties of the dosage form. Balancing chemical or solvent resistance versus desired delayed release parameters of the dosage form should also be considered. Accordingly, two general factors may be involved: first, the thickness and type of coating material employed; and second, the amount of fat/wax particles in the dosage form. In other words, release of active ingredient could be controlled by modifying the coating/extended release material in combination with the dual particle system which might create a tortuous path that delays the chemical or solvent access to the first active particle hence drug diffusion. Variations in these factors affect the chemical resistance and delayed release parameters, in addition to physical tampering/crush resistance.

The first particles containing the API and fat/wax and the second particle containing the fat/wax material can be combined to form mixtures of particulate prior to forming the resulting dosage form. Additional or secondary ingredients or excipients can be combined as part of the process of preparing the resultant dosage form, e.g., tablet. For example, the dosage form formulation can include spray-dried lactose and EMCOMPRESS (dibasic calcium phosphate dihydrate).

Dosage forms of this aspect of the invention can be prepared according to any process. In one embodiment, however, the following process is used. To prepare the first particle of the composition of the invention, the API and fat/wax can be mixed with polymers in a granulator first as a dry mix. Then, a polymer solution can be added to the mix, and the process continues while adding the solution until granulation is achieved. The resulting granules can be partially dried until the desired loss of drying value is reached for the given formulation. The granules can then be milled in a granular mill and then dried to a LOD of less than 5%, for example. These particles may, instead or in addition, be cured.

Next, the granules can then be coated (with ethylcellulose in ethanol solution, for example) and with magnesium stearate or Compritol in a bottom spray fluid bed, until the desired coat level is obtained. The granules can then dried and optionally cured and can be mixed together with the second particles of fat/wax and other excipients to form a common blend. This can then be metered or measured into discrete amounts and packaged, filled, and/or tableted.

While at least one API is required, it is contemplated that multiple APIs may also be used. "API", or Active Pharmaceutical Ingredient, in accordance with the present invention include materials capable of being particles, materials likely to be abused by people, or otherwise useful in the present invention. Such active ingredients may include systematically distributable pharmaceutical ingredients, vitamins, minerals, dietary supplements, as well as non-systemically distributable drugs. A combination or mixture of any of the foregoing is also contemplated by the present invention. Pharmaceutical ingredients may include, without limitation, antacids, analgesics, stimulants, sleep aids, hypnotics, antipyretics, antimicrobials, anxiolytics, laxatives, antidepressants, antidiuretics, antiflatuants, antispasmodics, anti-inflammatory, antibiotics, diuretics, anorexics, antihistamines, antiasthmatics, antidiuretics, antiflatuents, antimigraine agents, antispasmodics, sedatives, antihyperactives, antihypertensives, tranquilizers, decongestants, immunosuppressants, anticancers, antivirals, antiparasitics, antifungals, antiemetics, antidepressants, antiepileptics, local anesthetics, vasoactive agents, antiasthmatics, skeletal muscle relaxants, drugs for parkinsonism, antipsychotics, hematopoietic growth factors, antihyperlipidemics, anticoagulants, fibrinolytics, antithrombotics, hormones, therapeutic proteins and peptides, antiarrhythmia, antiangina, beta blockers and combinations thereof. Also included as API's in accordance with the present invention are the drugs and pharmaceutically active ingredients described in Mantelle, U.S. Pat. No. 5,234,957, in columns 18 through 21. That text of Mantelle is hereby incorporated by reference. In one embodiment in accordance with the present invention, the APIs are preferably pharmaceutical agents having a high likelihood of abuse by people. In another preferred embodiment of the present invention, the API is a pain medication such as an a narcotic or non-narcotic analgesic as listed on pages THER-2 and THER-3 of The Merck Index, 13th Ed., Published by Merck & Co., Inc., of Whitehouse Station, N.J., copyright 2001, which is hereby incorporated by reference. The narcotic analgesics include, but are not limited to, analgesics, pain relievers, opioids such as oxycodone, codeine, hydrocodone, morphine, hydromorphone, oxymorphone, methadone, propoxyphene, meperidine, fentanyl, buprenorphine, butorphanol, dezocine, levomethadyl acetate, levorphanol, nalbuphine, pentazocine, remifentanil, sufentanil, tramadol; Stimulants like amphetamine, methamphetamine, dexamphetamine, methylphenidate, dexmethylphenidate, pemoline; Sedative and hypnotics including barbiturates as amobarbital, aprobarbital, butabarbital, mephobarbital, phenobarbital, secobarbital; benzodiazepines such as alprazolam, clonazepam, diazepam, estazolam, flurazepam, halazepam, lorazepam, midazolam, quazepam, temazepam, triazolam, prazepam, oxazepam, other drug classes include modafinil and armodafinil. Particularly preferred APIs include oxycodone, fentanyl and hydromorphone. Salts of all of the API's are also contemplated as are their stereogenic isomers, polymorphs and solvates.

As used in this disclosure, the term "vitamin" refers to trace organic substances that are required in the diet. For the purposes of the present invention, vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes that may be useful in the present invention include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

The amount of API in the composition can vary greatly. In terms of the proportion of the uncoated particle that is API, that can range from about 0.1% to about 90% by weight of the uncoated particle or granulate, and more preferably in an amount of about 1% to about 80% by weight, and most preferably in an amount of about 20% to about 60% by weight of the uncoated particle. In terms of the proportion of the coated particle, the amount of the drug can range from about 0.1% to about 75% by weight of the coated particle, and more preferably in an amount of about % to about 607% by weight, and most preferably in an amount of about 10% to about 40% by weight of the coated particle.

The amount of granulates and/or coated particles within a dosage form can vary greatly and can depend upon, among other things, the type and properties of the API, the density, friability, hardness, etc. of the API particles, the condition it is intended to treat or prevent, the size, weight, age, and condition of the patient, the amount and size of other ingredients, the size of the coated particles, the overall composition, the size and nature of the dosage form, the number of dosage forms per dose, whether or not more than one API is to be delivered from the dosage form, etc. It is preferred that the dosage form provide a therapeutically effective amount of at least one API to a patient in need thereof. The coated particles are preferably present in one or more dosage forms in an amount sufficient to provide a therapeutically effective amount the at least one API. A "therapeutically effective amount" is the amount or quantity of an API or active ingredient which is sufficient to elicit the required or desired therapeutic response, or in other words, the amount which is sufficient to elicit an appreciable biological response when administered to a patient. The dosage need not be optimal, nor even provide a cure or symptomatic relief. Generally, the total amount of coated particles for any individual dosage form is an amount which is capable of providing between about 10 micrograms and about 2 grams of API per dosage form, more preferably from about 0.1 milligram and about 1 gram of API per dosage form and even more preferably from about 1 milligram to about 800 milligrams per dosage form. Therefore, an amount of coated particulate sufficient to provide that amount of API per dosage form will be necessary. Understandably that amount will vary because of the factors discussed previously. As a nonlimiting example, twice as much of a particulate having a 25% by weight API load would be needed to provide the same amount of API, in an otherwise identical tablet, having particles with a 50% load of API.

As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA.

It is contemplated that the composition of the present invention may also include at least one other ingredient or excipient in addition to the API-containing coated particle and optionally any fat/wax in the extra-particulate matrix. The other ingredient or excipient may include, but are not limited to, other APIs, taste masking agents, binders, fillers, sugars, artificial sweeteners, polymers, flavoring agents, coloring agents, lubricants, glidants, bio- or muco-adhesives, viscosity modifiers, surfactants, buffers, disintegrants etc. The amount of any one or more of these ingredients will vary with the amount of CR coating (including ethylcellulose), additional polymers, API, API particle size, and shape of the dosage form, form of the dosage form, how many ingredients are used, which ingredients are used, the number of dosage forms that will make-up a dose, the amount of API per dose and the like. Any combination or amounts are contemplated sufficient to allow the creation of a crush-resistant, solvent-resistant, storable dosage form in accordance with the present invention.

"Taste masking agent(s)" in accordance with the present invention include anything known to be used as a taste masking agents in this art. Preferred taste masking agents in accordance with the present invention may include Eudragit E-100, ethylcellulose, hydroxypropylmethylcellulose, hydroxypropyl cellulose, methylcellulose, Hydroxyethylcellulose, carboxymethylcellulose, shellac, zein, carbomers, fats, waxes, glycerol mono-, di-, tri-glycerides, Compritol, Precirol, gelucires, poloxamers, modified chitosans, carrageenans, cellulose acetate trimellitate, hydroxypropyl methylcellulose phthalate, hydroxypropylmethylcellulose acetate succinate, methacrylic acid copolymers including Eudragit L 100, S 100, L30D-55, polyvinylacetate phthalate (PVAP). Taste masking agents can be used in conventional amounts and preferably in an amount of about 0 to about 50% by weight of the total dosage form, and more preferably in an amount of about 5% to about 40% by weight of the total dosage form, and most preferably in an amount of about 10% to about 30% by weight of the total dosage form.

Binders can be anything known to be used as binders. These materials are used to add cohesiveness to powders and provide the necessary bonding to form granules that can be compressed into hard tablets that have acceptable mechanical strength to withstand subsequent processing or shipping and handling. Some binders that may be useful in the present invention include acacia, tragacanth, gelatin, starch (both modified or unmodified), cellulose materials such as methylcellulose, ethylcellulose, hydroxypropylmethylcellulose, hydroxypropyl cellulose, Hydroxyethylcellulose and sodium carboxy methylcellulose, alginic acids and salts thereof, magnesium aluminum silicate, polyethylene glycol, guar gum, polysaccharide acids, bentonites, sugars, invert sugars, and the like, fats, waxes, polyvinylpyrrolidone, polymethacrylate and other acrylic and vinyl-based polymers. Binders can be used in conventional amounts and preferably in an amount of about 0 by weight to about 50 and more preferably about 2 to about 10 percent by weight of the total dosage form.

Fillers can be anything known to be used as fillers. Some fillers that may be useful in the present invention include mannitol, dextrose, sorbitol, lactose, sucrose, and calcium carbonate. Fillers can be used in conventional amounts and preferably in an amount of about 0 to about 90, and more preferably about 10 to about 50.

A particularly preferred type of filler which may be used is sugars. Sugars that may be used in the present invention include sugar, sugar alcohols, ketoses, saccharides, polysaccharides, oligosaccharides and the like, as well as celluloses and modified celluloses.

Sugars may also include direct compression and/or nondirect compression sugars. Particularly preferred nondirect compression sugars include, without limitation, dextrose, mannitol, sorbitol, trehalose, lactose and sucrose. Of course, these sugars generally exist as either a direct compression sugar, i.e., a sugar which has been modified to increase its compressibility and/or flow, or a nondirect compression sugar which does not have sufficient flowability and/or compressibility to allow it to be used in high speed processing and multi-tablet presses without some sort of augmentation such as, without limitation, a glidant to increase flow, granulation to increase flow and/or compressibility and the like. Of course, techniques like granulation can also be used to convert something which initially has sufficient flow and compressibility to be considered a direct compression sugar before processing into a nondirect compression sugar as well. This can be measured by directly compressing tablets made only from a sugar and comparing the flow and compressibility both before and after processing. If flow and/or compressibility are reduced after processing the material is likely to have become a nondirect compression sugar. It will be appreciated however, that whether or not the reduction in properties are sufficient to require augmentation or further processing before the sugar is used in a commercial process will depend on a number of factors including the amount used, the type of processing equipment used, and the overall formulation. Generally, however, some further processing or augmentation is required. While not definitive, sometimes a nondirect compression sugar will have at least about 90% of its particles smaller than about 200 microns, and more preferably 80% smaller than about 150 microns.

The amount of total sugar can range from about 0 to about 90. More preferably, the amount of sugar will range from about 5 to about 75, and even more preferably between about 10 and 50. Other non-carbohydrate diluents and fillers which may be used in accordance with the present invention include for example dihydrated or anhydrous dibasic calcium phosphate, tricalcium phosphate, calcium carbonate, anhydrous or hydrated calcium sulphate, and calcium lactate trihydrate. When used these are present in an amount of ranging from 0 to about 90, more preferably from about 5 to about 75 and most preferably from about 10 to about 50% by weight of the dosage form.

Artificial sweeteners can be anything known to be used as artificial sweeteners. Some artificial sweeteners that may be useful in the present invention without limitation include saccharin, aspartame, sucralose, neotame, and acesulfame potassium. Artificial sweeteners may be used in conventional amounts, and preferably in an amount ranging from about 0.1 to about 2.

Flavoring agents can be anything known to be used as flavoring agents. Flavoring agents that may be useful in the present invention may include synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavoring agents are vanilla, citrus oil, including lemon, orange, banana, grape, lime and grapefruit, and fruit essences, including apple, pear, peach, strawberry, raspberry, cherry, plum, pineapple, apricot and so forth.

Flavoring agents may be used in conventional amounts, and preferably in an amount ranging from about 0.01% to about 3% by weight of the dosage form, and more preferably from about 0.1% to about 2.5% by weight of the dosage form, and most preferably from about 0.25% to about 2% by weight of the dosage form.

Coloring agents can be anything known to be used as a coloring agent. Coloring agents useful in the present invention may include titanium dioxide, and dyes suitable for food such as those known as F.D.& C. dyes and natural coloring agents such as grape skin extract, beet red powder, beta-carotene, annatto, carmine, turmeric, paprika, etc. Coloring agents may be used in conventional amounts, and preferably in an amount ranging from about 0.001% to about 1% by weight of the dosage form.

Lubricants can be anything known to be used as a lubricant. Lubricants that may be useful in the present invention may include intrinsic or extrinsic lubricants. Intrinsic lubricants may include magnesium, calcium, zinc salts of stearic acid, hydrogenated and partially hydrogenated vegetable oils, animal fats, polyethylene glycol, polyoxyethylene monostearate, talc, light mineral oils, sodium benzoate, sodium lauryl sulphate, magnesium oxide and the like. Lubricants may be used in conventional amounts, and preferably in an amount from about 0.1% to about 5% by weight of the dosage form, more preferably from about 0.25 to about 2.5 and most preferably from 0.5 to 2%.

Viscosity modifiers can be anything known to used as a viscosity modifier. Some viscosity modifiers that may be useful in the present invention include, without limitation, sodium alginate, hydroxypropyl methylcellulose (HPMC), hydroxyethylcellulose (HEC), sodium carboxymethycellulose (sodium CMC), polyvinylpyrrolidone (PVP), Konjac flour, carrageenan, xanthan gum, other hydrophilic polymers, or mixtures thereof. Viscosity modifiers can be used in conventional amounts and preferably in an amount of about 1 to about 40, and more preferably in an amount of about 2 to about 20 by weight of the dosage form.

Surfactants can be anything known to be used as surfactants. Some surfactants that may be useful in the present invention include, without limitation, various grades of the following commercial products: Arlacel®, Tween®, Capmul®, Centrophase®, Cremophor®, Labrafac®, Labrafil®, Labrasol®, Myverol®, Tagat®, and any non-toxic short and medium chain alcohols. Surfactants can be used in conventional amounts and preferably in an amount of about 0.01 to about 5, and more preferably in an amount of about 0.1 to about 2 by weight of the dosage form.

Buffers can be anything known to be used as a buffer. Some buffers that may be useful in the present invention include any weak acid or weak base or, preferably, any buffer system that is not harmful to the gastrointestinal mucosa. These include, but are not limited to, sodium carbonate, potassium carbonate, potassium carbonate, disodium hydrogen phosphate, sodium dihydrogen phosphate, and the equivalent potassium salts. Buffers can be used in conventional amounts and preferably in an amount of about 0.1 to about 10, and more preferably in an amount of about 1 to about 5 by weight of the dosage form.

Disintegrants which may be used include starch, cellulose, modified starch, microcrystalline cellulose, alginic acid, clays, veegum and super disintegrants including, without limitation, cross-linked PVP, croscaramellose salts such as croscaramellose sodium, starch derivatives like sodium starch glycolate.

Where such super disintegrants are used, they are traditionally found in an amount of between about 1 and about 20%, more preferably between about 2 and about 10%, and most preferably between about 2 and about 5% by weight of the finished dosage form. In addition to, instead of any portion of, or instead of any super disintegrant, the dosage forms in accordance with the present invention may include at least one effervescent couple or disintegrant.

Effervescent couples are made from a reaction of a soluble acid source and a metal carbonate or bicarbonate. The acid sources or acid may be any which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations of the present invention were intended to be dissolved in a glass of water. Acid anhydrides and acid salts of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. These effervescent couples may be provided in an amount of between about 3% and about 50% by weight of the dosage form, more preferably between about 3% and about 25% by weight.

Nonlimiting examples of such noneffervescent disintegration agents include: microcrystalline, cellulose, starches, corn starch, potato starch and modified starches thereof, clays, such as bentonite, alginates, gums such as agar, guar, locust bean, karaya, pecitin and tragacanth. These disintegrants may comprise up to about 20 weight percent and preferably between about 2% and about 10% of the total weight of the dosage form.

If desired the dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

A "dosage form" in accordance with the present invention is a tablet, capsule, caplet, sachet, powder or other solid known for the administration of medicines orally. It is generally made from a mixture as defined herein and is either formed (as in a tablet) or packaged (as in a capsule, powder, or sachet) into a form for use by a doctor or patient for administration. A tablet can be an ALKA-SELTZER®-like tablet which is dropped into a glass of a liquid and dissolved prior to ingestion, a dosage form which is orally disintegrable/dissolvable on a patient's tongue, a dosage form which is to be administered gingivally, buccally or sublingually, or a traditional dosage form which is to be swallowed as a dispersion, suspension or slurry. An orally disintegrable/dissolvable dosage form is one which is placed on the tongue and which dissolves/disintegrates in the mouth generally in about 90 seconds or less, more often in about 60 seconds or less. Thereafter, the resulting suspension, solution or slurry is swallowed. In buccal, gingival and sublingual dosage forms, the active ingredient is typically transferred through the oral mucosa. A dosage form could be prepared by metering powder or slugged cores into a hard gelatin capsule for oral ingestion or provided as a powder to be taken directly, to be sprinkled onto food, or mixed with a beverage prior to ingestion are also contemplated.

Dosage forms as contemplated by the present invention may be provided in a range of shapes and sizes. In a preferred embodiment, the dosage form is in a size capable of oral administration and provides a therapeutic amount of the API therein. Generally, such dosage forms will be less than 1.5 inches in any one direction, more preferably less than 1 inch and most preferably less than 0.75 inch. Shapes include but not limited to round with both flat or convex face, capsule shape (caplets), diamond shape, triangular, rectangular, hexagonal, pentagonal, heart-shaped, animal shaped tablets like rabbits, elephants etc. Dosage forms can be any size and shape, but preferable of a size and shape to avoid crushing or abuse.

The frequency of dosing depends on various factors including the amount of active ingredient present in the dosage form, the size of the dosage form, the weight of the patient, the number of dosage form per dose, the condition of the patient, side effects of the active ingredient, etc. The administration of multiple dosage forms and multiple frequency of dosing is contemplated depending upon the above factors as well as duration of the patient's condition, how long the active ingredient stays in a patient's system, etc., however, dosage 4 times per day of fewer are desirable. Most preferably, dosing is 1, 2, 3, or at least 4 times per day.

In some embodiments tablets the invention often have a hardness of about 20 Newtons or less, and in other embodiments 20-250 Newtons. In one embodiment, hardness is about 20 to about 40 Newtons and a friability of less than 1% as measured by the U.S.P. method as of the filing date.

Tablets can either be manufactured by direct compression, wet granulation, dry granulation or any other tablet manufacturing technique. See, e.g., U.S. Pat. Nos. 5,178,878, 5,223,264 and 6,024,981 which are incorporated by reference herein.

In another aspect, the present invention comprises an abuse resistant dosage form in accordance with the present invention and one or more indicia indicating that it is abuse resistant. In one embodiment, the dosage form itself includes the indicia. The indicia could be, for example, one or more letters such as "AR," one or more words such as "abuse" and/or "resistant" or a picture or symbol. These can be printed onto the surface of the dosage form, imbedded as a relief or as a raised structure. Instead, or in addition, the abuse resistant dosage forms of the present invention may be packaged in one or more blister packs, or in multi-tablet openable and reclosable containers, such as a bottle. The packaging, or any associated product label or package insert could also include one or more letters, words, pictures or symbols which indicate that the dosage forms were abuse resistant.

Such indicia could provide additional assistance in reducing abuse in a number of ways. For one thing, a patient who is informed of the abuse-resistant feature and insists on another form of the drug could alert a pharmacist that the patient could have a problem. Second, knowing that the dosage forms are abuse resistant could reduce their theft or their illegal resale as they would be less desirable to abusers.

EXAMPLES

Example 1

Coated Granules Lot 2926-76C

The present invention can be illustrated by producing controlled release coated particles with wet granules as API particles.

TABLE 1

Granules Formulation

| Component | % (w/w) |
|---|---|
| Oxycodone Hydrochloride | 27.8 |
| Hydroxypropyl methylcellulose 844 | 46.3 |
| Ethylcellulose | 25.9 |

TABLE 2

Coated Granules Formulation

| Component | % (w/w) |
|---|---|
| Oxycodone Granules | 50.0 |
| Ethylcellulose | 33.3 |
| Magnesium Stearate | 16.7 |

Granules were manufactured in a high shear granulator where oxycodone hydrochloride, HPMC 844 and 71% of the total amount of ethylcellulose were dry mixed for 2 minutes. Then, a 10% hydro-ethanolic (30:70) solution of ethylcellulose was slowly added while maintaining the granulator impeller and chopper speeds at pre-selected values to provide enough shear for granule formation and growth. Solution addition was continued until the aforementioned percentage of ethylcellulose was realized. The granules were subsequently dried in a fluid bed to a level that renders them suitable for milling. The granules were then milled in a granu-mill and finally dried.

The prepared granules were then coated in a bottom spray fluid bed using a 15% alcoholic suspension of ethycellulose and magnesium stearate (2:1). Average particle size was determined by a sieve shaking method, and equaled about 630 microns. This is the geometric mean diameter, the number 630 was obtained by manually plotting the cumulative % frequency against the particle size on a Log-probability paper. The dissolution profile of these coated granulates were tested (FIG. 1).

Figure 2:
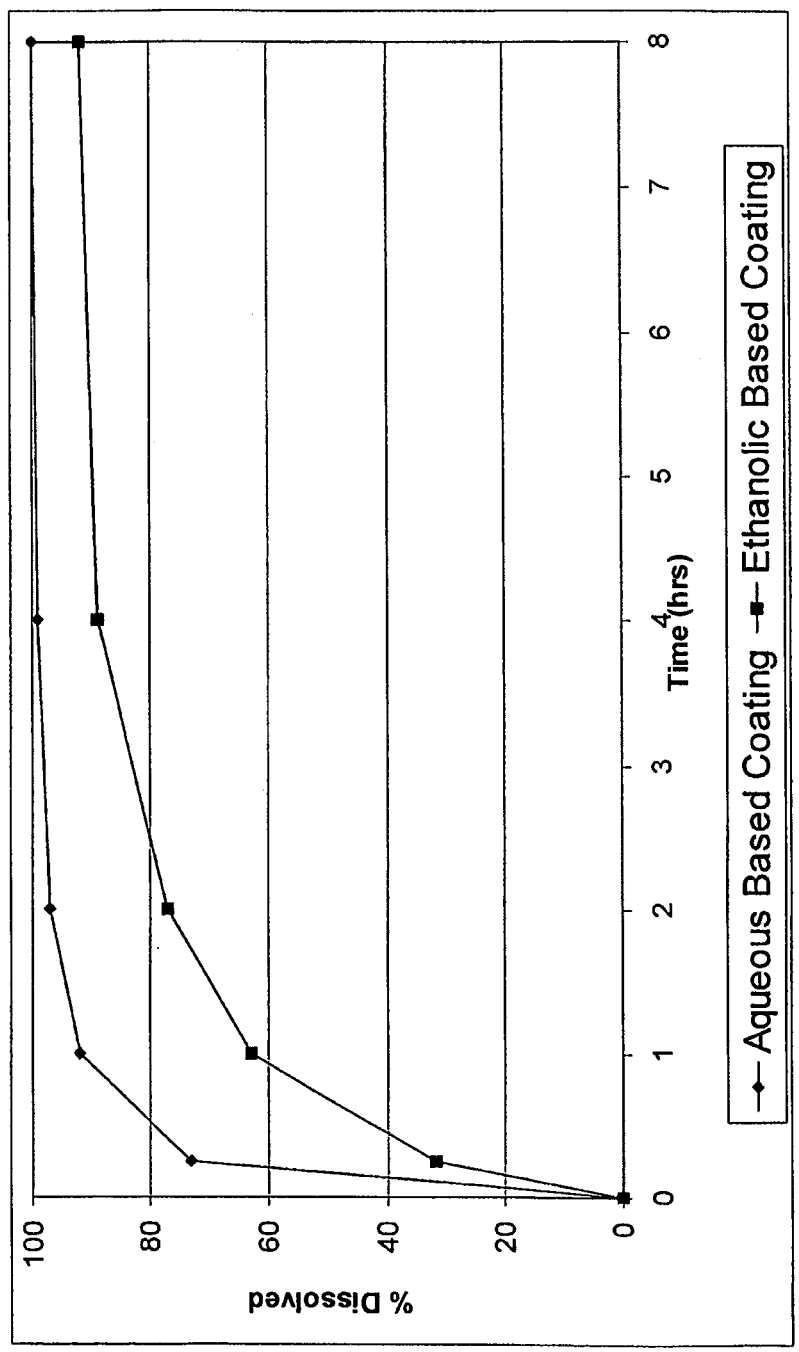
FIG. 2 illustrates comparative dissolution profiles for various coated granules with and without a crush resistant coating in accordance with Examples 1 and 2 of the present invention after crushing.

Aliquots of a sample were crushed using a mortar and pestle, crushing in 12 circular strokes of the pestle. The aliquots were pooled and then divided into aliquots each contains a drug amount equivalent to a single dose. The aliquots are tested for dissolution in 500 mL of medium (0.1N HCl). At specified time points, 5 mL aliquots were pulled from each vessel and analyzed via HPLC versus a standard. The results are shown in FIG. 1 for the uncrushed coated particles and FIG. 2 for the "crushed" coated particles and in both plots, the dark squares indicate the measured data points.

Example 2

Coated Granules Lot 2926-76B

The methods of making coated particles, described above in Example 1 were employed again except the formulation was coated with the aqueous EC dispersion.

TABLE 3

Granules Formulation

| Component | % (w/w) |
|---|---|
| Oxycodone Hydrochloride | 27.8 |
| Hydroxypropyl methylcellulose 844 | 46.3 |
| Ethylcellulose | 25.9 |

TABLE 4

Coated Granules Formulation

| Component | % (w/w) |
|---|---|
| Oxycodone Granules | 50.0 |
| Surelease ® (25% Solid) | 50.0 |

The coating used was a SURELEASE aqueous dispersion (Commercial Aqueous dispersion of EC from Colorcon Manufacturer Lot #1N509251) The dissolution results of uncrushed (FIG. 1) and crushed (FIG. 2) particles from the aqueous coating are shown in plots using diamonds indicating the measured data points.

Example 3

TABLE 5

Granules Formulation

| Component | % (w/w) |
|---|---|
| Oxycodone Hydrochloride | 46.1 |
| Hydroxypropyl methylcellulose 844 | 36.9 |
| Ethylcellulose | 17.0 |

TABLE 6

Coated Granules Formulation

| Component | % (w/w) |
|---|---|
| Oxycodone Granules | 50.0 |
| Ethylcellulose | 33.3 |
| Magnesium Stearate | 16.6 |

The same manufacturing method as used in Example 1 can be used except only 54% of EC is dry mixed with other ingredients instead of 71%.

Example 4

Coated Granules Lot 3531-18

TABLE 7

Granules Formulation

| Component | % (w/w) |
|---|---|
| Oxycodone Hydrochloride | 46.1 |
| Hydroxypropyl methylcellulose 844 | 36.9 |
| Ethylcellulose | 17.0 |

TABLE 8

Coated Granules Formulation

| Component | % (w/w) |
|---|---|
| Oxycodone Granules | 50.0 |
| Ethylcellulose | 32.3 |
| Lutrol F127 | 1.6 |
| Magnesium Stearate | 16.1 |

The same manufacturing method as in Example 1 may be used except only 54% of EC is mixed dry with other ingredients (instead of 71). Also the coating dispersion contained EC and additives, namely: magnesium stearate:Lutrol:Ethanol ratio of 10:5:0.5:84.5.

Example 5

Coated Granules lot 3070-70

TABLE 9

Granules Formulation

| Component | % (w/w) |
|---|---|
| Oxycodone Hydrochloride | 65.6 |
| Hydroxypropyl methylcellulose 844 | 22.5 |
| Ethylcellulose | 11.9 |

TABLE 10

Coated Granules Formulation

| Component | % (w/w) |
|---|---|
| Oxycodone Granules | 50.0 |
| Ethylcellulose | 33.3 |
| Magnesium Stearate | 16.7 |

Figure 3:
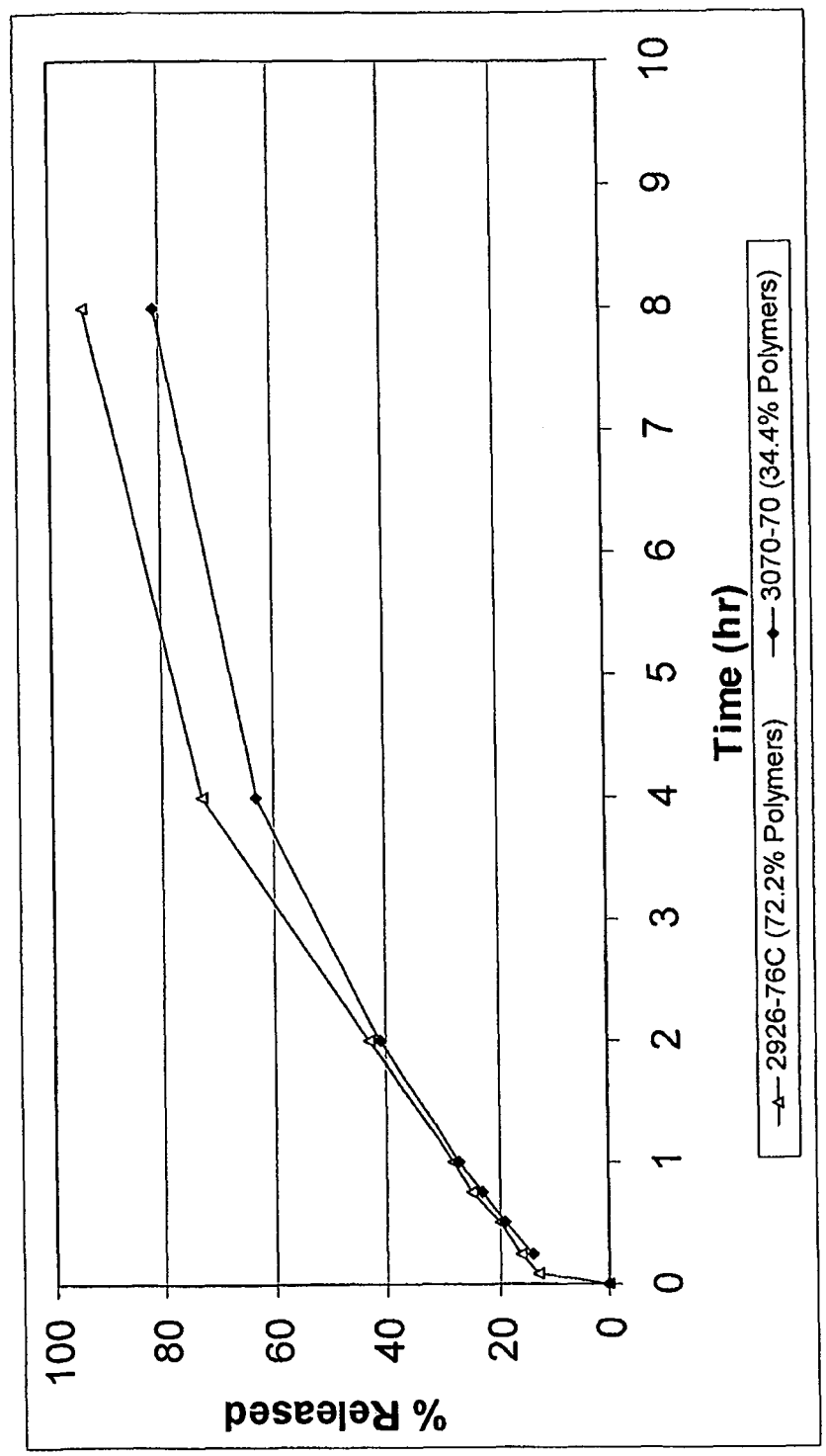
FIG. 3 illustrates the dissolution profiles of CR coated granulates of Examples 1 and 5 of the invention containing different levels of polymer in the granulate.
Figure 4:
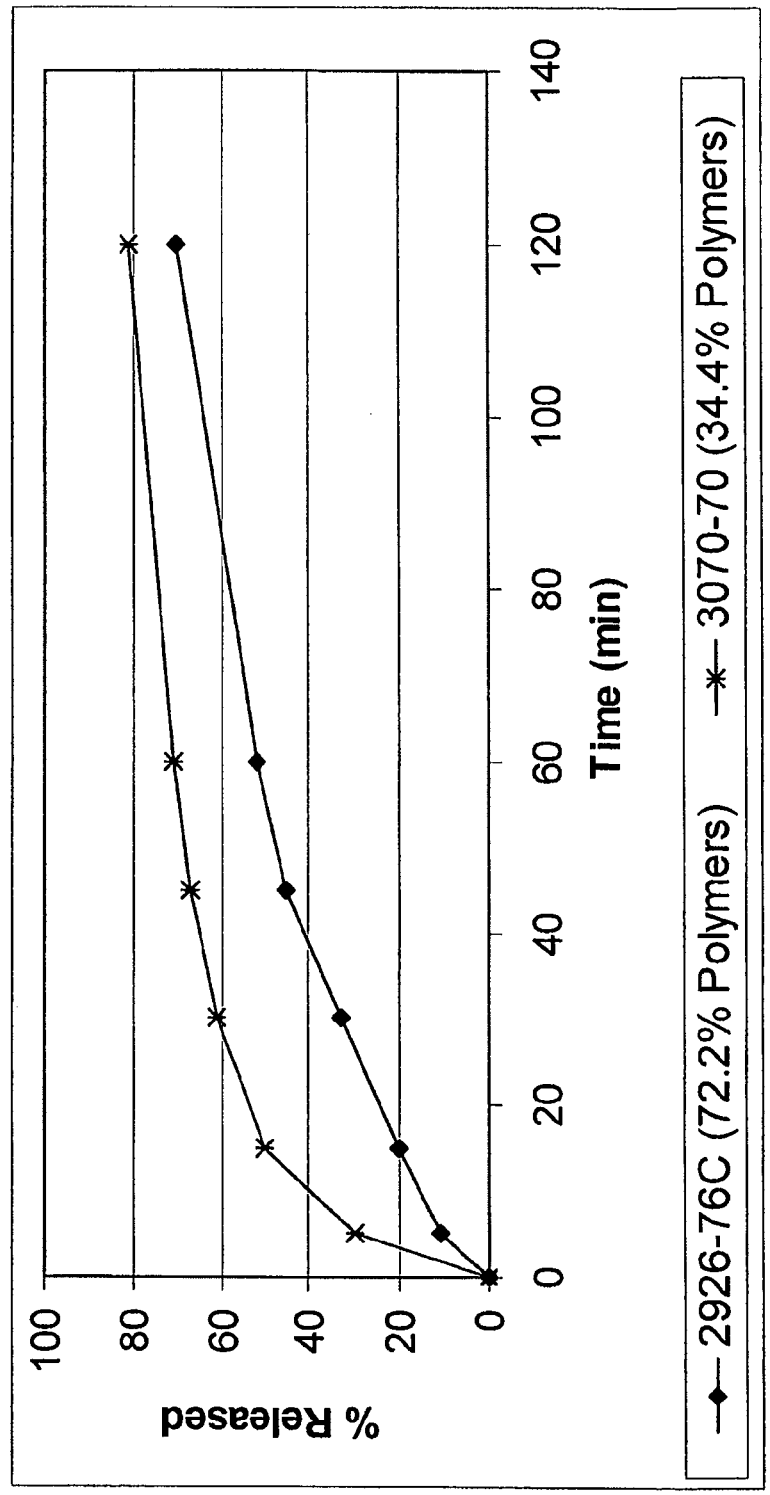
FIG. 4 illustrates the dissolution profiles of CR coated granulates of Examples 1 and 5 of the invention containing different levels of polymer in the granulate after crushing.

The same manufacturing method used as in Example 1 was employed here except only 47% of EC was dry mixed with other ingredients instead of 71% in the granulate core. FIGS. 3 and 4 provide dissolution profiles in 0.1N HCl for 50% coated granules with different levels of polymers in the granule portion of the coated granule. FIG. 3 illustrates a comparison between the dissolution profiles of the granules in Example 1, which contained approximately 72.2% polymer, coated in an ethanol based EC coating, with the coated particles produced in accordance with this example (Example 5) where the granulate (the uncoated granulate) contained approximately 34.4% polymer, coated with the same ethanolic based EC coating. FIG. 4 demonstrates the dissolution profiles of the same materials after they have been crushed as described in Example 1. In FIG. 3, the unshaded triangles represent the data plotted for the granulate of Example 1 and the shaded diamonds for the coated granulate of Example 5. In FIG. 4, the shaded diamonds provide the data for the coated granulate of Example 1 and the asterisks provide the data for the coated granulate of Example 5. It will be noted from FIG. 4 that the higher level of polymer content in the core (72.2% as opposed to 34.4%) provided relatively better crush resistance.

Example 6

The same manufacturing method as in Example 1 was employed here except that here the API particles were mixed with barrier beads as discussed herein.

TABLE 11

Granules Formulation

| Component | % (w/w) |
|---|---|
| Oxycodone Hydrochloride | 27.8 |
| Hydroxypropyl methylcellulose 844 | 46.3 |
| Ethylcellulose | 25.9 |

TABLE 12

Coated Granules Formulation

| Component | % (w/w) |
|---|---|
| Oxycodone Granules | 50.00 |
| Ethylcellulose | 33.33 |
| Magnesium Stearate | 16.67 |

Figure 5:
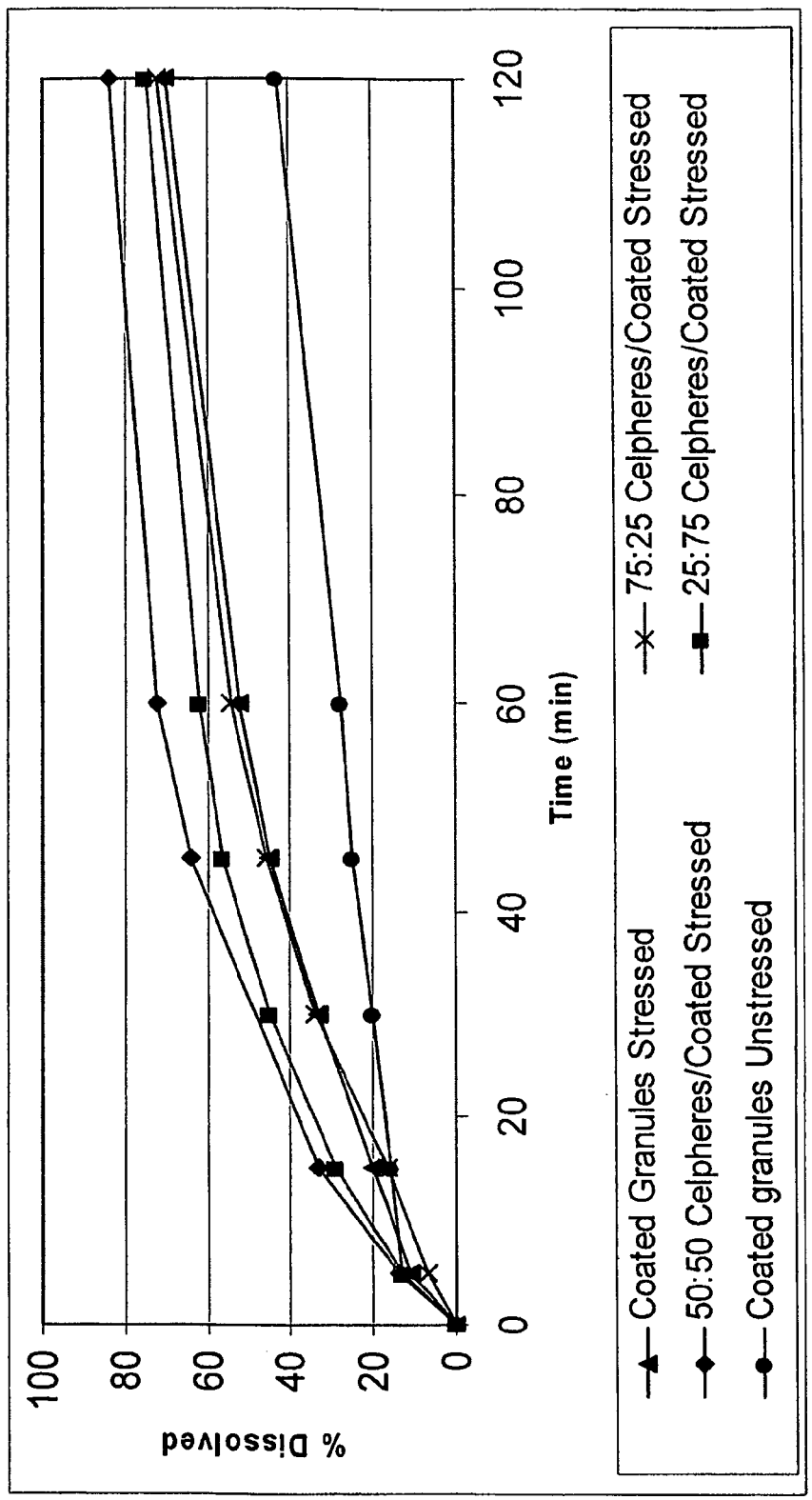
FIG. 5 illustrates comparative dissolution results for various coated granulates with and without barrier beads in variant proportions. The line formed by the triangles represents coated granules alone; the line formed by the diamonds represents a 50:50 mixture of celpheres and coated granulate produced in Example 6; the line formed by the "x"s represents a 75:25 mixture of celpheres to the coated granules; and the line formed by the squares represents a 25:75 mixture of celpheres to the coated granules of Example 6.

The coated granulates and barrier beads are then mixed in different proportions. Microcrystalline cellulose particles commercially available as Celphere CP-507 were used. Specifically, the coated particles were mixed with CP-507 at 25:75, 50:50 and 75:25. Published size information for the CP-507 was at least about 75% within range of 500-710 microns. The mixtures were subjected to mechanical stress by using 130 mm OD Porcelain mortar and 1-pound pestle. In summary, the particles are placed in a ceramic mortar (13 cm outer diameter) then by using the pestle and applying force vertically down word, the coated granules are crushed by 360° C. circular motion. Each full circle motion constitutes 1 stroke. Each sample is crushed by applying 12 strokes as described above. Oxycodone release from the stressed granules was measured in USP Dissolution apparatus 2 using 0.1 N HCl as release medium. The release profiles from non-stressed as well as stressed mixtures of oxycodone coated granules and Celpheres are presented in FIG. 5.

Note that at 75:25 barrier bead:API particle ratio, additional protection was obtained against stress. In other instances, the ratio needed to provide additional protection when compared to a formulation without barrier beads will differ. It is also important to note that this improvement was realized using protected particles which were themselves designed to be crush resistant. Indeed, granulates made with certain celluloses from an aqueous/alcoholic solution as a binder are believed to provide crush resistance when compared to an identical granulate made using water without alcohol as the binder. Similarly, a particle coated with a cellulose from an aqueous/alcoholic solution has been found to independently provide crush resistance when compared to an identically coated particle made using water without alcohol for the coating. Thus, the example demonstrates improvements resulting from the use of barrier beads can be obtained even when combined with other crush resistant technology. Indeed, improvement was realized here even where the average particle size of the barrier beads was considered to be less than that of the protected particles.

Example 7

Figure 6:
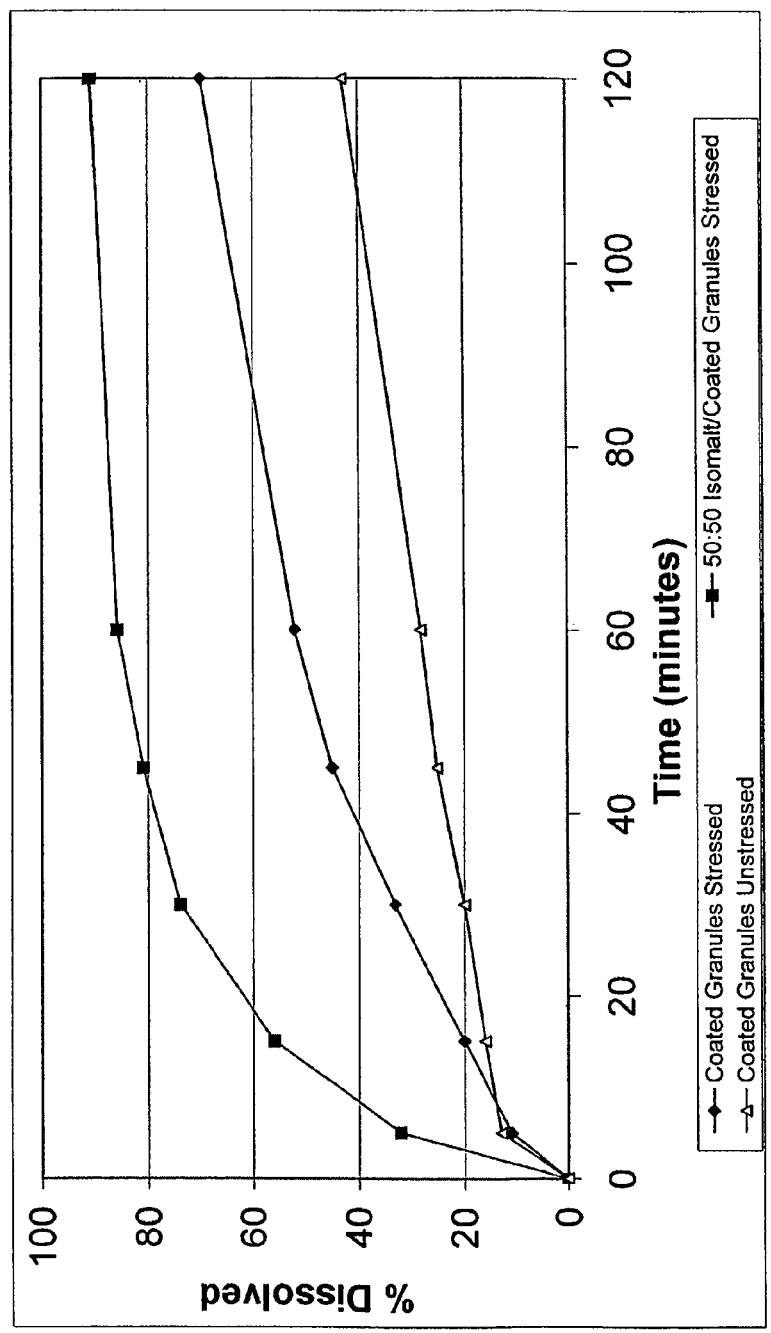
FIG. 6 illustrates a comparative test undertaken with the materials described in Example 7.

The coated oxycodone granules described in Example 6 above were also mixed in a 50:50 mixture with isomalt granules manufactured in Fluid bed granulator as barrier beads. The granules mixture was stressed in a mortar and pestle as described in example 6 above. The release profiles from non-stressed as well as stressed mixtures of oxycodone coated granules and isomalt granules are presented in FIG. 6.

Example 8

Coated Granules Lot 4002-79 (Gelucire 33/01 in Core Only not Cured)

Using a process similar to that described above in Examples 17 and 45, but with using 82% of EC for dry mixing together with 20% Gelucire 33/01 with other ingredients, the following formulation was prepared, which differs from Example 17 in the amounts of each component used. Before granulation, Gelucire 33/01 was first broken into small pieces (about 1 cm in diameter) using a hand-held extruder. Gelucire 33/01 pieces were then mixed by hand with HPMC and EC and hand screened through a 16-mesh screen. Hydromorphone HCl was then screened through the same screen and the mixture was then granulated. The wet granules were not partially dried prior to milling.

TABLE 87

Granules Formulations

| Ingredient | Amount (% w/w) |
|---|---|
| Hydromorphone HCl | 46.6 |
| Hydroxypropyl methylcellulose (HPMC) | 16.4 |
| Ethylcellulose | 17.0 |
| Gelucire 33/01 | 20.0 |
| Total | 100.0 |

TABLE 88

Coated Granules Formulation

| Ingredient | Amount (% w/w) |
|---|---|
| Hydromorphone granules | 50.0 |
| Ethylcellulose | 33.3 |
| Magnesium Stearate | 16.7 |
| Total | 100.00 |

Example 9

Coated Granules Lot 3375-51

Granules can be manufactured using a high shear granulator wherein oxycodone hydrochloride, hydroxymethylcellulose HPMC 844, and from about 47% to about 54% of the total amount of ethylcellulose to be used are dry mixed for a period of 2 minutes. Then, a 10% hydro-ethanolic (30:70) solution of ethylcellulose can be slowly added while maintaining the granulator impeller and chopper speeds at preselected values sufficient to provide shear for granule formation and growth. The solution can be added until the desired percentage ethylcellulose is obtained. The granules can then be dried in a fluid bed to a level rendering them suitable for milling. The granules can then be milled in a mill and dried.

Using a process similar to that described hereinabove and using 54% of the total amount of ethylcellulose, the following uncoated granulate composition was prepared:

TABLE 16

Uncoated Oxycodone Granule

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.0 |

The prepared granules can then be coated in a bottom spray fluid bed using a 15% alcoholic suspension of ethylcellulose and magnesium stearate (2:1). After coating, about 40% of the coated granules based on weight can be composed of the coating materials. Using this process, the following coated granule formulation was prepared:

TABLE 17

Coated Oxycodone Granule

| Ingredient | Amount (% w/w) |
|---|---|
| Oxycodone granules (oxycodone HCl, HPMC, ethylcellulose of Table 16) | 60.00 |
| Ethylcellulose | 26.67 |
| Magnesium stearate | 13.33 |
| Total | 100.00 |

Example 10

Tablet Lot 3375-59

Coated granules prepared as described herein above can be formed into solid dosage form, e.g., tablet. The coated granules can be mixed with EMCOMPRESS (dibasic calcium phosphate dihydrate), lactose (FAST-FLO, spray-dried), COMPRITOL ATO 888 (glyceryl behenate) in a V-blender for a period of about 30 minutes. The blended mixture can then be compressed in a rotary tablet press to form tablets. Tablet weight can vary from about 110 mg for a 10 mg oxycodone HCl active ingredient to about 880 mg for an 80 mg oxycodone HCl tablet. Using this process, the following tablet was prepared:

TABLE 18

Oxycodone HCl (10 mg) Tablet Formulation

| Component | Amount (% w/w) | Amount (mg) |
|---|---|---|
| Oxycodone coated granules (Table 17) | 38.82 | 42.70 |
| EMCOMPRESS | 33.18 | 36.50 |
| Lactose | 23.00 | 25.30 |
| COMPRITOL (glyceryl behenate) | 5.00 | 5.50 |
| Total | 100.00 | 110.00 mg |

The above calculations account for the fact that the actual potency of the coated granules made were less than the theoretical amount. Thus, 110.00 mg of the prepared tablet contained 10 mg oxycodone HCl.

Various tablet shapes and sizes can be employed with the invention. Furthermore, the same process above can be used except the second particle fat/wax with a low melting point is melted and poured into a capsule shell and combined, or pre-combined, and the suspension can then be poured into a capsule shell.

Example 11

10 mg oxycodone HCl tablets prepared according to the invention were dissolved in two dissolution medium: acid/water medium (normal) and water/alcohol (alcohol) medium in order to measure the percent active ingredient released over time and compare the results.

Using compressed tablets prepared using the 10 mg oxycodone-containing composition prepared according to Example 10 with the formulation of Table 18, the normal dissolution of the active ingredient in dissolution medium was measured. Starting with 500 ml 0.1 N HCl (in water) as a release (dissolution) medium at a temperature of 37° C. in a USP Dissolution apparatus (2 paddles at a rate of rpm 50), granules (equivalent to 10 mg oxycodone HCl) were added to the dissolution medium. Samples were withdrawn at intervals 5 min, 15 min, 30 min, 45 min, 60 min, 120 min. Each sample was tested for solubilized oxycodone content using HPLC method, and the values described in percentage terms and plotted against time to establish release profiles. The data appears in the following table:

TABLE 19

Percent (%) Oxycodone Released per Time in HCl/Water Dissolution Medium

| Time (min) | Percent (%) Release Oxycodone HCl |
|---|---|
| 0 | 0 |
| 5 | 2 |
| 15 | 10 |
| 30 | 22 |
| 45 | 33 |
| 60 | 44 |
| 120 | 82 |

Figure 7:
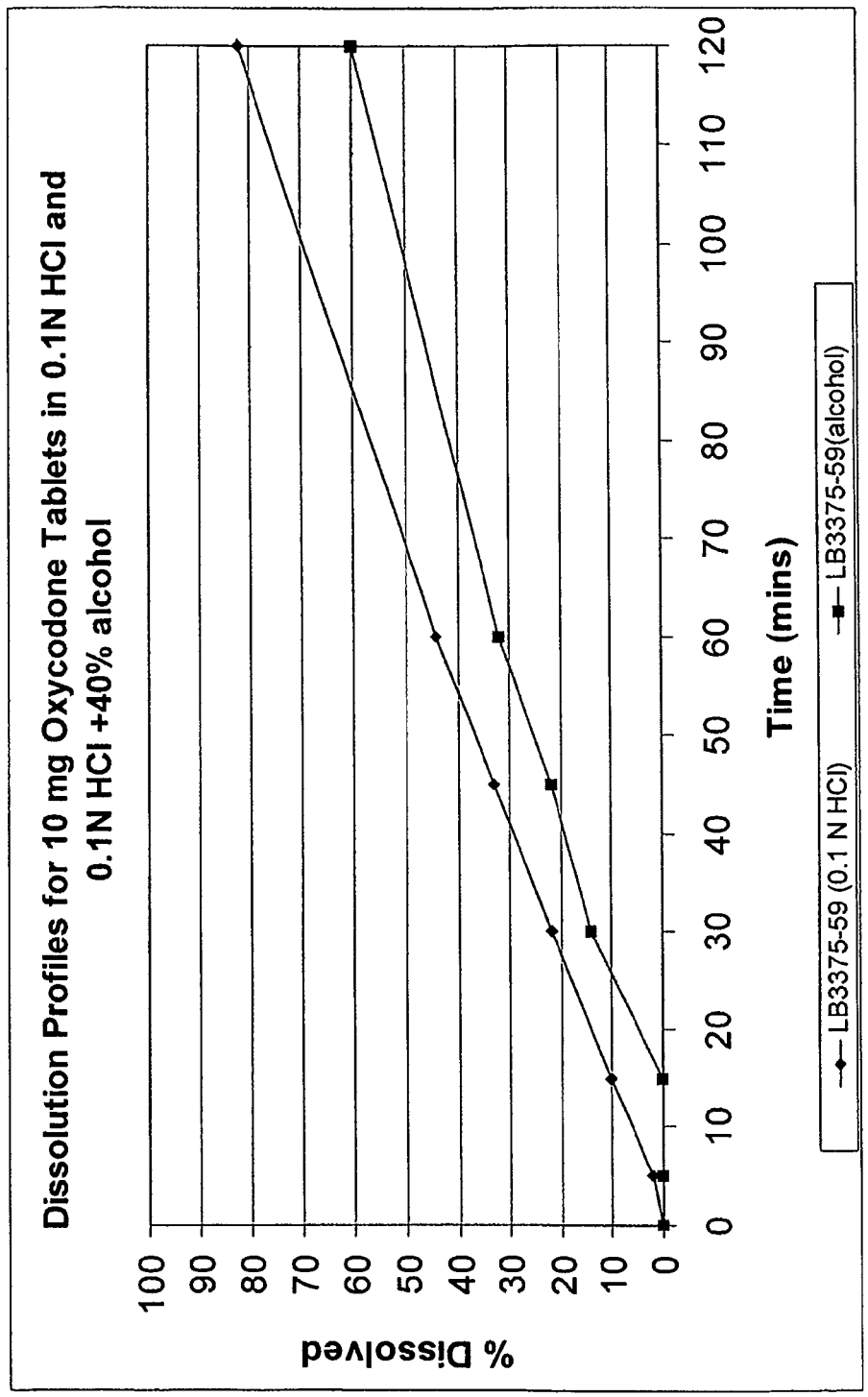
FIG. 7 is a chart showing the comparative dissolution profiles as described in Example 11 for oxycodone HCl (10 mg) tablets prepared according to one embodiment of the invention.

The normal dissolution data as plotted appears in FIG. 7.

Normal dissolution was compared to dissolution conditions representative of solvent (alcohol)-accelerated dose dumping abuse and tampering conduct. The procedure above was repeated except the dissolution medium contained water:ethanol in 60:40 volume ratio simulating a combination of the tablet with alcohol. Samples were taken at 5, 15, 30, 45, 60 and 120 minute intervals, and measured again for oxycodone content. The results were plotted against time and appear in the following table:

TABLE 20

Percent (%) Oxycodone Released per Time in Alcohol and Water Dissolution Medium

| Time (min) | Percent (%) Release Oxycodone HCl |
|---|---|
| 0 | 0 |
| 5 | 0 |
| 15 | 0 |
| 30 | 14 |
| 45 | 22 |
| 60 | 32 |
| 120 | 60 |

The data as plotted appears in the chart of FIG. 7 (Dissolution Profiles).

As can be seen from the figure, the ability to accelerate the release of active ingredients (e.g., oxycodone HCl) from tablet dosage forms prepared according to the invention, using alcohol as a solvent, is limited. The measured amounts of oxycodone active release in alcohol-containing dissolution medium is comparable to that amount measured in the acidic water-containing (normal) dissolution medium.

Example 12

Tablet Lot 3070-98

Using a process similar to that described above in Example 9 and using 54% of the total amount of ethylcellulose, the following uncoated granulate composition was prepared:

TABLE 21

Uncoated Oxycodone Granule

| Ingredient | Amount (% w/w) |
|---|---|
| Oxycodone HCl | 65.61 |
| Hydroxypropyl methylcellulose (HPMC) | 22.49 |
| Ethylcellulose | 11.90 |
| Total | 100.00 |

Using a process similar to that described above in Example 9, the following coated granule composition was prepared:

TABLE 22

Coated Oxycodone Granule

| Ingredient | Amount (% w/w) |
|---|---|
| Oxycodone granules (oxycodone HCl, HPMC, ethylcellulose of Table 21) | 50.00 |
| Ethylcellulose | 33.33 |
| Magnesium stearate | 16.67 |
| Total | 100.00 |

Using a process similar to that described above in Example 10, the following formulation was prepared:

TABLE 23

Oxycodone HCl (80 mg) Tablet Formulation

| Ingredient | Amount (% w/w) | Amount (mg) |
|---|---|---|
| Oxycodone coated granules (of Table 22) | 39.02 | 243.90 |
| EMCOMPRESS | 30.59 | 191.20 |
| Lactose | 20.38 | 127.40 |
| COMPRITOL (glyceryl behenate) | 10.00 | 62.50 |
| Total | 100.00 | 625.00 mg |

Example 13

80 mg oxycodone HCl tablets prepared according to the invention and as formulated in Table 23, were dissolved in two dissolution medium: acid/water medium (normal) and water/alcohol (alcohol) medium in order to measure the percent active ingredient released over time and compare the results.

Using compressed tablets prepared using the 80 mg oxycodone-containing composition prepared according to Example 12 with the formulation of Table 23, the normal dissolution of the active ingredient in solution medium was measured. Starting with 500 ml 0.1 N HCl (in water) as a release (dissolution) medium at a temperature of 37° C. in a USP Dissolution apparatus (2 paddles at a rate of rpm 50), granules (equivalent to 80 mg oxycodone HCl) were added to the dissolution medium. Samples were withdrawn at intervals 5 min, 15 min, 30 min, 45 min, 60 min, 120 min. Each sample was tested for solubilized oxycodone content using HPLC method, and the values described in percentage terms and plotted against time to establish release profiles. The data appears in the following table:

TABLE 24

Percent (%) Oxycodone Released per Time in Acid/Water Dissolution Medium

| Time (min) | Percent (%) Release oxycodone HCl |
|---|---|
| 0 | 0 |
| 5 | 1 |
| 15 | 2 |
| 30 | 4 |
| 45 | 6 |
| 60 | 8 |
| 120 | 18 |

Figure 8:
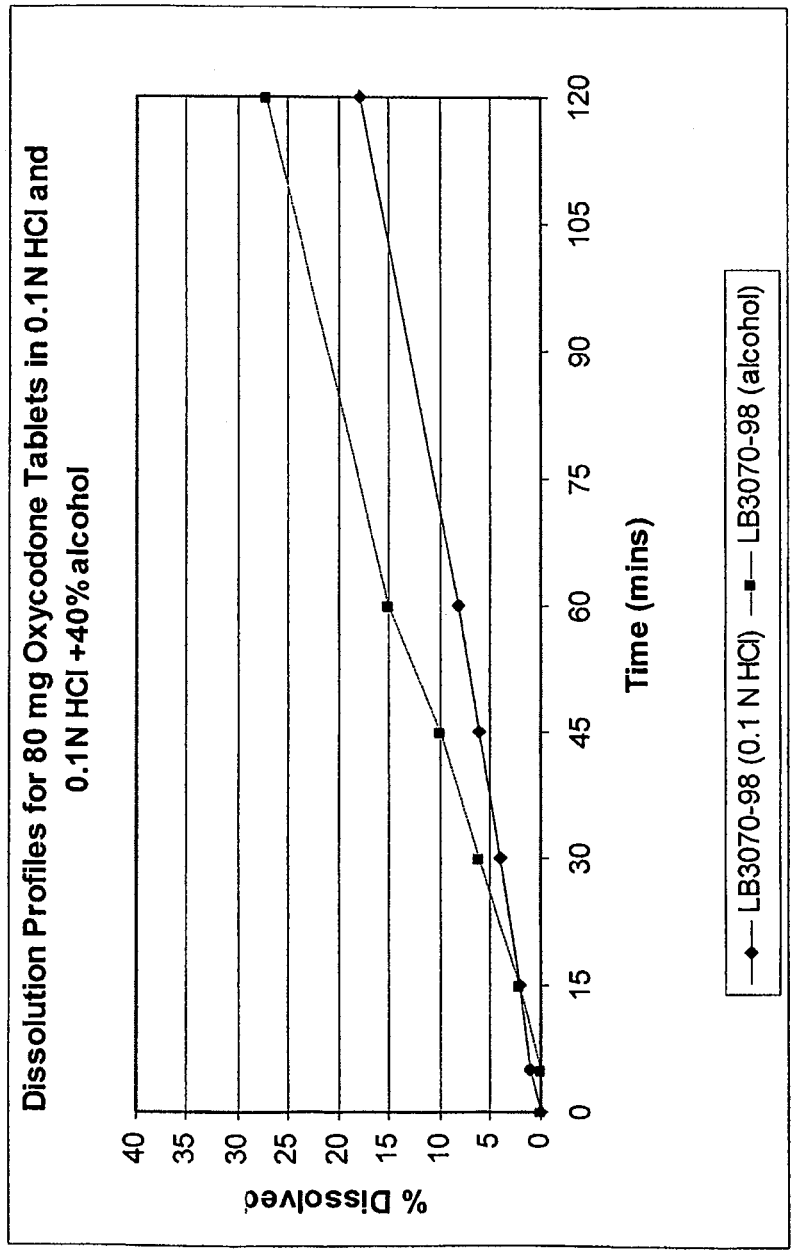
FIG. 8 is a chart showing the comparative dissolution profiles as described in Example 13 for oxycodone HCl (80 mg) tablets prepared according to one embodiment of the invention.

The normal dissolution data as plotted appears in FIG. 8.

Normal dissolution was compared to dissolution conditions representative of solvent (alcohol)-accelerated dose dumping abuse and tampering conduct. The procedure above was repeated except the dissolution medium contained water:ethanol in 60:40 volume ratio simulating a combination of the tablet with alcohol. Samples were taken at 5, 15, 30, 45, 60, and 120 minute intervals, and measured again for oxycodone content. The results were plotted against time and appear in the following table:

TABLE 25

Percent (%) Oxycodone Released per Time in Water/Alcohol Dissolution Medium

| Time (min) | Percent (%) Release Oxycodone HCl |
|---|---|
| 0 | 0 |
| 5 | 0 |
| 15 | 2 |
| 30 | 6 |
| 45 | 10 |
| 60 | 15 |
| 120 | 27 |

The alcohol dissolution data as plotted appears in FIG. 8. As can be seen from the chart of FIG. 8, the ability to accelerate the release of active ingredients (e.g., oxycodone HCl) from tablet dosage forms prepared according to the invention, using alcohol as a solvent, is limited. The measured amounts of oxycodone active release in alcohol-containing dissolution medium is at least comparable to that amount measured in the acidic water-containing (normal) dissolution medium.

Example 14

Coated Granules Lot 770300

The present invention can be illustrated by producing a composition including CR coated particles with wet granules as API particles.

Using a process similar to that described above in Example 1, except 53% of EC is dry mixed with other ingredients instead of 71%, the following formulation was prepared, which differs from Example 1 in the amounts of each component used

TABLE 26

Granules Formulations

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.00 |

TABLE 27

Coated Granules Formulation

| Ingredient | Amount (% w/w) |
|---|---|
| Oxycodone granules (oxycodone HCl, HPMC, ethylcellulose) | 60.00 |
| Ethylcellulose | 26.67 |
| Magnesium stearate | 13.33 |
| Total | 100.00 |

Using a process similar to that described above in Example 10, the following formulation was prepared using different amounts and components than in Example 10:

TABLE 28

Oxycodone HCl (80 mg) Tablet Formulation

| Component | Amount (% w/w) | Amount (mg) |
|---|---|---|
| Oxycodone coated granules | 33.98 | 288.8 |
| Lactose Monohydrate (fast Flo) | 56.02 | 476.2 |
| COMPRITOL (glyceryl behenate) | 10.00 | 85.0 |
| Total | 100.00 | 850.0 mg |

While COMPRITOL is always kept at 10% of the total weight of the dosage form (tablet), any change in the actual assay amount, from theoretical values, is accounted for by changing the amount of lactose and coated granules to maintain the amount of Oxycodone HCl at 80 mg per tablet. The average tablet weight is 850 mg, and has an average hardness of between 140 and 155 N. The tablet dimensions are 0.3125"×0.5625."

Using a process similar to that of Example 11, the following data was obtained using the above formulation:

TABLE 29

Percent (%) Oxycodone Released per Time in HCl/Water Dissolution Medium

| Time (min) | Percent (%) Release Oxycodone HCl |
|---|---|
| 0 | 0 |
| 30 | 11 |
| 60 | 28 |
| 120 | 62 |
| 240 | 95 |
| 360 | 97 |
| 480 | 98 |
| 600 | 98 |
| 720 | 99 |

TABLE 30

Percent (%) Oxycodone Released per Time in
Alcohol and Water Dissolution Medium

| Time (min) | Percent (%) Release Oxycodone HCl |
|---|---|
| 0 | 0 |
| 5 | 0 |
| 15 | 3 |
| 30 | 7 |
| 45 | 11 |
| 60 | 14 |
| 120 | 31 |

TABLE 30

Percent (%) Oxycodone Released per Time in
HCl/Water Dissolution Medium after crushing

| Time (min) | Percent (%) Release Oxycodone HCl |
|---|---|
| 0 | 0 |
| 5 | 8 |
| 15 | 34 |
| 30 | 69 |
| 45 | 86 |
| 60 | 94 |
| 120 | 98 |

Figure 9:
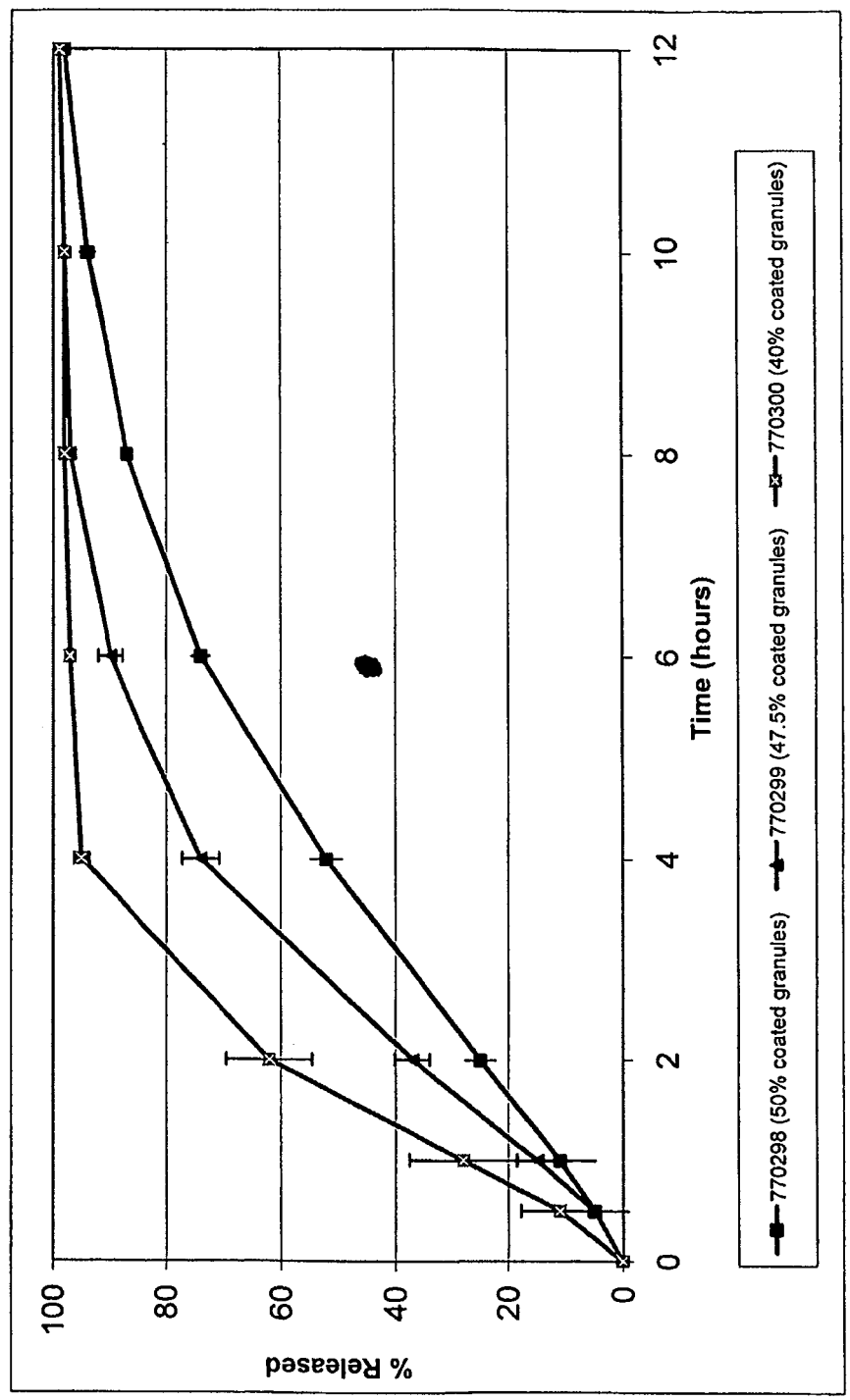
FIG. 9 is a chart showing the comparative dissolution profiles of CR coated granulates of Examples 14 through 16 of the invention containing different percentages of coated granulate.

The data of Table 29 is illustrated in FIG. 9 as the upper curve with shaded squares and "X"s.

Example 15

Coated Granules Lot 770299

Using a process similar to that described above in Example 14, again dry mixing only 53% of EC with other ingredients, the following formulation was prepared, which differs from Example 14 in the amounts of each component used:

TABLE 32

Granules Formulations

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.00 |

TABLE 33

Coated Granules Formulation

| Ingredient | Amount (% w/w) |
|---|---|
| Oxycodone granules (oxycodone HCl, HPMC, ethylcellulose) | 52.5 |
| Ethylcellulose | 31.7 |
| Magnesium stearate | 15.8 |
| Total | 100.00 |

Using a process similar to that described in Example 14, the following formulation was prepared using different amounts than in Example 14:

TABLE 34

Oxycodone HCl (80 mg) Tablet Formulation

| Component | Amount (% w/w) | Amount (mg) |
|---|---|---|
| Oxycodone coated granules | 38.89 | 330.6 |
| Lactose Monohydrate (fast Flo) | 51.11 | 434.4 |
| COMPRITOL (glyceryl behenate) | 10.00 | 85.0 |
| Total | 100.00 | 850.0 mg |

While COMPRITOL is always kept at 10% of the total weight of the dosage form (tablet), any change in the actual assay amount, from theoretical values, is accounted for by changing the amount of lactose and coated granules to maintain the amount of Oxycodone HCl at 80 mg per tablet. The average tablet weight is 850 mg, and has an average hardness of between 140 and 155 N. The tablet dimensions are 0.3125"×0.5625".

Using a process similar to that of Example 14, the following data was obtained using the above formulation:

TABLE 35

Percent (%) Oxycodone Released per Time in
HCl/Water Dissolution Medium

| Time (min) | Percent (%) Release Oxycodone HCl |
|---|---|
| 0 | 0 |
| 30 | 5 |
| 60 | 15 |
| 120 | 37 |
| 240 | 74 |
| 360 | 90 |
| 480 | 97 |
| 600 | 98 |
| 720 | 99 |

TABLE 36

Percent (%) Oxycodone Released per Time in
Alcohol and Water Dissolution Medium

| Time (min) | Percent (%) Release Oxycodone HCl |
|---|---|
| 0 | 0 |
| 5 | 0 |
| 15 | 2 |
| 30 | 6 |
| 45 | 9 |
| 60 | 12 |
| 120 | 25 |

TABLE 37

Percent (%) Oxycodone Released per Time in
HCl/Water Dissolution Medium after crushing

| Time (min) | Percent (%) Release Oxycodone HCl |
|---|---|
| 0 | 0 |
| 5 | 4 |
| 15 | 15 |
| 30 | 42 |
| 45 | 63 |

TABLE 37-continued

Percent (%) Oxycodone Released per Time in HCl/Water Dissolution Medium after crushing

| Time (min) | Percent (%) Release Oxycodone HCl |
|---|---|
| 60 | 78 |
| 120 | 95 |

The data of Table 35 is illustrated in FIG. 9 as the shaded triangles.

Example 16

Coated Granules Lot 770298

Using a process similar to that described above in Example 15, again using only 53% of EC for dry mixing with other ingredients, the following formulation was prepared, which differs from Example 15 in the amounts of each component used:

TABLE 38

Granules Formulations

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.00 |

TABLE 39

Coated Granules Formulation

| Ingredient | Amount (% w/w) |
|---|---|
| Oxycodone granules (oxycodone HCl, HPMC, ethylcellulose) | 50.0 |
| Ethylcellulose | 33.3 |
| Magnesium stearate | 16.7 |
| Total | 100.00 |

Using a process similar to that described above in Example 15, the following formulation was prepared using different amounts than in Example 15:

TABLE 40

Oxycodone HCl (80 mg) Tablet Formulation

| Component | Amount (% w/w) | Amount (mg) |
|---|---|---|
| Oxycodone coated granules | 40.74 | 346.3 |
| Lactose Monohydrate (fast Flo) | 49.26 | 418.7 |
| COMPRITOL (glyceryl behenate) | 10.00 | 85.0 |
| Total | 100.00 | 850.0 mg |

While COMPRITOL is always kept at 10% of the tablet weight, any change in the actual assay amount, from theoretical values, is accounted for by changing the amount of lactose and coated granules to maintain the amount of Oxycodone HCl at 80 mg. The average tablet weight is 850 mg, and has an average hardness of between 139 and 155 N. The tablet dimensions are 0.3125"×0.5625".

Using a process similar to that of Example 15, the following data was obtained using the above formulation:

TABLE 41

Percent (%) Oxycodone Released per Time in HCl/Water Dissolution Medium

| Time (min) | Percent (%) Release Oxycodone HCl |
|---|---|
| 0 | 0 |
| 30 | 5 |
| 60 | 11 |
| 120 | 25 |
| 240 | 52 |
| 360 | 74 |
| 480 | 87 |
| 600 | 94 |
| 720 | 98 |

TABLE 42

Percent (%) Oxycodone Released per Time in Alcohol and Water Dissolution Medium

| Time (min) | Percent (%) Release Oxycodone HCl |
|---|---|
| 0 | 0 |
| 5 | 1 |
| 15 | 2 |
| 30 | 6 |
| 45 | 8 |
| 60 | 11 |
| 120 | 23 |

TABLE 43

Percent (%) Oxycodone Released per Time in HCl/Water Dissolution Medium after crushing

| Time (min) | Percent (%) Release Oxycodone HCl |
|---|---|
| 0 | 0 |
| 5 | 5 |
| 15 | 13 |
| 30 | 29 |
| 45 | 44 |
| 60 | 57 |
| 120 | 85 |

The data of Table 41 is illustrated in FIG. 9 as the lower curve with shaded squares.

Example 17

Coated Granules Lots #3766-06B and 3766-80

Using a process similar to that described above in Example 3, again using only 53% of EC for dry mixing with other ingredients instead of 54%, the following formulation was prepared, which differs from Example 3 in the amounts of each component used and the drug used:

TABLE 44

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 45

| Coated Granules Formulation | |
|---|---|
| Ingredient | Amount (% w/w) |
| Hydromorphone granules | 50.0 |
| Ethylcellulose | 33.3 |
| Magnesium stearate | 16.7 |
| Total | 100.00 |

In this example, Hydromorphone HCl was substituted for Oxycodone HCl. However, the same process steps may be used for various types of API's.

Example 18

Coated Granules Lot #3766-06C

Using a process similar to that described above in Example 17, again using only 53% of EC for dry mixing with other ingredients, the following formulation was prepared, which differs from Example 17 in the amounts of each component used:

TABLE 46

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 47

| Coated Granules Formulation | |
|---|---|
| Ingredient | Amount (% w/w) |
| Hydromorphone granules | 40.0 |
| Ethylcellulose | 40.0 |
| Magnesium stearate | 20.0 |
| Total | 100.00 |

As in Example 17, Hydromorphone HCl replaced Oxycodone HCl as the API.

Example 19

Coated Granules Lot #3766-06A

Using a process similar to that described above in Example 18, again using only 53% of EC for dry mixing with other ingredients, the following formulation was prepared, which differs from Example 18 in the amounts of each component used:

TABLE 48

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 49

| Coated Granules Formulation | |
|---|---|
| Ingredient | Amount (% w/w) |
| Hydromorphone granules | 60.0 |
| Ethylcellulose | 26.7 |
| Magnesium stearate | 13.3 |
| Total | 100.00 |

As in Example 18, Hydromorphone HCl replaced Oxycodone HCl as the API.

Figure 10:
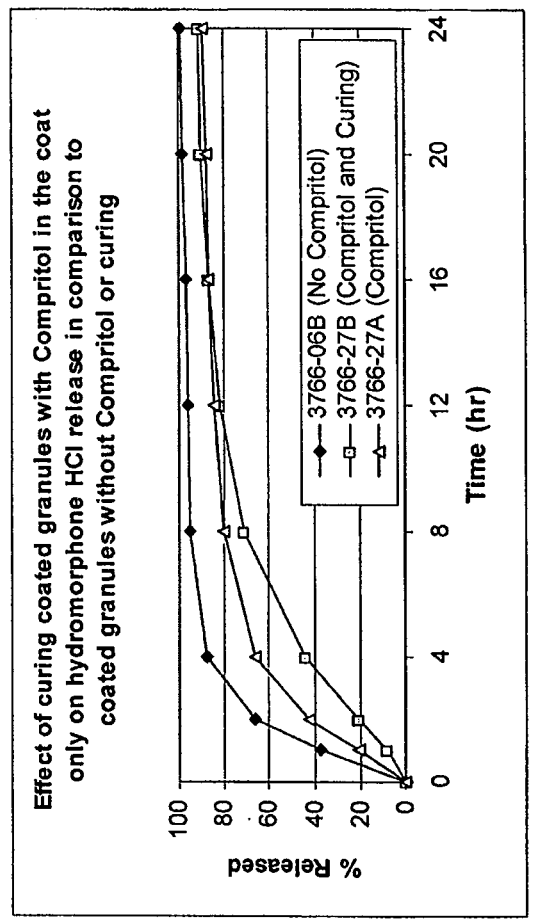
FIG. 10 illustrates the effect of curing coated granules with Compritol in the coat only on hydromorphone HCl release in comparison to coated granules without Compritol or curing.

[Start with Example 20 and FIG. 10 and Table 50]

Example 20

Coated Granules Lot#3766-27A (Compritol in the Coat Only and not Cured)

Using a process similar to that described above in Example 17, again using only 53% of EC for dry mixing with other ingredients, the following formulation was prepared, which differs from Example 17 in the amounts of each component used.

TABLE 50

| Granules Formulations | |
|---|---|
| Ingredient | Amount (% w/w) |
| Hydromorphone HCl | 46.6 |
| Hydroxypropyl methylcellulose (HPMC) | 36.4 |
| Ethylcellulose | 17.0 |
| Total | 100.00 |

TABLE 51

| Coated Granules Formulation | |
|---|---|
| Ingredient | Amount (% w/w) |
| Hydromorphone granules | 50.0 |
| Ethylcellulose | 33.3 |
| Glycerol Behenate (Compritol 888 Ato) | 16.7 |
| Total | 100.00 |

Example 21

Coated Granules Lot#3766-27B (Compritol in the Coat Only and Cured)

Using a process similar to that described above in Example 17, again using only 53% of EC for dry mixing with other ingredients, the following formulation was prepared, which differs from Example 17 in the amounts of each component used.

TABLE 52

Granules Formulations

| Ingredient | Amount (% w/w) |
|---|---|
| Hydromorphone HCl | 46.6 |
| Hydroxypropyl methylcellulose (HPMC) | 36.4 |
| Ethylcellulose | 17.0 |
| Total | 100.00 |

TABLE 53

Coated Granules Formulation

| Ingredient | Amount (% w/w) |
|---|---|
| Hydromorphone granules | 50.0 |
| Ethylcellulose | 33.3 |
| Glycerol Behenate (Compritol 888 Ato) | 16.7 |
| Total | 100.00 |

After the right amount of coating has been sprayed into the granules, the coated granules were further cured by suspending them in the fluid bed while increasing the inlet air temperature. Curing was considered complete when the bed temperature was maintained above 60° C. for 40 minutes.

Example 22

Coated Granules Lot#3766-33 (Compritol in the Core Only and not Cured)

Using a process similar to that described above in Example 17, but with using 72% of EC for dry mixing together with 20% glycerol behenate with other ingredients, the following formulation was prepared, which differs from Example 17 in the amounts of each component used.

TABLE 54

Granules Formulations

| Ingredient | Amount (% w/w) |
|---|---|
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 55

Coated Granules Formulation

| Ingredient | Amount (% w/w) |
|---|---|
| Hydromorphone granules | 50.0 |
| Ethylcellulose | 33.3 |
| Magnesium stearate | 16.7 |
| Total | 100.00 |

Example 23

Coated Granules Lot#3766-38 (Compritol in the Core Only and Cured)

Using a process similar to that described above in Example 17, but with using 72% of EC for dry mixing together with 20% glycerol behenate with other ingredients, the following formulation was prepared, which differs from Example 17 in the amounts of each component used. The uncoated granules were further cured by suspended them in the fluid bed while increasing the inlet air temperature. Curing was considered complete when the bed temperature was maintained above 60° C. for 40 minutes and above 70° C. for 20 minutes.

TABLE 56

Granules Formulations

| Ingredient | Amount (% w/w) |
|---|---|
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 57

Coated Granules Formulation

| Ingredient | Amount (% w/w) |
|---|---|
| Hydromorphone granules | 50.0 |
| Ethylcellulose | 33.3 |
| Magnesium stearate | 16.7 |
| Total | 100.00 |

Example 24

Coated Granules Lot#4002-21 (Compritol in the Core and Cured and in the Coat and Cured)

Using a process similar to that described above in Example 17, but with using 72% of EC for dry mixing together with 20% glycerol behenate with other ingredients, the following formulation was prepared, which differs from Example 17 in the amounts of each component used. The wet granules were not partially dried prior to milling. The uncoated granules were further cured by suspended them in the fluid bed while increasing the inlet air temperature. Curing was considered complete when the bed temperature was maintained above 60° C. for 30 minutes.

TABLE 58

Granules Formulations

| Ingredient | Amount (% w/w) |
| --- | --- |
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 59

Coated Granules Formulation

| Ingredient | Amount (% w/w) |
| --- | --- |
| Hydromorphone granules | 50.0 |
| Ethylcellulose | 33.3 |
| Glycerol Behenate (Compritol 888 Ato) | 16.7 |
| Total | 100.00 |

After the right amount of coating has been sprayed into the granules, the coated granules were further cured by suspending them in the fluid bed while increasing the inlet air temperature. Curing was considered complete when the bed temperature was maintained above 60° C. for 30 minutes.

Example 25

Coated Granules Lot#4002-31B (Compritol in the Core and Cured and in the Coat and Cured, 50% Coat)

Using a process similar to that described above in Example 17, but with using 61% of EC for dry mixing together with 10% glycerol behenate with other ingredients, the following formulation was prepared, which differs from Example 17 in the amounts of each component used. The wet granules were not partially dried prior to milling. The uncoated granules were further cured by suspended them in the fluid bed while increasing the inlet air temperature. Curing was considered complete when the bed temperature was maintained above 65° C. for 30 minutes.

TABLE 60

Granules Formulations

| Ingredient | Amount (% w/w) |
| --- | --- |
| Hydromorphone HCl | 46.7 |
| Hydroxypropyl methylcellulose (HPMC) | 26.5 |
| Ethylcellulose | 16.8 |
| Glycerol behenate | 10.0 |
| Total | 100.0 |

TABLE 61

Coated Granules Formulation

| Ingredient | Amount (% w/w) |
| --- | --- |
| Hydromorphone granules | 50.0 |
| Ethylcellulose | 33.3 |
| Glycerol Behenate (Compritol 888 Ato) | 16.7 |
| Total | 100.00 |

After the right amount of coating has been sprayed into the granules, the coated granules were further cured by suspending them in the fluid bed while increasing the inlet air temperature. Curing was considered complete when the bed temperature was maintained above 65° C. for 30 minutes.

Example 26

Coated Granules Lot#4002-31A (Compritol in the Core and Cured and in the Coat and Cured, 40% Coat)

Using a process similar to that described above in Example 17, but with using 61% of EC for dry mixing together with 10% glycerol behenate with other ingredients, the following formulation was prepared, which differs from Example 17 in the amounts of each component used. The wet granules were not partially dried prior to milling. The uncoated granules were further cured by suspended them in the fluid bed while increasing the inlet air temperature. Curing was considered complete when the bed temperature was maintained above 65° C. for 30 minutes.

TABLE 62

Granules Formulations

| Ingredient | Amount (% w/w) |
| --- | --- |
| Hydromorphone HCl | 46.7 |
| Hydroxypropyl methylcellulose (HPMC) | 26.5 |
| Ethylcellulose | 16.8 |
| Glycerol behenate | 10.0 |
| Total | 100.0 |

TABLE 63

Coated Granules Formulation

| Ingredient | Amount (% w/w) |
| --- | --- |
| Hydromorphone granules | 60.0 |
| Ethylcellulose | 26.7 |
| Glycerol Behenate (Compritol 888 Ato) | 13.3 |
| Total | 100.00 |

After the right amount of coating has been sprayed into the granules in the fluid bed, the coated granules were further cured by placing them in an oven set at temperature of 70° C. for 30 minutes.

Example 27

Coated Granules Lot#4002-40A (Compritol in the Core and not Cured and in the Coat and not Cured, 50% Coat)

Using a process similar to that described above in Example 17, but with using 72% of EC for dry mixing together with 20% glycerol behenate with other ingredients, the following formulation was prepared, which differs from Example 17 in the amounts of each component used. The wet granules were not partially dried prior to milling.

TABLE 64

Granules Formulations

| Ingredient | Amount (% w/w) |
| --- | --- |
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 65

Coated Granules Formulation

| Ingredient | Amount (% w/w) |
| --- | --- |
| Hydromorphone granules | 50.0 |
| Ethylcellulose | 33.3 |
| Glycerol Behenate (Compritol 888 Ato) | 16.7 |
| Total | 100.00 |

Example 28

Coated Granules Lot#4002-40B (Compritol in the Core and not Cured and in the Coat and not Cured, 55% Coat)

Using a process similar to that described above in Example 17, but with using 72% of EC for dry mixing together with 20% glycerol behenate with other ingredients, the following formulation was prepared, which differs from Example 17 in the amounts of each component used. The wet granules were not partially dried prior to milling.

TABLE 66

Granules Formulations

| Ingredient | Amount (% w/w) |
| --- | --- |
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 67

Coated Granules Formulation

| Ingredient | Amount (% w/w) |
| --- | --- |
| Hydromorphone granules | 45.0 |
| Ethylcellulose | 36.7 |
| Glycerol Behenate (Compritol 888 Ato) | 18.3 |
| Total | 100.00 |

Example 29

Coated Granules Lot#4002-40C (Compritol in the Core and not Cured and in the Coat and not Cured, 60% Coat)

Using a process similar to that described above in Example 17, but with using 72% of EC for dry mixing together with 20% glycerol behenate with other ingredients, the following formulation was prepared, which differs from Example 17 in the amounts of each component used. The wet granules were not partially dried prior to milling.

TABLE 68

Granules Formulations

| Ingredient | Amount (% w/w) |
| --- | --- |
| Hydromorphone HCl | 46.6 |
| Hydroxypropyl methylcellulose (HPMC) | 16.4 |
| Ethylcellulose | 17.0 |
| Glycerol behenate | 20.0 |
| Total | 100.0 |

TABLE 69

Coated Granules Formulation

| Ingredient | Amount (% w/w) |
| --- | --- |
| Hydromorphone granules | 40.0 |
| Ethylcellulose | 40.0 |
| Glycerol Behenate (Compritol 888 Ato) | 20.0 |
| Total | 100.00 |

Example 30

Coated Granules Lot#4002-46 (Compritol in the Core and Cured and in the Coat and Cured, 40% Coat)

Using a process similar to that described above in Example 17, but with using 61% of EC for dry mixing together with 10% glycerol behenate with other ingredients, the following formulation was prepared, which differs from Example 17 in the amounts of each component used. The wet granules were not partially dried prior to milling. The uncoated granules were further cured by suspended them in the fluid bed while increasing the inlet air temperature. Curing was considered complete when the bed temperature was maintained above 65° C. for 30 minutes.

TABLE 70

Granules Formulations

| Ingredient | Amount (% w/w) |
|---|---|
| Hydromorphone HCl | 46.7 |
| Hydroxypropyl methylcellulose (HPMC) | 26.5 |
| Ethylcellulose | 16.8 |
| Glycerol behenate | 10.0 |
| Total | 100.0 |

TABLE 71

Coated Granules Formulation

| Ingredient | Amount (% w/w) |
|---|---|
| Hydromorphone granules | 60.0 |
| Ethylcellulose | 26.7 |
| Glycerol Behenate (Compritol 888 Ato) | 13.3 |
| Total | 100.00 |

After the right amount of coating has been sprayed into the granules, the coated granules were further cured by suspending them in the fluid bed while increasing the inlet air temperature. Curing was considered complete when the bed temperature was maintained above 65° C. for 30 minutes.

Example 31

Coated Granules Lot#4002-54 (Compritol in the Core and not Cured and in the Coat and not Cured, 40% Coat)

Using a process similar to that described above in Example 17, but with using 62% of EC for dry mixing together with 20% glycerol behenate with other ingredients, the following formulation was prepared, which differs from Example 17 in the amounts of each component used. The wet granules were not partially dried prior to milling.

TABLE 72

Granules Formulations

| Ingredient | Amount (% w/w) |
|---|---|
| Hydromorphone HCl | 46.6 |
| Hydroxypropyl methylcellulose (HPMC) | 26.4 |
| Ethylcellulose | 17.0 |
| Glycerol behenate | 10.0 |
| Total | 100.0 |

TABLE 73

Coated Granules Formulation

| Ingredient | Amount (% w/w) |
|---|---|
| Hydromorphone granules | 60.0 |
| Ethylcellulose | 26.7 |
| Glycerol Behenate (Compritol 888 Ato) | 13.3 |
| Total | 100.00 |

Example 32

Hydromorphone HCl (32 mg) Tablet Formulations
Lot #3766-69

Coated granules prepared as described herein above can be formed into solid dosage form, e.g., tablet. The coated granules can be mixed with EMCOMPRESS (dibasic calcium phosphate dihydrate), lactose (FAST-FLO, spray-dried), COMPRITOL ATO 888 (glyceryl behenate) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 74

Hydromorphone HCl (32 mg) Tablet Formulations

| Component | Amount (% w/w) |
|---|---|
| Hydromorphone coated granules (Example 17, Table 45) | 36.9 |
| EMCOMPRESS | 15.0 |
| Lactose | 37.1 |
| COMPRITOL (glyceryl behenate) | 10.00 |
| Magnesium Stearate | 1.0 |
| Total | 100.00 |

The above calculation is based on the actual rather than the theoretical potency of the coated granules

Example 33

Hydromorphone HCl (32 mg) Tablet Formulations
Lot #3766-70

The coated granules can be mixed with EMCOMPRESS (dibasic calcium phosphate dihydrate), lactose (FAST-FLO, spray-dried), COMPRITOL ATO 888 (glyceryl behenate) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 75

Hydromorphone HCl (32 mg) Tablet Formulations

| Component | Amount (% w/w) |
|---|---|
| Hydromorphone coated granules (Example 22, Table 55) | 39.0 |
| EMCOMPRESS | 15.0 |
| Lactose | 35.0 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 34

Hydromorphone HCl (32 mg) Tablet Formulations
Lot #3766-72

The coated granules can be mixed with lactose (FAST-FLO, spray-dried), COMPRITOL ATO 888 (glyceryl behenate), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 76

Hydromorphone HCl (32 mg) Tablet Formulations

| Component | Amount (% w/w) |
|---|---|
| Hydromorphone coated granules (Example 22, Table 55) | 39.0 |
| Benecel MP844 (Hypromellose) | 10.0 |
| Lactose | 40.0 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 35

Hydromorphone HCl (32 mg) Tablet Formulations
Lot #3766-73

The coated granules can be mixed with lactose (FAST-FLO, spray-dried), COMPRITOL ATO 888 (glyceryl behenate), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 77

Hydromorphone HCl (32 mg) Tablet Formulations

| Component | Amount (% w/w) |
|---|---|
| Hydromorphone coated granules (Example 17, Table 45) | 36.9 |
| Benecel MP844 (Hypromellose) | 10.0 |
| Lactose | 42.1 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 36

Hydromorphone HCl (32 mg) Tablet Formulations
Lot #3766-87

The coated granules can be mixed with lactose (FAST-FLO, spray-dried), COMPRITOL ATO 888 (glyceryl behenate), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 78

Hydromorphone HCl (32 mg) Tablet Formulations

| Component | Amount (% w/w) |
|---|---|
| Hydromorphone coated granules (Example 17, Table 45) | 38.7 |
| Benecel MP844 (Hypromellose) | 20.0 |
| Lactose | 30.3 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 37

Hydromorphone HCl (32 mg) Tablet Formulations
Lot #3766-88

The coated granules can be mixed with lactose (FAST-FLO, spray-dried), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 79

Hydromorphone HCl (32 mg) Tablet Formulations

| Component | Amount (% w/w) |
|---|---|
| Hydromorphone coated granules (Example 17, Table 45) | 38.7 |
| Benecel MP844 (Hypromellose) | 20.0 |
| Lactose | 40.3 |
| Magnesium Stearate | 1.0 |
| Total | 100.00 |

The above calculation is based on the actual rather than the theoretical potency of the coated granules.

Example 38

Hydromorphone HCl (32 mg) Tablet Formulations
Lot #3766-89

The coated granules can be mixed with lactose (FAST-FLO, spray-dried), ethyl cellulose NT 10, COMPRITOL (glycerol behenate) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 80

Hydromorphone HCl (32 mg) Tablet Formulations

| Component | Amount (% w/w) |
|---|---|
| Hydromorphone coated granules (Example 17, Table 45) | 38.7 |
| Ethyl Cellulose NT 10 | 50.3 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 39

Hydromorphone HCl (32 mg) Tablet Formulations
Lot #3766-57

The coated granules can be mixed with lactose (FAST-FLO, spray-dried), COMPRITOL (glyceryl behenate) in a V-blender for a period of about 30 minutes. The blended mixture can then be compressed in a rotary tablet press to form 400 mg round shaped tablets with diameter of ⅜". Using this process, the following tablet was prepared:

TABLE 81

Hydromorphone HCl (32 mg) Tablet Formulations

| Component | Amount (% w/w) |
|---|---|
| Hydromorphone coated granules (Example 22, Table 55) | 39.0 |
| Lactose | 51.0 |
| COMPRITOL (glyceryl behenate) | 10.0 |
| Total | 100.00 |

The above calculation is based on the actual rather than the theoretical potency of the coated granules.

Example 40

Hydromorphone HCl (32 mg) Tablet Formulations
Lot #4002-57

The coated granules can be mixed with lactose (FAST-FLO, spray-dried), in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 82

Hydromorphone HCl (32 mg) Tablet Formulations

| Component | Amount (% w/w) |
|---|---|
| Hydromorphone coated granules (Example 30, Table 71) | 27.8 |
| lactose | 71.2 |
| Magnesium Stearate | 1.0 |
| Total | 100.00 |

The above calculation is based on the actual rather than the theoretical potency of the coated granules.

Example 41

Hydromorphone HCl (32 mg) Tablet Formulations
Lot #4002-60

The coated granules can be mixed with lactose (FAST-FLO, spray-dried), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 83

Hydromorphone HCl (32 mg) Tablet Formulations

| Component | Amount (% w/w) |
|---|---|
| Hydromorphone coated granules (Example 30, Table 71) | 27.8 |
| Benecel MP844 (Hypromellose) | 10.0 |
| Lactose | 61.2 |
| Magnesium Stearate | 1.0 |
| Total | 100.00 |

The above calculation is based on the actual rather than the theoretical potency of the coated granules.

Example 42

Hydromorphone HCl (32 mg) Tablet Formulations
Lot #4002-61

The coated granules can be mixed with lactose (FAST-FLO, spray-dried), COMPRITOL ATO 888 (glyceryl behenate), Benecel MP844 (Hypromellose) in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 84

Hydromorphone HCl (32 mg) Tablet Formulations

| Component | Amount (% w/w) |
|---|---|
| Hydromorphone coated granules (Example 30, Table 71) | 27.8 |
| Benecel MP844 (Hypromellose) | 10.0 |
| Lactose | 51.2 |
| COMPRITOL (glyceryl behenate) | 10.0 |
| Magnesium Stearate | 1.0 |
| Total | 100.00 |

The above calculation is based on the actual rather than the theoretical potency of the coated granules.

Example 43

Hydromorphone HCl (32 mg) Tablet Formulations Lot #4002-58

The coated granules can be mixed with lactose (FAST-FLO, spray-dried), in a V-blender for a period of about 30 minutes. Magnesium stearate is then added to the blend and mixed for additional 5 minutes. The blended mixture can then be compressed in a rotary tablet press to form 400 mg round shaped tablets with diameter of ⅜". Using this process, the following tablet was prepared:

TABLE 85

Hydromorphone HCl (32 mg) Tablet Formulations

| Component | Amount (% w/w) |
|---|---|
| Hydromorphone coated granules (Example 31, Table 73) | 28.0 |
| lactose | 71.0 |
| Magnesium Stearate | 1.0 |
| Total | 100.00 |

The above calculation is based on the actual rather than the theoretical potency of the coated granules.

Example 44

Coated Granules Lot 4002-73 (Carnauba Wax in Core and Coat, No Curing)

Using a process similar to that described above in Example 17, but with using 62% of EC for dry mixing together with 10% carnauba wax with other ingredients, the following formulation was prepared, which differs from Example 17 in the amounts of each component used. The wet granules were not partially dried prior to milling.

TABLE 86

Granules Formulations

| Ingredient | Amount (% w/w) |
|---|---|
| Hydromorphone HCl | 46.6 |
| Hydroxypropyl methylcellulose (HPMC) | 26.4 |
| Ethylcellulose | 17.0 |
| Carnauba Wax | 10.0 |
| Total | 100.0 |

TABLE 89

Coated Granules Formulation

| Ingredient | Amount (% w/w) |
|---|---|
| Hydromorphone granules | 60.0 |
| Ethylcellulose | 26.7 |
| Carnauba Wax | 13.3 |
| Total | 100.00 |

Example 45

Coated Granules Lot 4002-76 (Gelucire 50/13 in Core and Coat, not Cured)

Using a process similar to that described above in Example 17, but with using 64% of EC for dry mixing together with 10.1% Gelucire 50/13 with other ingredients, the following formulation was prepared, which differs from Example 17 in the amounts of each component used. Before granulation, Gelucire 50/13 was first milled and sieved through a 30 mesh screen prior to mixing with other materials. The wet granules were not partially dried prior to milling.

TABLE 90

Granules Formulations

| Ingredient | Amount (% w/w) |
|---|---|
| Hydromorphone HCl | 46.8 |
| Hydroxypropyl methylcellulose (HPMC) | 26.5 |
| Ethylcellulose | 16.6 |
| Gelucire 50/13 | 10.1 |
| Total | 100.0 |

Before coating, Gelucire 50/13 was first milled and sieved through a 200-mesh screen prior to adding to the ethanolic EC solution.

TABLE 91

Coated Granules Formulation

| Ingredient | Amount (% w/w) |
|---|---|
| Hydromorphone granules | 60.0 |
| Ethylcellulose | 26.7 |
| Gelucire 50/13 | 13.3 |
| Total | 100.00 |

Example 46

A number of lots of tablets including the coated granules of the present invention were produced as shown in Table 92 below.

TABLE 92

| Coated Gran. | Tablet Lots | Tablet Average Hardness (N) |
|---|---|---|
| 3766-06 | 3766-69 | 50 |
|  | 3766-73 | 40 |
| 3766-80 | 3766-87 | 47 |
|  | 3766-88A, B | 55, 74 |
|  | 3766-89 | 38 |
| 3766-33 | 3766-57 | 52 |
|  | 3766-70 | 45 |
|  | 3766-72 | 40 |
| 4002-46 | 4002-57 | 80 |
|  | 4002-60 | 70-80 |
|  | 4002-61 | 48 |
| 4002-54 | 4002-58 | 80 |

The tablet lot numbers are indicated in the second column and the coated granulates used (whose production were described earlier) are indicated in the first column. The third column provides the average tablet hardness. Details of the manufacturing process can be found in the pertaining example sections.

Tables 93, 94 and 95 identify the tablet lot to the left and provide dissolution information at various times for each lot. Lot 3766-57, for example, were 400 milligram tablets having a hardness of 52 Newtons, which were round and ¾ of an inch. These tablets included coated granulate lot 3766-33, whose production was described in example 22. As shown in Table 93, these tablets when tested using the USP dissolution apparatus number 2 using 500 ml of 0.1 N HCl (normal dissolution) or 40% ethanolic solution (dose dumping dissolution) as the dissolution medium. Simulated oral tampering testing was conducted by crushing the tablets using ceramic mortars and pestles. Each tablet was placed in a ceramic mortar (13 cm outer diameter) then by using a pestle and applying force vertically downward, the tablets are crushed by 360° C. circular motion. Each full circle motion constitutes 1 stroke. Each table is crushed by applying 12 strokes as described above. The crushed powder are then analyzed using USP apparatus number 2 and the dissoluation data at 30 minutes was considered. This lot exhibited a 29% release at four hours, a 58% release at 8 hours and a 90% release at 16 hours. As shown in Table 94, the same lot released 51% within two hours upon exposure to ethanol. This is compared to a 13% release under normal conditions. In this particular instance, such a discrepancy was not considered successful in terms of solvent resistance. According to Table 95, the same tablet lot showed a release of 36% at 30 minutes after simulated tampering as described herein.

TABLE 93

Hydromorphone Tablets (32 mg) Normal Dissolution

% Released in Time (hrs)

| Lot # | 0 | 1 | 2 | 4 | 8 | 12 | 16 | 20 | 24 |
|---|---|---|---|---|---|---|---|---|---|
| 3766-57 | 0 | 8 | 13 | 29 | 58 | 81 | 90 | 94 | 96 |
| 3766-69 | 0 | 24 | 53 | 88 | 96 | 98 | 98 | 99 | 99 |
| 3766-70 | 0 | 8 | 13 | 30 | 60 | 80 | 88 | 91 | 92 |
| 3766-72 | 0 | 5 | 8 | 18 | 42 | 64 | 81 | 93 | 98 |
| 3766-73 | 0 | 9 | 21 | 41 | 67 | 83 | 94 | 99 | 102 |
| 3766-87 | 0 | 4 | 11 | 29 | 57 | 76 | 90 | 99 | 104 |
| 3766-88A | 0 | 6 | 17 | 36 | 62 | 79 | 90 | 95 | 98 |
| 3766-88B | 0 | 6 | 16 | 36 | 64 | 82 | 93 | 99 | 101 |
| 3766-89 | 0 | 3 | 11 | 54 | 99 | 102 | 103 | 103 | 104 |
| 4002-57 | 0 | 7 | 26 | 67 | 95 | 102 | 105 | 107 | 108 |
| 4002-58 | 0 | 8 | 28 | 62 | 86 | 94 | 97 | 98 | 100 |
| 4002-60 | 0 | 2 | 8 | 24 | 54 | 76 | 90 | 96 | 98 |
| 4002-61 | 0 | 2 | 5 | 17 | 46 | 72 | 90 | 101 | 105 |

TABLE 94

Dose Dumping Dissolution

| | % Released in Time (min) | | | | | Normal Dissolution |
|---|---|---|---|---|---|---|
| Lot# | 0 | 15 | 30 | 45 | 60 | 120 | release in 2 hr |
| 3766-57 | 0 | 2 | 4 | 7 | 13 | 51 | 13 |
| 3766-69 | 0 | 2 | 6 | 12 | 16 | 33 | 53 |
| 3766-70 | 0 | 2 | 3 | 5 | 9 | 24 | 13 |
| 3766-72 | 0 | 1 | 2 | 3 | 4 | 14 | 8 |
| 3766-73 | 0 | 1 | 3 | 5 | 8 | 19 | 21 |
| 3766-87 | 0 | 1 | 2 | 2 | 4 | 14 | 11 |
| 3766-88A | 0 | 1 | 2 | 3 | 5 | 14 | 17 |
| 3766-88B | 0 | 1 | 2 | 3 | 5 | 16 | 16 |
| 3766-89 | 0 | 3 | 38 | 67 | 83 | 98 | 11 |
| 4002-57 | 0 | 3 | 16 | 46 | 72 | 96 | 26 |
| 4002-58 | 0 | 3 | 20 | 47 | 71 | 94 | 28 |
| 4002-60 | 0 | 1 | 3 | 8 | 14 | 29 | 8 |
| 4002-61 | 0 | 1 | 2 | 6 | 11 | 25 | 5 |

TABLE 95

Simulated Oral Tampering Dissolution

% Released in Time (min)

| Lot # | 0 | 15 | 30 | 45 | 60 | 120 |
|---|---|---|---|---|---|---|
| 3766-57 | 0 | 24 | 36 | 44 | 48 | 57 |
| 3766-72 | 0 | 19 | 28 | 36 | 42 | 55 |
| 3766-73 | 0 | 31 | 63 | 75 | 84 | 94 |
| 3766-87 | 0 | 19 | 38 | 53 | 64 | 87 |
| 3766-88A | 0 | 32 | 50 | 66 | 74 | 88 |
| 3766-88B | 0 | 38 | 52 | 66 | 75 | 89 |
| 3766-89 | 0 | 29 | 51 | 65 | 73 | 88 |
| 4002-57 | 0 | 13 | 23 | 29 | 36 | 54 |
| 4002-58 | 0 | 20 | 34 | 44 | 52 | 69 |
| 4002-60 | 0 | 19 | 31 | 39 | 46 | 66 |
| 4002-61 | 0 | 13 | 27 | 40 | 50 | 67 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. An abuse resistant tablet consisting of:
 a. a plurality of coated granules, wherein each coated granule consists of:
  i. a granule consisting of:
   a. an opioid, and/or a salt thereof, present in an amount in the range of from 20 to 60 percent by weight of the uncoated granule;
   b. ethylcellulose present in an amount in the range of from 10 to 75 percent by weight of the uncoated granule;

c. hydroxypropyl methyl cellulose present in an amount in the range of from 15 to 50 percent by weight of the uncoated granule; and
ii. a coating substantially surrounding the granule, wherein the coating consists of:
a. ethyl cellulose present in an amount in the range of from 20 to 60 percent by weight of the coated granule;
b. glyceryl behenate present in an amount in the range of from 10 to 30 percent by weight of the coated granule;
wherein the plurality of coated granules are present in the tablet in an amount to provide a therapeutically effective amount of the opioid, and/or a salt thereof; and
b. a matrix composition comprising:
i. hydroxypropyl methyl cellulose present in an amount in the range of from 2 to 20 percent by weight of the tablet; and
ii. lactose present in an amount in the range of from 10 to 75 percent by weight of the tablet.

2. The abuse resistant tablet of claim 1, wherein the coated granules release 21 percent or less of the opioid, and/or salt thereof, when the coated granules are crushed and the crushed coated granules are tested for 30 minutes in a United States Pharmacopeia apparatus number 2 using a dissolution media.

3. The abuse resistant tablet of claim 1, wherein the coated granules release a lower amount of the opioid, and/or salt thereof, when the coated granules are crushed and the crushed coated granules are tested for 30 minutes in a United States Pharmacopeia apparatus number 2 using a dissolution media, as compared to similar coated particles that have magnesium stearate in the coating instead of the glyceryl behenate.

4. The abuse resistant tablet of claim 3, wherein the coated granules release 15 percent or less of the opioid, and/or salt thereof, when the coated granules are crushed and the crushed coated granules are tested for 30 minutes in a United States Pharmacopeia apparatus number 2 using a dissolution media.

5. The abuse resistant tablet of claim 1, wherein the opioid comprises hydrocodone, and/or a salt thereof.

6. An abuse resistant tablet consisting of:
a. a plurality of coated granules, wherein each coated granule consists of:
i. a granule consisting of:
a. an opioid, and/or a salt thereof, present in an amount in the range of from 20 to 60 percent by weight of the uncoated granule;
b. ethyl cellulose present in an amount in the range of from 10 to 75 percent by weight of the uncoated granule;
c. hydroxypropyl methyl cellulose present in an amount in the range of from 15 to 50 percent by weight of the uncoated granule; and
ii. a coating substantially surrounding the granule, wherein the coating consists of:
a. ethyl cellulose present in an amount in the range of from 20 to 60 percent by weight of the coated granule;
b. glyceryl behenate present in an amount in the range of from 10 to 30 percent by weight of the coated granule;
wherein the plurality of coated granules are present in the tablet in an amount to provide a therapeutically effective amount of the opioid, and/or a salt thereof; and
b. a matrix composition comprising:
i. hydroxypropyl methyl cellulose present in an amount in the range of from 2 to 20 percent by weight of the tablet; and
ii. lactose present in an amount in the range of from 10 to 75 percent by weight of the tablet;
wherein the tablet releases 29 percent or less of the opioid and/or a salt thereof, when the tablet is tested for two hours in a United States Pharmacopeia apparatus number 2 using a 40 percent ethanolic solution and wherein the tablet releases 31 percent or less of the opioid, and/or salt thereof, when the tablet is crushed and the crushed tablet is tested for 30 minutes in a United States Pharmacopeia apparatus number 2 using 0.1N hydrochloric acid.

7. The abuse-resistant tablet of claim 6, wherein the opioid comprises hydrocodone, and/or a salt thereof.

8. An abuse resistant tablet consisting of:
a. a plurality of coated granules, wherein each coated granule consists of:
i. a granule consisting of:
a. an opioid, and/or a salt thereof, present in an amount in the range of from 20 to 60 percent by weight of the uncoated granule;
b. ethylcellulose present in an amount in the range of from 10 to 75 percent by weight of the uncoated granule;
c. hydroxypropyl methyl cellulose present in an amount in the range of from 15 to 50 percent by weight of the uncoated granule; and
ii. a coating substantially surrounding the granule, wherein the coating consists of:
a. ethyl cellulose present in an amount in the range of from 20 to 60 percent by weight of the coated granule;
b. glyceryl behenate present in an amount in the range of from 10 to 30 percent by weight of the coated granule;
wherein the plurality of coated granules are present in the tablet in an amount to provide a therapeutically effective amount of the opioid, and/or a salt thereof; and
b. a matrix composition comprising:
i. hydroxypropyl methyl cellulose present in an amount in the range of from 2 to 20 percent by weight of the tablet;
ii. lactose present in an amount in the range of from 10 to 75 percent by weight of the tablet; and
iii. magnesium stearate present in an amount in the range of from 0.25 to 2 percent by weight of the tablet;
wherein the percent of the opioid, and/or a salt thereof, released after 30 minutes in a solution of 0.1N hydrochloric acid and 40 percent ethanol is no more than 21 percentage points greater than the percent of the opioid, and/or a salt thereof, released in a solution of 0.1N hydrochloric acid without ethanol.

9. An abuse resistant tablet comprising:
a. a plurality of coated granules, wherein each coated granule consists of:
i. a granule consisting of:
a. hydrocodone, and/or a salt thereof, present in an amount in the range of from 20 to 60 percent by weight of the uncoated granule;
b. ethylcellulose present in an amount in the range of from 10 to 75 percent by weight of the uncoated granule;
c. hydroxypropyl methyl cellulose present in an amount in the range of from 15 to 50 percent by weight of the uncoated granule; and ii. a coating substantially surrounding the granule, wherein the coating consists of:
   a. ethyl cellulose present in an amount in the range of from 20 to 60 percent by weight of the coated granule;
   b. glyceryl behenate present in an amount in the range of from 10 to 30 percent by weight of the coated granule;

wherein the plurality of coated granules are present in the tablet in an amount to provide a therapeutically effective amount of the hydrocodone, and/or a salt thereof; and b. a matrix composition comprising:
   i. hydroxypropyl methyl cellulose present in an amount in the range of from 2 to 20 percent by weight of the tablet; and
   ii. lactose present in an amount in the range of from 10 to 75 percent by weight of the tablet.

10. The abuse resistant tablet of claim 9, wherein the glyceryl behenate is present in an amount in the range of from 10 to 20 percent by weight of the coated granule.

11. The abuse resistant tablet of claim 10, wherein the coating is present in an amount in the range of from 30 to 60 percent by weight of the coated granule.

12. The abuse resistant tablet of claim 10, wherein the lactose is spray-dried lactose.

13. The abuse resistance tablet of claim 10, wherein the hydroxypropyl methyl cellulose present in the tablet matrix composition is present in an amount ranging from 2 to 10 percent by weight of the tablet.

14. The abuse resistance tablet of claim 10, wherein the ethylcellulose of the granule is present in an amount in the range of from 40 to 75 percent by weight of the uncoated granule and hydroxypropyl methyl cellulose of the granules is present in an amount in the range of from 22 to 50 percent by weight of the uncoated granule.

* * * * *